United States Patent [19]

Shibata et al.

[11] Patent Number: 5,723,408
[45] Date of Patent: Mar. 3, 1998

[54] HERBICIDE COMPOSITION COMPRISING 4-(BENZOTHIOPYRAN-6-CARBONYL) PYRAZOLES

[75] Inventors: Mitsuru Shibata, Sodegaura; Ichiro Nasuno, Ichihara; Kazufumi Nakamura, Chita; Kazuyoshi Koike, Sodegaura; Misako Yoshikawa, Yotsukaido, all of Japan

[73] Assignee: Idemitsu Kosan Co., Ltd., Tokyo, Japan

[21] Appl. No.: 750,665

[22] PCT Filed: Jun. 27, 1995

[86] PCT No.: PCT/JP95/01280

§ 371 Date: Mar. 24, 1997

§ 102(e) Date: Mar. 24, 1997

[87] PCT Pub. No.: WO96/00008

PCT Pub. Date: Jan. 4, 1996

[30] Foreign Application Priority Data

Jun. 27, 1994 [JP] Japan ..................... 6-144773
Sep. 20, 1994 [JP] Japan ..................... 6-223906
Sep. 27, 1994 [JP] Japan ..................... 6-230127

[51] Int. Cl.⁶ ......................... A01N 43/18; A01N 43/56
[52] U.S. Cl. ............................. 504/139; 504/282
[58] Field of Search ............................ 504/139, 282

[56] References Cited

FOREIGN PATENT DOCUMENTS

WO 93/18031   9/1993   WIPO .
WO 94/01431   1/1994   WIPO .

OTHER PUBLICATIONS

Shibata et al. CA 12:164162b. Abstract of PCT Application WO 93/18,031. 16 Sep. 1993.

Nasuno et al. CA 120:245092f. Abstract of PCT Application WO 94/01,431. 20 Jan. 1994.

*Primary Examiner*—S. Mark Clardy
*Attorney, Agent, or Firm*—Frishauf, Holtz, Goodman, Langer & Chick, P.C.

[57] ABSTRACT

Provided by the present invention is a herbicide composition containing, as active ingredients, a pyrazole derivative of the general formula (I)

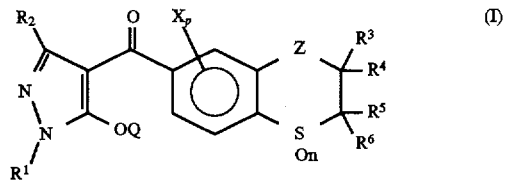

and at least one herbicide compound selected from the group consisting of chloroacetamide-containing herbicides, imidazoline-containing herbicides, atrazine, cyanazine, metribuzin, linuron, metobenzuron, bentazone, dicamba, chlopyralid, 2,4-D, bromoxynil, pendimethalin, nicosulfuron, rimsulfuron, primisulfuron and pyridate. The herbicide composition of the present invention can control a broad rage of gramineous weeds and broad-leaved weeds at a very low dosage without damaging corn and other crops.

20 Claims, No Drawings

HERBICIDE COMPOSITION COMPRISING 4-(BENZOTHIOPYRAN-6-CARBONYL) PYRAZOLES

This application has been filed under 35 USC 371 as a national stage application of PCT/JP95/02180, filed Jun. 27, 1995.

TECHNICAL FIELD

The present invention relates to a herbicide composition containing pyrazole derivative.

TECHNICAL BACKGROUND

Herbicides are very important chemicals for saving weed-controlling labors and improving the yield of agricultural and horticultural crops and have been therefore aggressively studied and developed for many years, and a diversity of herbicides have now been put to practical use. However, it cannot be said that herbicides which have been so far developed have broad herbicidal spectra, and at present there are an increasing number of weeds which are difficult to control. Herbicides having broad herbicidal spectra are therefore desired. For overcoming the environmental pollution problem of conventional herbicides, further, there are desired herbicides which are effective at a further decreased dosage.

The present inventors already found that a variety of pyrazole derivatives in which a thiochroman ring is bonded to a pyrazole ring through a carbonyl group is free from damaging gramineous upland crops but can control gramineous weeds and broad-leaved weeds together at a low dosage by any one of soil treatment and foliar treatment, and filed patent applications directed to these pyrazole derivatives and herbicides containing these as active ingredients. Of these patent applications, some have been already laid-open as International Laid-open Patent Publications Nos. WO95/04054, WO93/18031, WO94/01431 and WO95/13275. Japanese Patent Applications Nos. 6-237981, 7-80059 and 7-158842 have not yet been laid-open.

Those pyrazole derivatives disclosed in the above International Laid-open Patent Publications and Japanese Patent Applications can control gramineous weeds and broad-leaved weeds together at a low dosage by any one of soil treatment and foliar treatment, while there is desired a herbicide which can control a broad range of gramineous weeds and broad-leaved weeds at a further decreased dosage.

It is therefore an object of the present invention to provide herbicide compositions which can control a broad range of gramineous weeds and broad-leaved weeds at a very low dosage without damaging crops such as corn, etc., by using the pyrazole derivatives disclosed in the International Laid-open Patent Publications and the above Japanese Patent Applications in combination with other herbicide compounds.

The present inventors have made diligent studies to achieve the above object, and as a result have found that when a pyrazole derivative of the following general formula (I) described in the above International Laid-open Patent Publications and Japanese Patent Applications (to be sometimes referred to as "pyrazole derivative (I)" hereinafter) and a specific herbicide compound are used in combination, a broad range of gramineous weeds and broad-leaved weeds can be controlled at a very low dosage by synergistic effects of the pyrazole derivative (I) and the said specific herbicide compound without damaging crops such as corn, etc. The present invention has been accordingly completed.

DISCLOSURE OF THE INVENTION

The gist of the present invention is a herbicide composition containing, as active ingredients, a pyrazole derivative of the general formula (I),

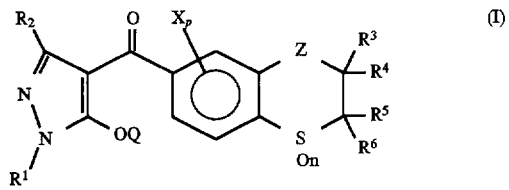

{wherein:

$R^1$ is a $C_1$-$C_4$ alkyl group, a $C_2$-$C_4$ alkenyl group or a $C_2$-$C_4$ haloalkeny group, $R^2$ is a hydrogen atom, a $C_1$-$C_4$ alkyl group, a $C_1$-$C_4$ haloalkyl group or a $C_2$-$C_4$ alkoxyalkyl group, X is a $C_1$-$C_4$ alkyl group, a $C_1$-$C_4$ haloalkyl group, a $C_2$-$C_4$ alkoxyalkyl group, a halogen atom, a $C_1$-$C_4$ alkoxy group or a $C_1$-$C_4$ haloalkoxy group, p is an integer of 0, 1 or 2, each of $R^3$, $R^4$, $R^5$ and $R^6$ is independently a hydrogen atom, a $C_1$-$C_4$ alkyl group, a $C_1$-$C_4$ haloalkyl group or a $C_2$-$C_4$, alkoxyalkyl group, n is an integer of 0, 1 or 2, Q is a hydrogen atom or a group of A—B, [in which A is a group of

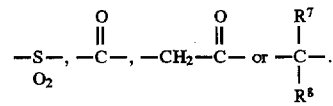

(in which each of $R^7$ and $R^8$ is independently a hydrogen atom or a $C_1$-$C_4$, alkyl group), and B is a $C_1$-$C_{12}$ alkyl group, a $C_3$-$C_{10}$ cycloalkyl group or a group of

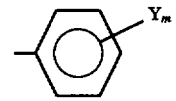

(in which Y is a $C_1$-$C_4$ alkyl group, a $C_1$-$C_4$ alkoxy group, a $C_1$-$C_4$ haloalkyl group, a nitro group or a halogen atom, and m is an integer of 0 or 1~3)], and Z is

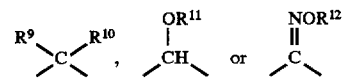

[in which $R^9$ is a hydrogen atom, a $C_1$-$C_4$ alkyl group or a $C_1$-$C_4$ haloalkyl group, $R^{10}$ is a hydrogen atom, a $C_1$-$C_4$ alkyl group, a $C_2$-$C_4$ alkenyl group or a $C_2$-$C_4$ alkynyl group, $R^{11}$ is a $C_1$-$C_4$ alkyl group, a $C_1$-$C_4$ haloalkyl group, a $C_3$-$C_6$ cycloalkyl group, a $C_3$-$C_6$ alkenylalkyl group, a $C_3$-$C_6$ alkynylalkyl group or a $C_3$-$C_6$ haloalkenylalkyl group, $R^{12}$ is a $C_1$-$C_4$ alkyl group, a $C_1$-$C_4$ haloalkyl group, a $C_3$-$C_6$ cycloalkyl group, a $C_3$-$C_6$ alkenylalkyl group, a $C_3$-$C_6$ alkynylalkyl group or a $C_3$-$C_6$ haloalkenylalkyl group]}, or a salt thereof; and at least one herbicide compound selected from the group consisting of chloroacetamide-containing herbicides such as alachlor, metolachlor, acetochlor and dimethenamide, etc., imidazoline-containing herbicides such as imazetapyr, etc., atrazine, cyanazine, metribuzin, linuron, methbenzurone, bentazone, dicamba, chlopyralid, 2,4-D, bromoxynil, pendimethalin, nicosulfuron, rimsulfuron, primisulfuron and pyridate.

PREFERRED EMBODIMENTS OF THE INVENTION

The pyrazole derivative as a first active ingredient of the herbicide composition of the present invention has the following general formula (I).

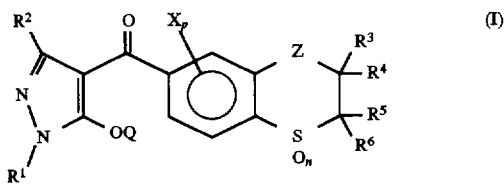

The herbicide composition of the present invention contains, as an active ingredient, at least one of pyrazole derivatives of the above general formula (I).

In the general formula (I), $R^1$ is a $C_1$~$C_4$ alkyl group, a $C_2$~$C_4$ alkenyl group or a $C_2$~$C_4$ haloalkenyl group, and preferred is a $C_1$~$C_4$ alkyl group. Specific examples of the $C_1$~$C_4$ alkyl group include methyl, ethyl, propyl and butyl, and the propyl and the butyl may be any one of linear, cyclic and branched ones. The $C_1$~$C_4$ alkyl group is preferably methyl or ethyl. Specific examples of the $C_2$~$C_4$ alkenyl group include —CH=CH$_2$, —CH$_2$—CH=$_{CH2}$ and —CH=CH—CH=CH$_2$. The $C_2$~$C_4$ haloalkeny group includes those in which at least one hydrogen atom of the above $C_2$~$C_4$ alkenyl group is replaced with a halogen atom (e.g., a chlorine atom, a fluorine atom, a bromine atom or an iodine atom).

In the general formula (I), $R^2$ is a hydrogen atom, a $C_1$~$C_4$ alkyl group, a $C_1$~$C_4$ haloalkyl group or a $C_2$~$C_4$ alkoxyalkyl group, and preferred is a hydrogen atom or a $C_1$~$C_4$ alkyl group. Specific examples of the $C_1$~$C_4$ alkyl group are as described concerning $R^1$, and methyl is preferred. The $C_1$~$C_4$ haloalkyl group includes those in which at least one hydrogen atom of the $C_1$~$C_4$ alkyl group is replaced with a halogen atom (e.g., chlorine atom, a fluorine atom, a bromine atom or an iodine atom), and examples thereof include —CF$_3$, —C$_2$F$_5$, —C$_2$H$_4$F, —CH$_2$Cl, —CHF$_2$, —CCl$_3$, —C$_2$H$_3$Cl$_2$ and —C$_2$H$_3$F$_2$. Specific examples of the $C_2$~$C_4$ alkoxyalkyl group include —CH$_2$—OCH$_3$, —CH$_2$—OC$_2$H$_5$, —CH$_2$—OC$_3$H$_7$, —CH(CH$_3$)OCH$_3$, —CH(CH$_3$)OC$_2$H$_5$, —C$_2$CH$_3$OCH$_3$ and —CH$_2$CH$_2$OC$_2$H$_5$.

In the general formula (I), X is a $C_1$~$C_4$ alkyl group, a $C_1$~$C_4$ haloalkyl group, a $C_2$~$C_4$ alkoxyalkyl group, a halogen atom, a $C_1$~$C_4$ alkoxy group or a $C_1$~$C_4$ haloalkoxy group, and preferred is a $C_1$~$C_4$ alkyl group or a halogen atom. Specific examples of the $C_1$~$C_4$ alkyl group, the $C_1$~$C_4$ haloalkyl group and the $C_2$~$C_4$ alkoxyalkyl group are as described concerning $R^1$ or $R^2$. Specific examples of the $C_1$~$C_4$ alkyl group preferably include methyl or ethyl. Specific examples of the halogen atom include a chlorine atom, a fluorine atom, a bromine atom and an iodine atom, and a chlorine atom is preferred. Specific examples of the $C_1$~$C_4$ alkoxy group include methoxy, ethoxy, propoxy and butoxy, and the propoxy and the butoxy may be linear, cyclic or branched ones. The $C_1$~$C_4$ haloalkoxy group include those in which at least one hydrogen atom of the $C_1$~$C_4$ alkoxy group is replaced with a halogen atom (e.g., a chlorine atom, a fluorine atom, a bromine atom or an iodine atom), and examples thereof include —OCF$_3$, —OC$_2$F$_5$, —OC$_2$H$_4$F, —OC$_2$H$_4$Cl, —OCHF$_2$, —OCH$_2$F, —OCCl$_3$, —OC$_2$H$_3$Cl$_2$ and —OC$_2$H$_3$F$_2$.

In the general formula (I), p is the number of substituent (s) X, and it is an integer of 0, 1 or 2. When p is 1 or 2, the position(s) of the substituent(s) X is/are the 5-position and/or 8-position on the thiochroman ring.

In the general formula (I), each of $R^3$, $R^4$, $R^5$ and $R^6$ is independently a hydrogen atom, a $C_1$~$C_4$ alkyl group, a $C_1$~$C_4$ haloalkyl group or a $C_2$~$C_4$ alkoxyalkyl group. Each of these is preferably independently a hydrogen atom or a $C_1$~$C_4$ alkyl group. Specific examples of the $C_1$~$C_4$ alkyl group, the $C_1$~$C_4$ haloalkyl group and the $C_2$~$C_4$ alkoxyalkyl group are as described concerning $R^1$ or $R^2$.

In the general formula (I), n is the number of oxygen atom(s) bonding to the sulfur atom of the thiochroman ring, and it is an integer of 0 (sulfide), 1 (sulfoxide) or 2 (sulfone) and is preferably 2 (sulfone).

In the general formula (I), Q is a hydrogen atom or a group of —A—B.

In the definition of Q,

A is a group of

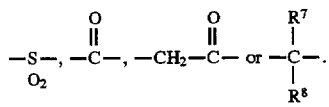

In the definition of A, each of $R^7$ and $R^8$ is independently a hydrogen atom or a $C_1$~$C_4$ alkyl group, and each is preferably a hydrogen atom. Specific examples of the $C_1$~$C_4$ alkyl group are as described concerning $R^1$.

In the definition of Q, B is a $C_1$~$C_{12}$ alkyl group, a $C_3$~$C_{10}$ cycloalkyl group or a group of

Specific examples of the $C_1$~$C_{12}$ alkyl group includes those described as specific examples of the $C_1$~$C_4$ alkyl group for $R^1$ and others such as pentyl, hexyl, heptyl, octyl, nonyl, decanyl, undecanyl and dodecanyl. Those which have at least 3 carbon atoms may be linear or branched. Preferred is a $C_1$~$C_8$ alkyl group. Specific examples of the $C_3$~$C_{10}$ alkyl group include cyclopropyl, cyclobutyl, cyclopentyl, cyclohexyl and cycloheptyl, and cyclohexyl is preferred.

In the group of

which is one embodiment of B, Y is a $C_1$~$C_4$ alkyl group, a $C_1$~$C_4$ alkoxy group, a $C_1$~$C_4$ haloalkyl group, a nitro group or a halogen atom, and preferred is a $C_1$~$C_4$ alkyl group, a $C_1$~$C_4$ alkoxy group, a nitro group or a halogen atom. Specific examples of the $C_1$~$C_4$ alkyl group, the $C_1$~$C_4$ alkoxy group, the $C_1$~$C_4$ haloalky group and the halogen atom are as described concerning $R^1$, $R^2$ or X. The $C_1$–$C_4$ alkyl group is specifically preferably methyl. The $C_1$–$C_4$ alkoxy group is specifically preferably methoxy. The halogen atom is specifically preferably a chorine or fluorine atom.

m is the number of substituent(s) Y, and it is an integer of 0 or 1 to 3, preferably 0, 1 or 2.

In the general formula (I), Z is

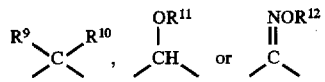

The pyrazole derivative (I) of the present invention can be classified into three kinds depending upon embodiments of Z. That is, the pyrazole derivative in which Z is

has the following general formula (Ia).

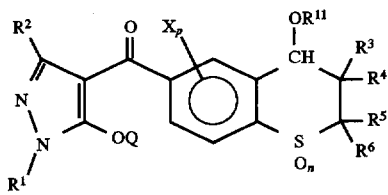

In the general formula (Ia), $R^{11}$ is a $C_1$–$C_4$ alkyl group, a $C_1$–$C_4$ haloalkyl group, a $C_3$–$C_6$ cycloalkyl group, a $C_3$–$C_6$ alkenylalkyl group, a $C_3$–$C_6$ alkynylalkyl or a $C_3$–$C_6$ haloalkenylalkyl group, and preferred is a $C_1$–$C_4$ alkyl group. Specific examples of the $C_1$–$C_4$ alkyl group, the $C_1$–$C_4$ haloalkyl group and the $C_3$–$C_4$ cycloalkyl group are as described concerning $R^1$, $R^2$ or Y. The $C_1$–$C_4$ alkyl group is specifically preferably methyl or ethyl. Specific examples of the $C_3$–$C_6$ alkenylalkyl group include —CH$_2$—CH=CH$_2$, —CH$_2$CH=C(CH$_3$)$_2$, —CH$_2$C(CH$_3$)=CH$_2$ and —CH$_2$—CH=CH—C$_2$H$_5$. Specific examples of the $C_3$–$C_6$ alkynylalkyl group include CH2—C≡CH, —CH$_2$—≡C—C$_2$H$_5$ and —CH(CH$_3$)—C≡CH. The $C_3$–$C_6$ haloalkenylalkyl group is a group in which at least one hydrogen atom of the $C_3$–$C_6$ alkenylalkyl group is replaced with a halogen atom (e.g., a chlorine atom, a fluorine atom, a bromine atom or an iodine atom), and examples thereof include —CH$_2$—CH=CHCl, —CH$_2$—CCl=CH$_2$, —CH$_2$—CF=CH$_2$, —CH$_2$CCl=CHCl, —CH$_2$CF=CHF, and —CH$_2$CCl=CH—CH$_3$. Preferred embodiments of Z including the above $R^{11}$ are as follows.

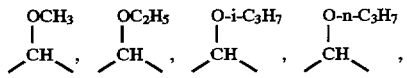

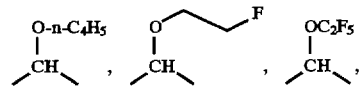

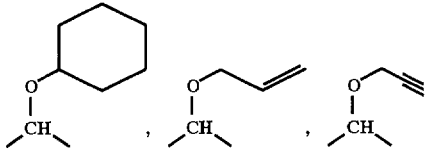

and

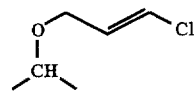

The pyrazole derivative in which z is

has the following general formula (Ib).

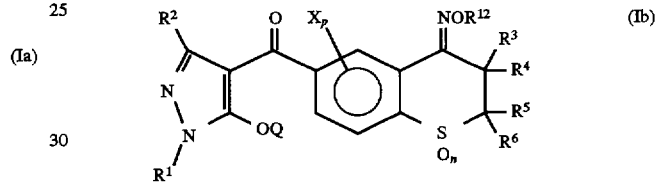

In the general formula (Ib), $R^{12}$ is a $C_1$–$C_4$ alkyl group, a $C_1$–$C_4$ haloalkyl group, a $C_3$–$C_6$ cycloalkyl group, a $C_3$–$C_6$ alkenylalkyl group, a $C_3$–$C_6$ alkynylalkyl group or a $C_3$–$C_6$ haloalkenylalkyl group, and a $C_1$–$C_4$ alkyl group is preferred. Specific examples of the $C_1$–$C_4$ alkyl group, the $C_1$–$C_4$ haloalkyl group, the $C_3$–$C_6$ cycloalkyl group, the $C_3$–$C_6$ alkenylalkyl group, the $C_3$–$C_6$ alkynylalkyl group and the $C_3$–$C_6$ haloalkenylalkyl group are as described concerning $R^1$, $R^2$, Y or $R^{11}$. The $C_1$–$C_4$ alkyl group is specifically preferably methyl. Preferred embodiments of Z including $R^{12}$ are as follows.

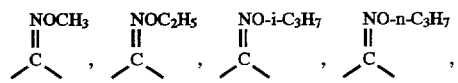

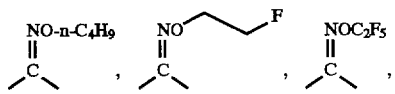

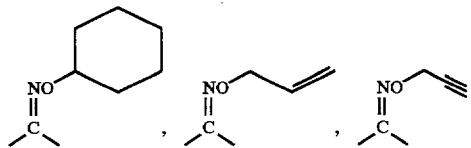

and

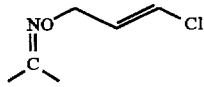

The pyrazole derivative in which Z is

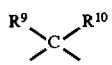

has the following general formula (Ic).

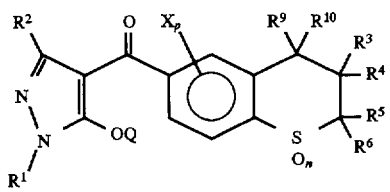

In the general formula (Ic), $R^9$ is a hydrogen atom, a $C_1$-$C_4$ alkyl group or a $C_1$-$C_4$ haloalkyl group, and $R^{10}$ is a hydrogen atom, a $C_1$-$C_4$ alkyl group, a $C_2$-$C_4$ alkenyl group or a $C_2$-$C_4$ alkynyl group. Each of these is independently preferably a hydrogen atom or a $C_1$-$C_4$ alkyl group. Preferred embodiments of Z including the above $R^9$ and $R^{10}$ are as follows.

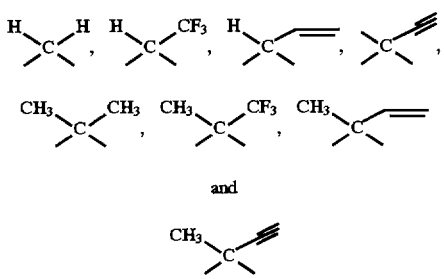

The pyrazole derivative of the general formula (I) in which Q is a hydrogen atom includes the following three tautomers, and all of these are included in the pyrazole derivative of the present invention.

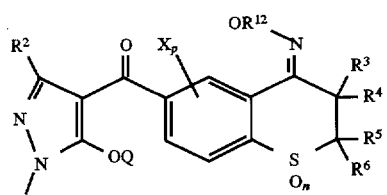

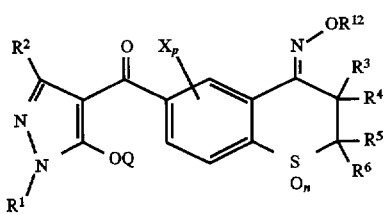

Some of pyrazole derivatives of the general formula (I) have asymmetric carbon, and include a variety of isomers, and the pyrazole derivative of the present invention includes all of such isomers or mixtures of isomers.

Further, the pyrazole derivative of the general formula (I) in which Q is a hydrogen atom is acidic, and can be easily converted to a salt by treating it with a base. This salt is also included in the pyrazole derivative of the present invention.

As the above base, any known base may be used without any special limitation. Examples thereof include organic bases such as amines and anilines and inorganic bases such as a sodium compound and a potassium compound. The amines include monoalkylamine, dialkylamine and trialkylamine. The alkyl group of each of the alkylamines is generally a $C_1$-$C_4$ alkyl group. The anilines include aniline, monoalkylaniline and dialkylaniline. The alkyl group of each of the alkylanilines is generally a $C_1$-$C_4$ alkyl group. The sodium compound includes sodium hydroxide and sodium carbonate. The potassium compound includes potassium hydroxide and sodium carbonate.

Preferably, specific examples, chemical names and structural formulae of pyrazole derivatives of the general formula (Ia) are as follows.

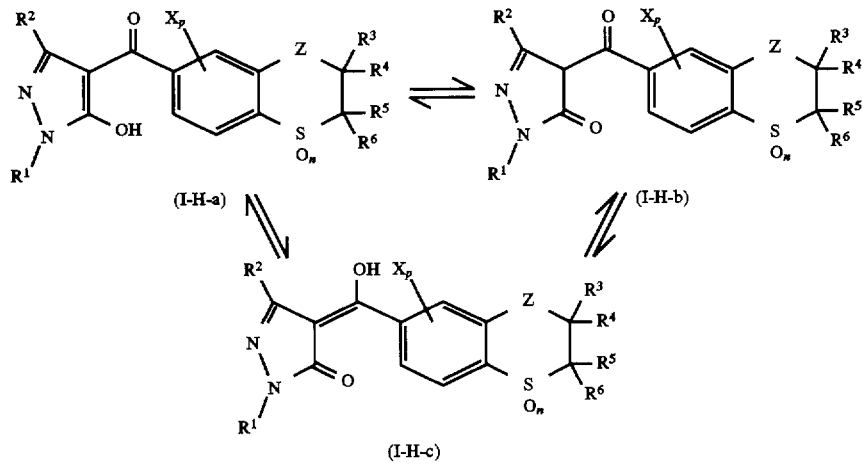

Further, the above pyrazole derivative (Ic) includes the following two geometrical isomers, and both of these are included in the pyrazole derivative of the present invention.

Compound(Ia-1)

4-methoxy-5-methyl-6-(1-ethyl-5-hydroxypyrazol-4-yl)carbonylthiochroman-1,1-dioxide

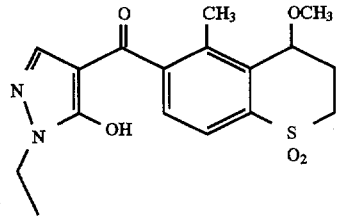

(In the general formula (Ia), $R^1=C_2H_5$, $R^2=H$, $R^3=R^4=R^5=R^6=H$, X=5-$CH_3$, $R^{11}=CH_3$, Q=H, n=2, p=1)

Compound(Ia-2)

4-ethoxy-5-methyl-6-(1-ethyl-5-n-propanesulfonyloxypyrazol-4-yl)carbonylthiochroman-1,1-dioxide

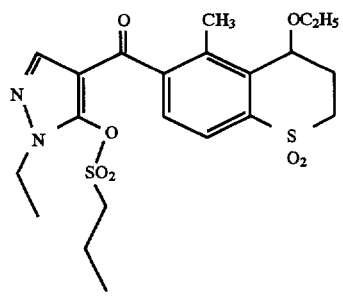

(In the general formula (Ia), $R^1=C_2H_5$, $R^2=H$, $R^3=R^4=R^5=R^6=H$, X=5-$CH_3$, $R^{11}=C_2H_5$, Q=$SO_2$—n—$C_3H_7$, n=2, p=1)

Compound(Ia-3)

4-methoxy-5,8-dimethyl-6-(1-ethyl-5-n-propanesulfonyloxypyrazol-4-yl)carbonylthiochroman-1,1-dioxide

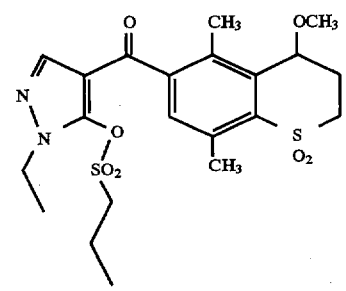

(In the general formula (Ia), $R^1=C_2H_5$, $R^2=H$, $R^3=R^4=R^5=R^6=H$, X=5, 8-$CH_3$, $R^{11}=CH_3$, Q=$SO_2$—n—$C_3H_7$, n=2, p=2)

Compound(Ia-4)

4-methoxy-5,8-dimethyl-6-(1-ethyl-5-i-butanesulfonyloxypyrazol-4-yl)carbonylthiochroman-1,1-dioxide

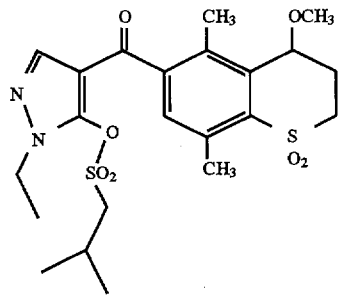

(In the general formula (Ia), $R^1=C_2H_5$, $R^2=H$, $R^3=R^4=R^5=R^6=H$, X=5, 8-$CH_3$, $R^{11}=CH_3$, Q=$SO_2$—i—$C_4H_9$, n=2, p=2)

Compound(Ia-5)

4-methoxy-5,8-dimethyl-6-(1-ethyl-5-p-toluenesulfonyloxypyrazol-4-yl)carbonylthiochroman-1,1-dioxide

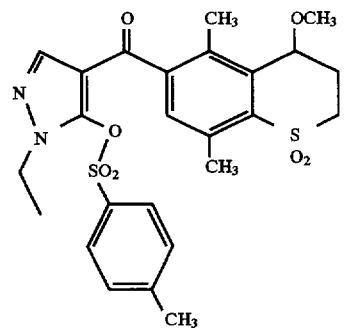

(In the general formula (Ia), $R^1=C_2H_5$, $R^2=H$, $R^3=R^4=R^5=R^6=H$, X=5, 8-$CH_3$, $R^{11}=CH_3$, Q=$SO_2$—$C_6H_4$—$CH_3$, n=2, p=2)

Compound(Ia-6)

4-methoxy-5,8-dimethyl-6-(1-ethyl-5-(2,5-dichlorophenyl)sulfonyloxypyrazol-4-yl)carbonylthiochroman-1,1-dioxide

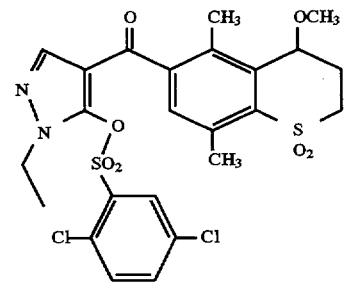

(In the general formula (Ia), $R^1=C_2H_5$, $R^2=H$, $R^3=R^4=R^5=R^6=H$, X=5, 8-$CH_3$, $R^{11}=CH_3$, Q=$SO_2$—$C_6H_3$—$Cl_2$, n=2, p=2)

Compound(Ia-7)

4-methoxy-5-methyl-6-(1-ethyl-5-cyclohexanecarbonyloxypyrazol-4-yl)carbonylthiochroman-1,1-dioxide

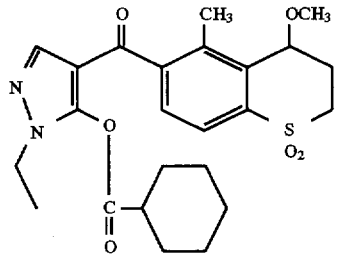

(In the general formula (Ia), $R^1=C_2H_5$, $R^2=H$, $R^3=R^4=R^5=R^6=H$, X=5-$CH_3$, $R^{11}=CH_3$, Q=—CO—cyclo—$C_6H_{11}$, n=2, p=1)

Preferably, specific examples, chemical names and structural formulae of pyrazole derivative of the general formula (Ib) are as follows.

Compound(Ib-1)

4-methoxyimino-5-methyl-6-(1-ethyl-5-n-propanesulfonyloxypyrazol-4-yl)carbonylthiochroman-1,1-dioxide

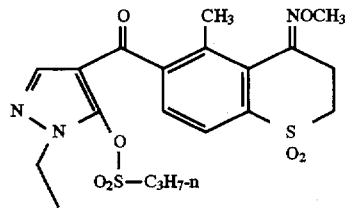

(In the general formula (Ib), $R^1=C_2H_5$, $R^2=H$, $R^3=R^4=R^5=R^6=H$, X=5-$CH_3$, $R^{12}=CH_3$, Q=—$SO_2$—n—$C_3H_7$, n=2, p=1)

Compound(Ib-2)

4-methoxyimino-5-methyl-6-(1-ethyl-5-phenacyloxypyrazol-4-yl)carbonylthiochroman-1,1-dioxide

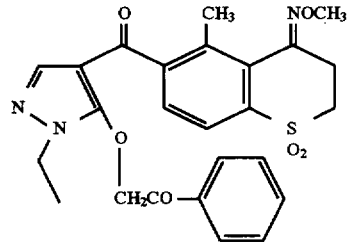

(In the general formula (Ib), $R^1=C_2H_5$, $R^2=H$, $R^3=R^4=R^5=R^6=H$, X=5-$CH_3$, $R^{12}=CH_3$, Q=—$CH_2CO$—$C_6H_5$, n=2, p=1)

Compound(Ib-3)

4-methoxyimino-5-methyl-6-(1-ethyl-5-p-toluenesulfonyloxypyrazol-4-yl)carbonylthiochroman-1,1-dioxide

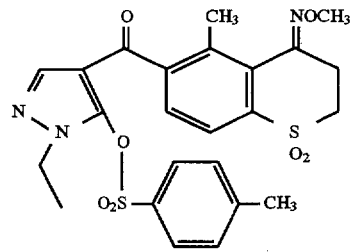

(In the general formula (Ib), $R^1=C_2H_5$, $R^2=H$, $R^3=R^4=R^5=R^6=H$, X=5-$CH_3$, $R^{12}=CH_3$, Q=—$SO_2$—$C_6H_4$—$CH_3$, n=2, p=1)

Compound(Ib-4)

4-methoxyimino-5-methyl-6-(1-ethyl-5-methanesulfonyloxypyrazol-4-yl)carbonylthiochroman-1,1-dioxide

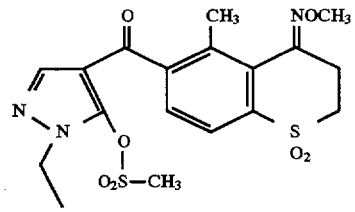

(In the general formula (Ib), $R^1=C_2H_5$, $R^2=H$, $R^3=R^4=R^5=R^6=H$, X=5-$CH_3$, $R^{12}=CH_3$, Q=—$SO_2$—$CH_3$, n=2, p=1)

Compound(Ib-5)

4-methoxyimino-5-methyl-6-(1-ethyl-5-ethanesulfonyloxypyrazol-4-yl)carbonylthiochroman-1,1-dioxide

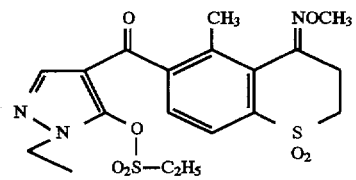

(In the general formula (Ib), $R^1=C_2H_5$, $R^2=H$, $R^3=R^4=R^5=R^6=H$, X=5-$CH_3$, $R^{12}=CH_3$, Q=—$SO_2$—$C_2H_5$, n=2, p=1)

Compound(Ib-6)

4-methoxyimino-5-methyl-6-(1-ethyl-5-n-butanesulfonyloxypyrazol-4-yl)carbonylthiochroman-1,1-dioxide

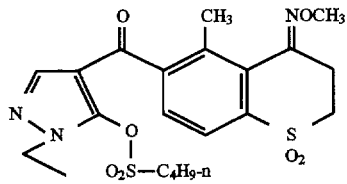

(In the general formula (Ib), $R^1=C_2H_5$, $R^2=H$, $R^3=R^4=R^5=R^6=H$, X=5-CH$_3$, $R^{12}=CH_3$, Q=—SO$_2$—n=C$_4$H$_9$, n=2, p=1)

Compound(Ib-7)

4-methoxyimino-5-methyl-6-(1-ethyl-5-n-octanesulfonyloxypyrazol-4-yl)carbonylthiochroman-1,1-dioxide

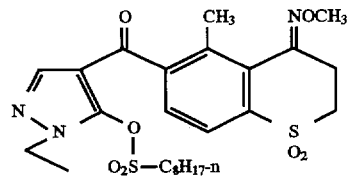

(In the general formula (Ib), $R^1=C_2H_5$, $R_2=H$, $R^3=R^4=R^5=R^6=H$, X=5-CH$_3$, $R^{12}=CH_3$, Q=—SO$_2$—n—C$_8$H$_{17}$, n=2, p=1)

Compound(Ib-8)

4-methoxyimino-5-methyl-6-(1-ethyl-5-(2-methylphenyl)sulfonyloxypyrazol-4-yl)carbonylthiochroman-1,1-dioxide

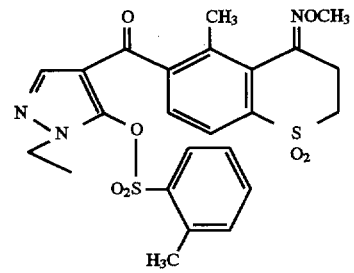

(In the general formula (Ib), $R^1=C_2H_5$, $R^2=H$, $R^3=R^4=R^5=R^6=H$, X=5-CH$_3$, $R^{12}=CH_3$, Q=—SO$_2$—C$_6$H$_4$—CH$_3$, n=2, p=1)

Compound(Ib-9)

4-methoxyimino-5-methyl-6-(1-ethyl-5-(2-nitrophenyl)sulfonyloxypyrazol-4-yl)carbonylthiochroman-1,1-dioxide

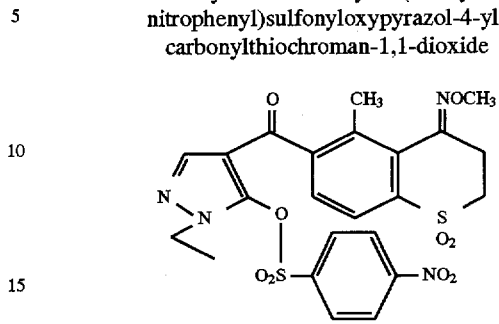

(In the general formula (Ib), $R^1=C_2H_5$, $R^2=H$, $R^3=R^4=R^5=R^6=H$, X=5-CH$_3$, $R^{12}=CH_3$, Q=—SO$_2$—C$_6$H$_4$—NO$_2$, n=2, p=1)

Compound(Ib-10)

4-methoxyimino-5-methyl-6-(1-ethyl-5-(4-methoxyphenyl)sulfonyloxypyrazol-4-yl)carbonylthiochroman-1,1-dioxide

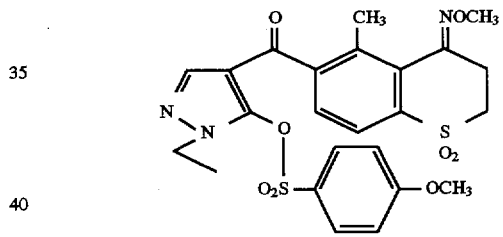

(In the general formula (Ib), $R^1=C_2H_5$, $R^2=H$, $R^3=R^4=R^5=R^6=H$, X=5-CH$_3$, $R^{12}=CH_3$, Q=—SO$_2$—C$_6$H$_4$—OCH$_3$, n=2, p=1)

Compound(Ib-11)

5,8-dimethyl-4-methoxyimino-(1-ethyl-5-i-propanesulfonyloxypyrazol-4-yl)carbonylthiochroman-1,1-dioxide

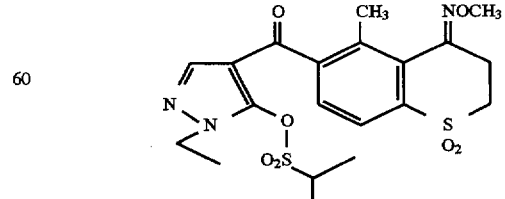

(In the general formula (Ib), R¹=C₂H₅, R²=H, R³=R⁴=R⁵=R⁶=H, X=5, 8-CH₃, R¹²=CH₃, Q=—SO₂—i—C₃H₇, n=2, p=2)

Compound(Ib-12)

5,8-dimethyl-4-methoxyimino-(1-ethyl-5-n-butanesulfonyloxypyrazol-4-yl)carbonylthiochroman-1,1-dioxide

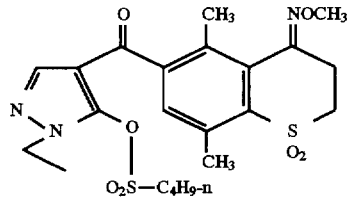

(In the general formula (Ib), R¹=C₂H₅, R²=H, R₃=R⁴=R⁵=R⁶=H, X=5, 8-CH₃, R¹²=CH₃, Q=—SO₂—n—C₄H₉, n=2, p=2)

Compound(Ib-13)

5,8-dimethyl-4-methoxyimino-(1-ethyl-5-phenylsulfonyloxypyrazol-4-yl)carbonylthiochroman-1,1-dioxide

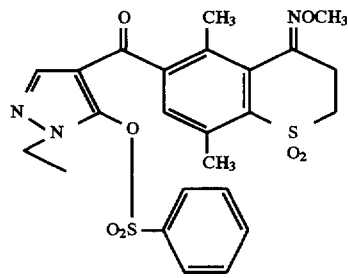

(In the general formula (Ib), R¹=C²H⁵, R²=H, R³=R⁴=R⁵=R⁶=H, X=5, 8-CH₃, R¹²=CH₃, Q=—SO₂—C₆H₅, n=2, p=2)

Compound(Ib-14)

5,8-dimethyl-4-methoxyimino-(1-ethyl-5-(4-chlorophenyl)sulfonyloxypyrazol-4-yl)carbonylthiochroman-1,1-dioxide

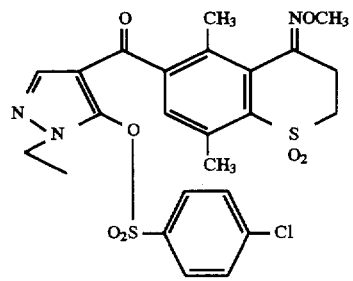

(In the general formula (Ib), R¹=C₂H₅, R²=H, R³=R⁴=R⁵=R⁶=H, X=5, 8-CH₃, R¹²=CH₃, Q=—SO₂—C₆H₄—Cl, n=2, p=2)

Compound(Ib-15)

5,8-dimethyl-4-methoxyimino-(1-ethyl-5-(4-fluorophenyl)sulfonyloxypyrazol-4-yl)carbonylthiochroman-1,1-dioxide

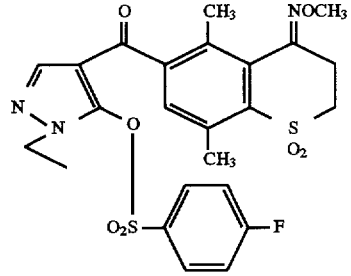

(In the general formula (Ib), R¹=C₂H₅, R²=H, R³=R⁴=R⁵=R⁶=H, X=5, 8-CH₃, R¹²=CH₃, Q=—SO₂—C₆H₄—F, n=2, p=2)

Compound(Ib-16)

5,8-dimethyl-4-methoxyimino-(1-ethyl-5-(3,4-difluorophenyl)sulfonyloxypyrazol-4-yl)carbonylthiochroman-1,1-dioxide

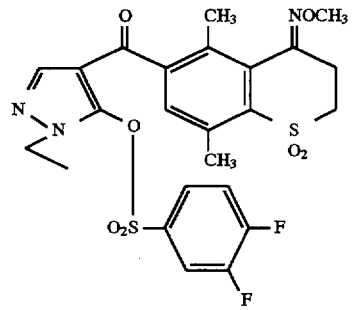

(In the general formula (Ib), R¹=C₂H₅, R²=H, R³=R⁴=R⁵=R⁶=H, X=5, 8-CH₃, R¹²=CH₃, Q=—SO₂—C₆H₃—F₂, n=2, p=2)

Compound(Ib-17)

5,8-dimethyl -4-methoxyimino-(1,3-dimethyl -5-n-propanesulfonyloxypyrazol-4-yl)carbonylthiochroman-1,1-dioxide

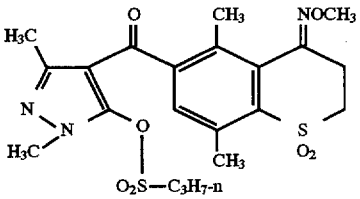

(In the general formula (Ib), $R^1$=CH$_3$, $R^2$=CH$_3$, $R^3$=$R^4$=$R^5$=$R^6$=H, X=5, 8-CH$_3$, $R^{12}$=CH$_3$, Q=—SO$_2$—n—C$_3$H$_7$, n=2, p=2)

Compound(Ib-18)

4-methoxyimino-5-methyl-(1,3-dimethyl-5-p-toluensulfonyloxypyrazol-4-yl)carbonylthiochroman-1,1-dioxide

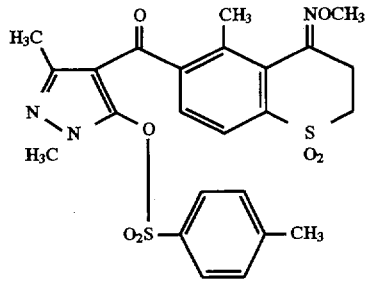

(In the general formula (Ib), $R^1$=CH$_3$, $R^2$=CH$_3$, $R^3$=$R^4$=$R^5$=$R^6$=H, X=5-CH$_3$, $R^{12}$=CH$_3$, Q=—SO$_2$—C$_6$H$_4$—CH$_3$, n=2, p=1)

Compound(Ib-19)

4-methoxyimino-5-methyl-6-(1-ethyl-5-acetyloxypyrazol-4-yl)carbonylthiochroman-1,1-dioxide

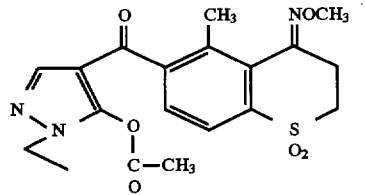

(In the general formula (Ib), $R^1$=C$_2$H$_5$, $R^2$=H, $R^3$=$R^4$=$R^5$=$R^6$=H, X=5-CH$_3$, $R^{12}$=CH$_3$, Q=—CO—CH$_3$, n=2, p=1)

Compound(Ib-20)

4-methoxyimino-5-metyl-6-(1-ethyl-5-ethanecarbonyloxypyrazol-4-yl)carbonylthiochroman-1,1-dioxide

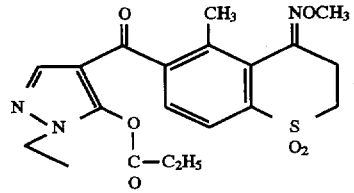

(In the general formula (Ib), $R^1$=C$_2$H$_5$, $R^2$=H, $R^3$=$R^4$=$R^5$=$R^6$=H, X=5-CH$_3$, $R^{12}$=CH$_3$, Q=—CO—C$_2$H$_5$, n=2, p=1)

Compound(Ib-21)

4-methoxyimino-5-metyl-6-(1-ethyl-5-n-propanecarbonyloxypyrazol-4-yl)carbonylthiochroman-1,1-dioxide

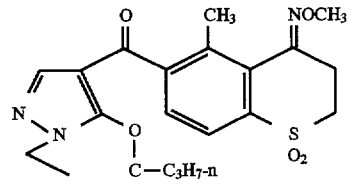

(In the general formula (Ib), $R^1$=C$_2$H$_5$, $R^2$=H, $R^3$=$R^4$=$R^5$=$R^6$=H, X=5-CH$_3$, $R^{12}$=CH$_3$, Q=—CO—n—C$_3$H$_7$, n=2, p=1)

Compound(Ib-22)

4-methoxyimino-5-metyl-6-(1-ethyl-5-n-butanecarbonyloxypyrazol-4-yl)carbonylthiochroman-1,1-dioxide

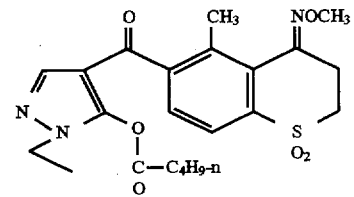

(In the general formula (Ib), $R^1$=C$_2$H$_5$, $R^2$=H, $R^3$=$R^4$=$R^5$=$R^6$=H, X=5-CH$_3$, $R^{12}$=CH$_3$, Q=—CO—n—C$_4$H$_9$, n=2, p=1)

Compound(Ib-23)

4-methoxyimino-5-metyl-6-(1-ethyl-5-n-hexanecarbonyloxypyrazol-4-yl)carbonylthiochroman-1,1-dioxide

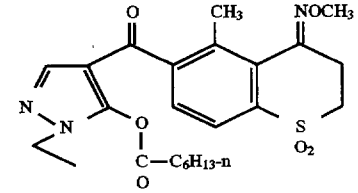

(In the general formula (Ib), $R^1$=C$_2$H$_5$, $R^2$=H, $R^3$=$R^4$=$R^5$=$R^6$=H, X=5-CH$_3$, $R^{12}$=CH$_3$, Q=—CO—n—C$_6$H$_{13}$, n=2, p=1)

Compound(Ib-24)

5,8-dimethyl-4-methoxyimino-6-(1-ethyl-5-n-propanecarbonyloxypyrazol-4-yl)carbonylthiochroman-1,1-dioxide

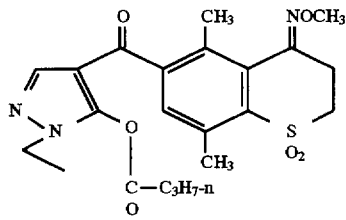

(In the general formula (Ib), $R^1=C_2H_5$, $R^2=H$, $R^3=R^4=R^5=R^6=H$, X=5, 8-$CH_3$, $R^{12}=CH_3$, Q=—CO—n—$C_3H_7$, n=2, p=2)

Compound(Ib-25)

4-methoxyimino-5-methyl-6-(1-ethyl-5-acetylmethyleneoxypyrazol-4-yl)carbonylthiochroman-1,1-dioxide

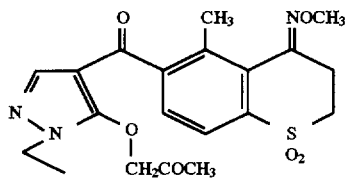

(In the general formula (Ib), $R^1=C_2H_5$, $R^2=H$, $R^3=R^4=R^5=R^6=H$, X=5-$CH_3$, $R^{12}$=CH3, Q=—$CH_2$—$COCH_3$, n=2, p=1)

Compound(Ib-26)

5,8-dimethyl-4-methoxyimino-6-(1-ethyl-5-phenacyloxypyrazol-4yl)carbonylthiochroman-1,1-dioxide

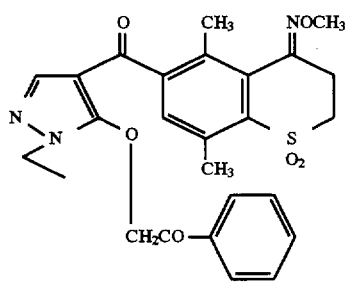

(In the general formula (Ib), $R^1=C_2H_5$, $R^2=H$, $R^3=R^4=R^5=R^6=H$, X=5, 8-$CH_3$, $R^{12}=CH_3$, Q=$CH_2CO$—$C_6H_5$, n=2, p=2)

Compound(Ib-27)

5,8-dimethyl-4-methoxyimino-6-(1-ethyl-5-benzyloxypyrazol-4-yl)carbonylthiochroman-1,1-dioxide

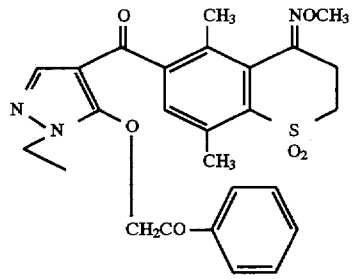

(In the general formula (Ib), $R^1=C_2H_5$, $R^2=H$, $R^3=R^4=R^5=R^6=H$, X=5, 8-$CH_3$, $R^{12}=CH_3$, Q=$CH_2$—$C_6H_5$, n=2, p=2)

Preferably, specific examples, chemical names and structural formulae of pyrazole derivative of the general formula (Ic) are as follows.

Compound(Ic-1)

4,4,5,8-tetramethyl-6-(1-ethyl-5-hydroxylpyrazol-4-yl)carbonylthiochroman-1,1-dioxide

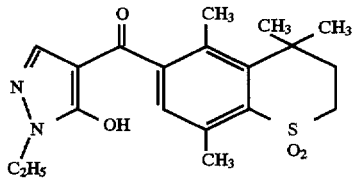

(In the general formula (Ic), $R^1=C_2H_5$, $R^2=H$, $R^3=R^4=R^5=R^6=H$, X=5, 8-$CH_3$, $R^9=R^{10}=CH_3$, Q=H, n=2, p=2)

Compound(Ic-2)

4,4,5,8-tetramethyl-6-(1-ethyl-5-ethanesulfonyloxypyrazol-4-yl)carbonylthiochroman-1,1-dioxide

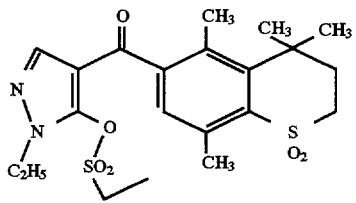

(In the general formula (Ic), $R^1=C_2H_5$, $R^2=H$, $R^3=R^4=R^5=R^6=H$, X=5, 8-$CH_3$, $R^9=R^{10}CH_3$, Q=—$SO_2$—$C_2H_5$, n=2, p=2)

Compound(Ic-3)

4,4,5,8-tetramethyl-6-(1-ethyl-5-n-propanesulfonyloxypyrazol-4-yl)carbonylthiochroman-1,1-dioxide

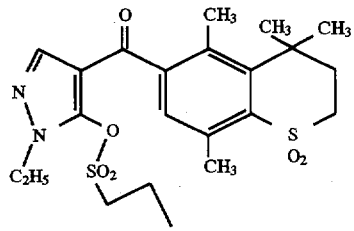

(In the general formula (Ic), $R^1=C_2H_5$, $R^2=H$, $R^3=R^4=R^5=R^6=H$, X=5, 8-$CH_3$, $R^9=R^{10}CH_3$, Q=—$SO_2$—n—$C_3H_7$, n=2, p=2)

Compound(Ic-4)

4,4,5,8-tetramethyl-6-(1-ethyl-5-n-butanesulfonyloxypyrazol-4-yl)carbonylthiochroman-1,1-dioxide

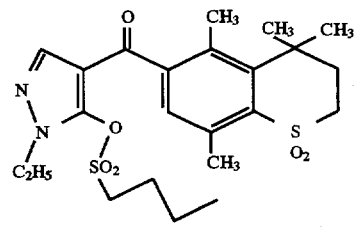

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—n—$C_4H_9$, n=2, p=2)

Compound(Ic-5)

4,4,5,8-tetramethyl-6-(1-ethyl-5-n-octanesulfonyloxypyrazol-4-yl)carbonylthiochroman-1,1-dioxide

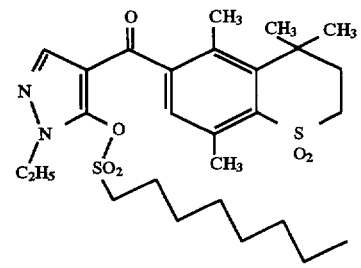

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_8H_{17}$, n=2, p=2)

Compound(Ic-6)

4,4,5,8-tetramethyl-6-(1-ethyl-5-p-toluenesulfonyloxypyrazol-4-yl)carbonylthiochroman-1,1-dioxide

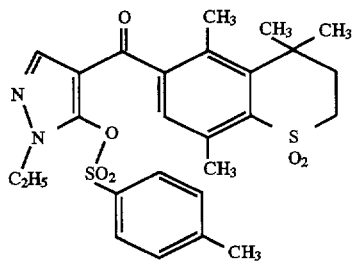

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_6H_4$—$CH_3$, n=2, p=2)

Compound(Ic-7)

4,4,5,8-tetramethyl-6-(1-ethyl-5-(4-methoxyphenyl)sulfonyloxypyrazol-4-yl)carbonylthiochroman-1,1-dioxide

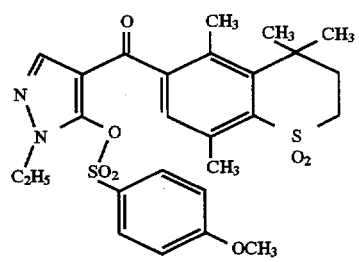

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_6H_4$—$OCH_3$, n=2, p=2)

Compound(Ic-8)

4,4,5,8-tetramethyl-6-(1-ethyl-5-(4-nitrophenyl)sulfonyloxypyrazol-4-yl)carbonylthiochroman-1,1-dioxide

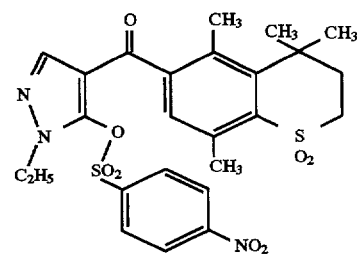

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_6H_4$—$NO_2$, n=2, p=2)

Compound(Ic-9)

4,4,5,8-tetramethyl-6-(1-ethyl-5-p-chlorophenylsulfonyloxypyrazol-4-yl)carbonylthiochroman-1,1-dioxide

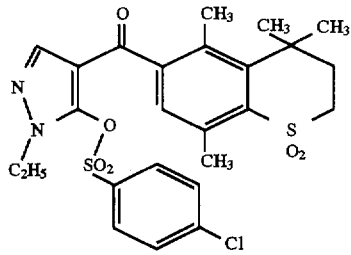

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_6H_4$—Cl, n=2, p=2)

Compound(Ic-10)

4,4,5,8-tetramethyl-6-(1-ethyl-5-(2-methylphenyl)sulfonyloxypyrazol-4-yl)carbonylthiochroman-1,1-dioxide

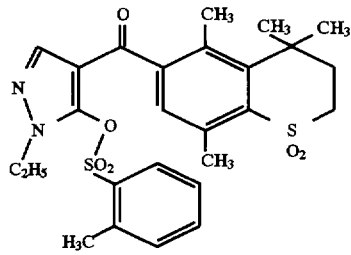

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_6H_4$—$CH_3$, n=2, p=2)

Compound(Ic-11)

4,4,5,8-tetramethyl-6-(1-ethyl-5-(2,4-dichlorophenyl)sulfonyloxypyrazol-4-yl)carbonylthiochroman-1,1-dioxide

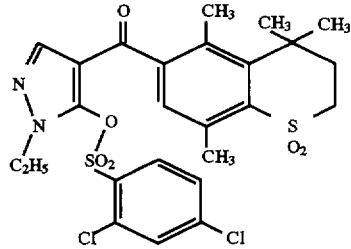

(In the general formula (Ic), $R^1=C_2H_5$, $R^2=H$, $R^3=R^4=R^5=R^6=H$, X=5, 8-$CH_3$, $R^9=R^{10}=CH_3$, Q=—$SO_2$—$C_6H_3$—$Cl_2$, n=2, p=2)

Compound(Ic-12)

4,4,5,8-tetramethyl-6-(1-ethyl-5-ethanecarbonyloxypyrazol-4-yl)carbonylthiochroman-1,1-dioxide

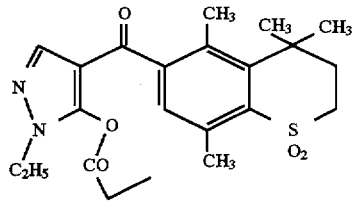

(In the general formula (Ic), $R^1=C_2H_5$, $R^2=H$, $R^3=R^4=R^5=R^6=H$, X=5, 8-$CH_3$, $R^9=R^{10}=CH_3$, Q=—CO—$C_2H_5$, n=2, p=2)

Compound(Ic-13)

4,4,5,8-tetramethyl-6-(1-ethyl-5-n-butanecarbonyloxypyrazol-4-yl)carbonylthiochroman-1,1-dioxide

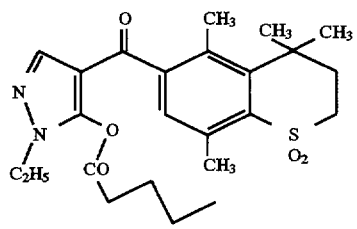

(In the general formula (Ic), $R^1=C_2H_5$, $R^2=H$, $R^3=R^4=R^5=R^{6=H}$, X=5, 8-$CH_3$, $R^9=R^{10}=CH_3$, Q=—CO—n—$C_4H_9$, n=2, p=2)

Compound(Ic-14)

4,4,5,8-tetramethyl-6-(1-ethyl-5-n-hexanecarbonyloxypyrazol-4-yl)carbonylthiochroman-1,1-dioxide

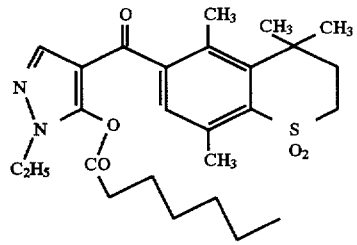

(In the general formula (Ic), $R^1=C_2H_5$, $R^2H$, $R^3=R^4=R^5=R^{6=H}$, X=5, 8-$CH_3$, $R^9=R^{10}=CH_3$, Q=—CO—n—$C_6H_{13}$, n=2, p=2)

Compound(Ic-15)

4,4,5,8-tetramethyl-6-(1-ethyl-5-cyclohexanecarbonyloxypyrazol-4-yl)carbonylthiochroman-1,1-dioxide

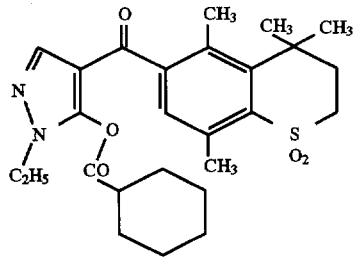

(In the general formula (Ic), $R^1=C_2H_5$, $R^2=H$, $R^3=R^4=R^5=R^{6=H}$, $^{X=}5$, 8-$CH_3$, $R^9=R^{10}=CH_3$, Q=—CO—cyclo-$C_6H_{11}$, n=2, p=2)

Compound(Ic-16)

4,4,5,8-tetramethyl-6-(1-ethyl-5-(2,4-dichlorophenyl)carbonyloxypyrazol-4-yl)carbonylthiochroman-1,1-dioxide

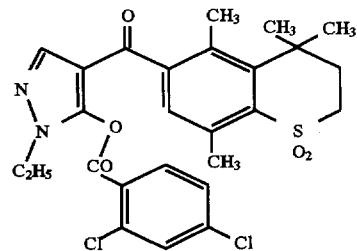

(In the general formula (Ic), $R^1=C_2H_5$, $R^2=H$, $R^3=R^4=R^5=R^{6=H}$, $^{X=}5$, 8-$CH_3$, $R^9=R^{10}=CH_3$, Q=—CO—$C_6H_4$—$Cl_2$, n=2, p=2)

Compound(Ic-17)

4,4,5,8-tetramethyl-6-(1-ethyl-5-phenacyloxypyrazol-4-yl)carbonylthiochroman-1,1-dioxide

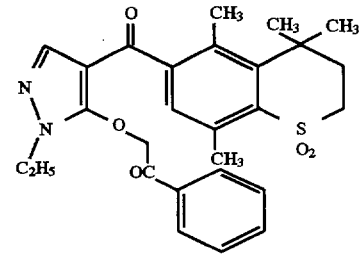

(In the general formula (Ic), $R^1=C_2H_5$, $R^2=H$, $R^3=R^4=R^5=R^{6=H}$, $^{X=}5$, 8-$CH_3$, $R^9=R^{10}=CH_3$, Q=—CO—$C_6H_5$, n=2, p=2)

Compound(Ic-18)

4,4,5,8-tetramethyl-(1,3-dimethyl-5-hydroxypyrazol-4-yl)carbonylthiochroman-1,1-dioxide

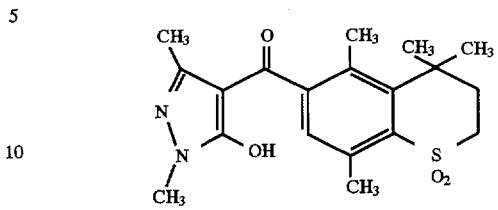

(In the general formula (Ic), $R^1=CH_3$, $R^2=CH_3$, $R^3=R^4=R^5=R^{6=H}$, $^{X=}5$, 8-$CH_3$, $R^9=R^{10}=CH_3$, Q=H, n=2, p=2)

Compound(Ic-19)

4,4,5-trimethyl-(1-ethyl-5-hydroxypyrazol-4-yl)carbonylthiochroman-1,1-dioxide

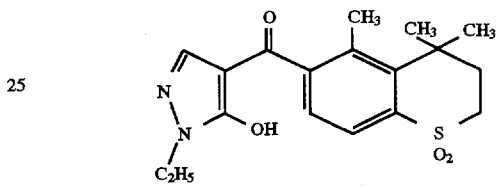

(In the general formula (Ic), $R^1=C_2H_5$, $R^2=H$, $R^3=R^4=R^5=R^{6=H}$, $^{X=}5$-$CH_3$, $R^9=R^{10}=CH_3$, Q=H, n=2, p=1)

Compound(Ic-20)

5,8-dichloro-4,4-dimethyl-(1-ethyl-5-hydroxypyrazol-4-yl)carbonylthiochroman-1,1-dioxide

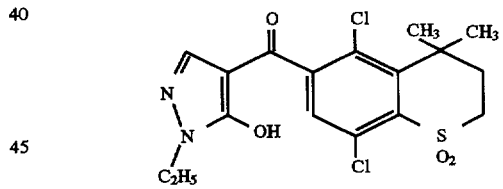

(In the general formula (Ic), $R^1=C_2H_5$, $R^2=H$, $R^3=R^4=R^5=R^{6=H}$, $^{X=}5$, 8-Cl, $R^9=R^{10}=CH_3$, Q=H, n=2, p=2)

Compound(Ic-21)

4,4,5,8-tetramethyl-6-(1-methyl-5-hydroxypyrazol-4-yl)carbonylthiochroman-1,1-dioxide

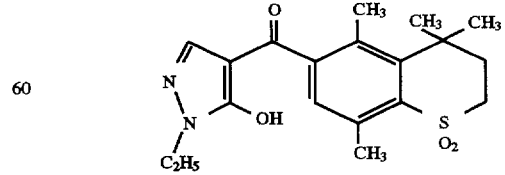

(In the general formula (Ic), $R^1=CH_3$, $R^2=H$, $R^3=R^4=R^5=R^{6=H}$, $^{X=}5$, 8-$CH_3$, $R^9=R^{10}=CH_3$, n=2, p=2)

Compound(Ic-22)

4,4,5,8-tetramethyl-6-(1-methyl-5-n-
propanesulfonyloxypyrazol-4-yl)
carbonylthiochroman-1,1-dioxide

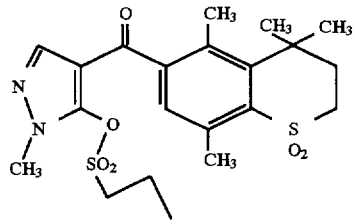

(In the general formula (Ic), $R^1=CH_3$, $R^2=H$, $R^3=R^4=R^5=R^{6=H}$, $X=5$, 8-$CH_3$, $R^9=R^{10}=CH_3$, Q=—$SO_2$—n—$C_3H_7$, n=2, p=2)

Compound(Ic-23)

4,4,5,8-tetramethyl-6-(1-methyl-5-p-
toluenesulfonyloxypyrazol-4-yl)
carbonylthiochroman-1,1-dioxide

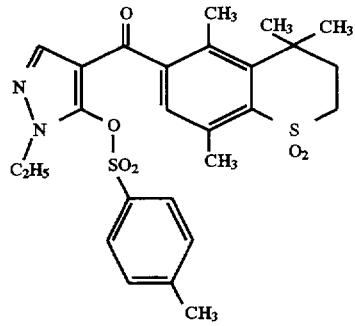

(In the general formula (Ic), $R^1=CH_3$, $R^2=H$, $R^3=R^4=R^5=R^{6=H}$, $X=5$, 8-$CH_3$, $R^9=R^{10}=CH_3$, Q=—$SO_2$—$C_6H_4$—$CH_3$, n=2, p=2)

Compound(I c-24)

4,4-dimethyl -(1,3-dimethyl-5-hydroxypyrazol 4-yl)
-carbonylthiochroman-1,1-dioxide

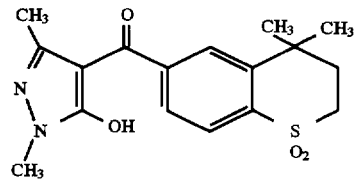

(In the general formula (Ic), $R^1=CH_3$, $R^2=CH_3$, $R^3=R^4=R^5=R^{6=H}$, $R^9=R^{10}=CH_3$, Q=H, n=2, p=0)

Compound(Ic-25)

4,4-dimethyl-(1-methyl-5-hydroxypyrazol-4-yl)-
carbonylthiochroman-1,1-dioxide

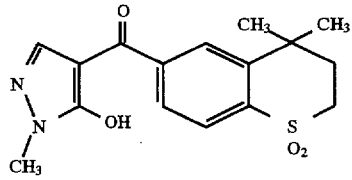

(In the general formula (Ic), $R^1=CH_3$, $R^2=H$, $R^3=R^4=R^5=R^{6=H}$, $R^9=R^{10}=CH_3$, Q=H, n=2, p=0)

Compound(Ic-25)

4,4-dimethyl-(1-ethyl-5-hydroxypyrazol-4-yl)-
carbonylthiochroman-1,1-dioxide

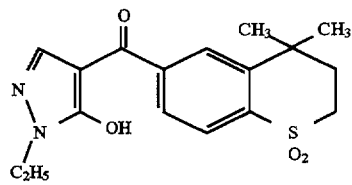

(In the general formula (Ic), $R^1=C_2H_5$, $R^2=H$, $R^3=R^4=R^5=R^{6=H}$, $R^9=R^{10}=CH_3$, Q=H, n=2, p=0)

Compound(Ic-27)

5-chloro-4,4,8-trimethyl-(1-ethyl-5-hydroxypyrazol-
4-yl)carbonylthiochroman-1,1-dioxide

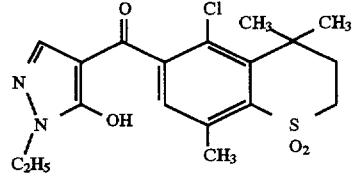

(In the general formula (Ic), $R^1=C_2H_5$, $R^2=H$, $R^3=R^4=R^5=R^{6=H}$, $X=$5-Cl, 8-$CH_3$, $R^9=R^{10}=CH_3$, Q=H, n=2, p=2)

In the herbicide composition of the present invention, the herbicide compound which is the second active ingredient can exhibit a synergistic effect when used with the above mentioned pyrazole derivative (I). Examples of this herbicide compound includes germination inhibitor such as chloroacetamide herbicide or dinitroaniline herbicide; plant hormone such as benzoic acid herbicide, pyridine carboxylic acid herbicide or phenoxy herbicide; ALS (Acetolactate Synthetase) inhibitor such as surfonylurea herbicide or imidazolinone herbicide; photosynthesis inhibitor such as triazine herbicide or urea herbicide; and other herbicide such as diazine herbicide, benzonitrile herbicide or pyridazine herbicide.

In the herbicide composition of the present invention, among the above mentioned herbicide compound, at least one member selected from the following groups is used as an active ingredient with the pyrazole derivative (I).

Chloroacetamide herbicide;

Imidazolinone herbicide;

Triazine herbicide such as Compound (B-1)~(B-3);

Compound(B-1)
  Common name: atrazine
  Chemical Name:

6-chloro-$N^2$-ethyl-$N^4$-isopropil-1,3,5-triazine-2,4-diamine

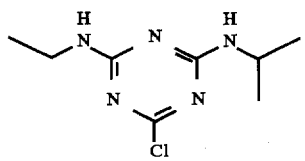

Compound(B-2)
  Common name: cyanazine
  Chemical Name:

2-(4-chloro-6-ethylamino-1,3,5-triazin-2-ylamino)-2-methylpropionitrile

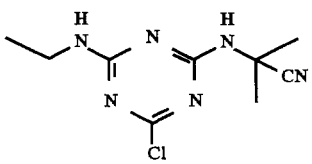

Compound(B-3)
  Common name: metribuzin
  Chemical Name:

4-amino-6-tert-buthyl-4,5-dihydro-3-methylthio-1,2,4-triazin-5-one

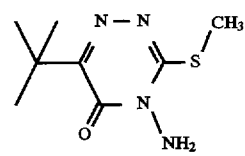

Urea herbicide such as Compounds (B-4) and (B-5);

Compound(B-4)
  Common name: linuron
  Chemical Name:
  3-(3,4-dichlorophenyl)-1-methoxy-1-methylurea

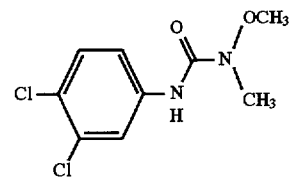

Compound(B-5)
  Common name: metbenzurone
  Chemical Name:

(±)-1-methoxy-3-[4-(2-methoxy-2,4,4-trimethylchroman-7-yloxy)phenyl]-1-methylurea

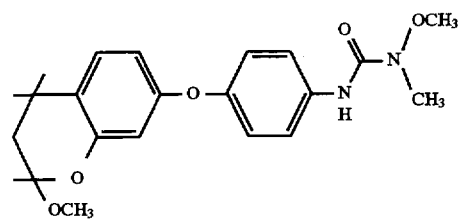

Diazine herbicide such as Compound (B-6);

Compound(B-6)
  Common name: bentazone
  Chemical Name:

3-isopropyl-1H-2,1,3-benzothiadiazin-4(3H)-one-2,2-dioxide

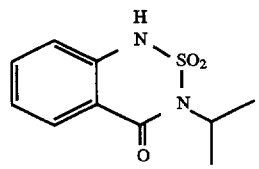

Benzoic acid herbicide such as Compound (B-7);

Compound(B-7)
  Common name: dicamba
  Chemical Name:

3,6-dichloro-2-methoxybenzoic acid

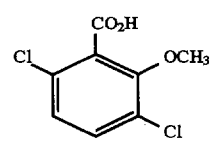

Pyridine carboxylic acid herbicide such as Compound (B-8);

Compound(B-8)
　Common name: chlopyralid
　Chemical Name:

3,6-dichloropyridine-2-carboxylic acid

Phenoxy herbicide such as Compound (B-9);
Compound(B-9)
　Common name: 2,4-D
　Chemical Name:

2-(2,4-dichlorophenoxy)acetic acid

Benzonitrile herbicide such as Compound (B-10);
Compound(B-10)
　Common name: bromoxynil
　Chemical Name:

3,5-dibromo-4-hydroxybenzonitrile

Dinitroaniline herbicide such as Compound (B-13);
Compound(B-13)
　Common name: pendimethalin
　Chemical Name:

N-(1-ethylpropyl)-2,6-dinitro-3,4-xylidine

Sulfonyl urea herbicide such as Compound (B-14), (B-15) and (B-17);

Compound(B-14)
　Common name: nicosulfuron
　Chemical Name:

2-(4,6-dimethoxypyrimidin-2-ylcarbamoylsulfamoyl)-N,N-dimethylnicotineamide

Compound(B-15)
　Common name: rimsulfuron
　Chemical Name:

1-(4,6-dimethoxypyrimidin-2-yl-3-(3-ethylsulfonyl-2-pyridylsulfonyl)urea

Compound(B-17)
　Common name: primisulfuron
　Chemical Name:

Methyl2-[4,6-bis(difluoromethoxy)pyrimidin-2-yl-carbamoylsulfamoyl]benzoic acid

Pyridazin herbicide such as Compound (B-20);
Compound(B-20)
  Common name: pyridate
  Chemical Name:

6-chloro-3-phenylpyridazin-4-yl-S-octylthiocarbonate

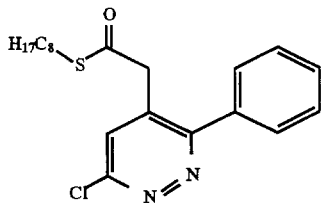

Among the herbicide compounds, the following Compounds (B-11), (B-12), (B-18) and (B-19) are exemplified as the chloroacetamide herbicide.

Compound(B-11)
  Common name: alachlor
  Chemical Name:

2-chloro-2',6'-diethyl-N-methoxymethylacetanilide

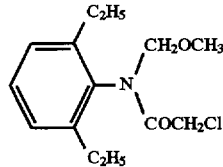

Compound(B-12)
  Common name: metolachlor
  Chemical Name:

2-chloro-N-(2-ethyl-6-methylphenyl)-N-(2-methoxy-1-methylethyl)acetamide

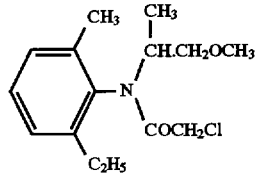

Compound(B-18)
  Common name: dimethenamid
  Chemical Name:

(1RS,aRS)-2-chloro-N-(2,4-dimethyl-3-thienyl)-N-(2-methoxy-1-methylethyl)acetamide

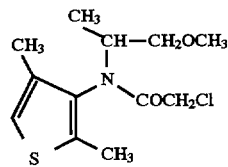

Compound(B-19)
  Common name: acetochlor
  Chemical Name:

2-chloro-2'-ethyl-6'-methyl-N-ethoxymethylacetanilide

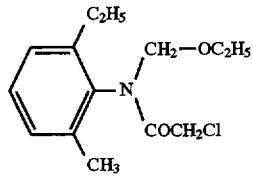

Among the herbicide compounds, the following Compounds (B-16) and (B-21) are exemplified as the imidazolinone herbicide.

Compound(B-16)
  Common name: imazethapyr
  Chemical Name:

5-ethyl-2-(4-isopropil-4-methyl-5-oxo-2-imidazolin-2-yl)nicotinic acid

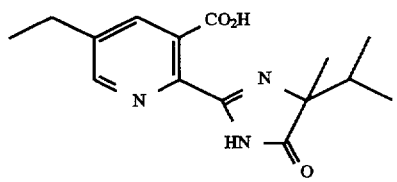

Compound(B-21)
  Common name: imazamethabenz-methyl
  Chemical Name:

Compound of a Methyl 6-(4-isopropyl-4-methyl-5-oxo-2-imidazolin-2-yl)-m-toluic acid and a Methyl 6-(4-isopropyl-4-methyl-5-oxo-2-imidazolin-2-yl)-p-toluic acid

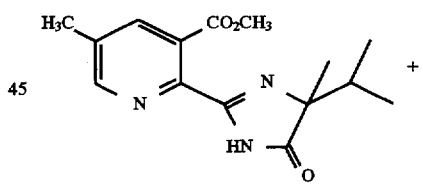

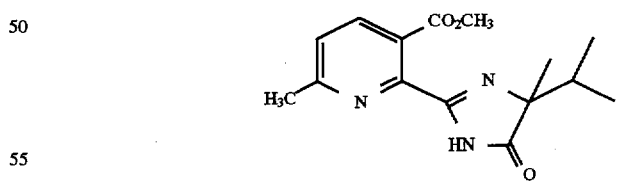

(Imazamethabenz-methyl which is a mixture of the two isomers is commercially available under a trade name of Assert.)

The herbicide composition of the present invention contains, as active ingredients, at least one of the above pyrazole derivatives (I) and at least one selected from a group of the above herbicide compounds. The mixing ratio of these is not specially limited, and a synergistic effect can be obtained in a broad range of the mixing ratio, while the pyrazole derivative (I) and the compounds (B-1)~(B-2) are generally preferably mixed in the following mixing ratios (weight ratios).

pyrazole derivative(I): compound(B-1:atrazine)=2:1~1:50
pyrazole derivative(I): compound(B-2:cyanazine)=2:1~1:50
pyrazole derivative(I): compound(B-3:metribuzin)= 3:1~1:25
pyrazole derivative(I): compound(B-4:linuron)=2:1~1:50
pyrazole derivative(I): compound(B-5:metbenzurone)= 1:2~1:100
pyrazole derivative(I): compound(B-6:bentazone)=6:1~1:00
pyrazole derivative(I): compound(B-7:dicamba)=1:1~1:50
pyrazole derivative(I): compound(B-8:chlopyralid)= 4:3~1:12
pyrazole derivative(I): compound(B-9:2,4-D)=2:1~1:5
pyrazole derivative(I): compound(B-10:bomoxynil)= 1:1~1:50
pyrazole derivative(I): compound(B-11:alachlor)=2:1~1:25
pyrazole derivative(I): compound(B-12:metolachlor)= 2:1~1:25
pyrazole derivative(I): compound(B-13:pendimethalin)= 2:1~1:25
pyrazole derivative(I): compound(B-14:nicosulfuron)= 1:3~40:1
pyrazole derivative(I): compound(B-15:rimsulfuron)= 1:3~40:1
pyrazole derivative(I): compound(B-16:imazethapyr)= 1:6~40:1
pyrazole derivative(I): compound(B-17:primisulfuron)= 1:3~40:1
pyrazole derivative(I): compound(B-18:dimethenamid)= 2:1~1:50
pyrazole derivative(I): compound(B-19:acetochlor)= 2:1~1:50
pyrazole derivative(I): compound(B-20:pyridate)=3:2~1:50
pyrazole derivative(I): compound(B-21:imazamethabenzmethyl)=1:6~40:1

The above pyrazole derivatives (Ia), (Ib) and (Ic) and the compounds (B-1)~(B-20) are preferably mixed in the following mixing ratios, respectively.

pyrazole derivative(Ia): compound(B-1:atrazine)=1:1~1:50
pyrazole derivative(Ia): compound(B-2:cyanazine)= 2:1~1:25
pyrazole derivative(Ia): compound(B-3:metribuzin)= 3:1~1:12
pyrazole derivative(Ia): compound(B-4:linuron)=2:1~1:25
pyrazole derivative(Ia): compound(B-6:bentazone)= 1:2~1:100
pyrazole derivative(Ia): compound(B-7:dicamba)=1:1~1:50
pyrazole derivative(Ia): compound(B-9:2,4-D)=2:1~1:50
pyrazole derivative(Ia): compound(B-10:bromoxynil)= 1:1~1:50
pyrazole derivative(I): compound(B-11:alachlor)=2:1~1:25
pyrazole derivative(I): compound(B-12:metolachlor)= 2:1~1:25
pyrazole derivative(Ia): compound(B-13:pendimethalin)= 2:1~1:25
pyrazole derivative(Ia): compound(B-14:nicosulfuron)= 1:3~40:1
pyrazole derivative(Ia): compound(B-15:rimsulfuron)= 1:3~40:1
pyrazole derivative(Ia): compound(B-16:imazethapyr)= 1:6~40:1
pyrazole derivative(Ia): compound(B-17:primisulfuron)= 1:3~40:1
pyrazole derivative(Ia): compound(B-18:dimethenamid)= 2:1~1:50
pyrazole derivative(Ia): compound(B-19:acetochlor)= 2:1~1:50
pyrazole derivative(Ia): compound(B-20:pyridate)= 3:2~1:50
pyrazole derivative(Ib): compound(B-1:atrazine)=2:1~1:50
pyrazole derivative(Ib): compound(B-2:cyanazine)= 2:1~1:50
pyrazole derivative(Ib): compound(B-3:metribuzin)= 3:1~1:25
pyrazole derivative(Ib): compound(B-4:linuron)=2:1~1:50
pyrazole derivative(Ib): compound(B-5:methbenzurone)= 1:2~1:100
pyrazole derivative(Ib): compound(B-6:bentazone)=6:1~1:3
pyrazole derivative(Ib): compound(B-7:dicamba)=1:1~1:50
pyrazole derivative(Ib): compound(B-8:atrazine)=4:3~1:12
pyrazole derivative(Ib): compound(B-9:2,4-D)=2:1~1:50
pyrazole derivative(Ib): compound(B-10:bromoxynil)= 1:1~1:50
pyrazole derivative(Ib): compound(B-11:alachlor)= 2:1~1:25
pyrazole derivative(Ib): compound(B-12:metolachlor)= 2:1~1:25
pyrazole derivative(Ib): compound(B-13:pendimethalin)= 2:1~1:25
pyrazole derivative(Ib): compound(B-14:nicosulfuron)= 1:3~40:1
pyrazole derivative(Ib): compound(B-15:rimsulfuron)= 1:3~40:1
pyrazole derivative(Ib): compound(B-16:imazethapyr)= 1:6~40:1
pyrazole derivative(Ib): compound(B-17:primisulfuron)= 1:3~40:1
pyrazole derivative(Ib): compound(B-18:dimethenamid)= 2:1~1:50
pyrazole derivative(Ib): compound(B-19:acetochlor)= 2:1~1:50
pyrazole derivative(Ic): compound(B-1:atrazine)=2:1~1:50
pyrazole derivative(Ic): compound(B-2:cyanazine)= 2:1~1:50
pyrazole derivative(Ic): compound(B-3:metribuzin)= 3:1~1:25
pyrazole derivative(Ic): compound(B-4:linuron)=2:1~1:50
pyrazole derivative(Ic): compound(B-6:bentazone)= 1:2~1:100
pyrazole derivative(Ic): compound(B-7:dicamba)=1:1~1:50
pyrazole derivative(Ic): compound(B-8:chlorpyralid)= 4:3~1:12
pyrazole derivative(Ic): compound(B-9:2,4-D)=2:1~1:50
pyrazole derivative(Ic): compound(B-10:bromoxynil)= 1:1~1:50
pyrazole derivative(Ic): compound(B-11:alachlor)= 2:1~1:25
pyrazole derivative(Ic): compound(B-12:metolachlor)= 2:1~1:25
pyrazole derivative(Ic): compound(B-13:pendimethalin)= 2:1~1:25
pyrazole derivative(Ic): compound(B-14:nicosulfuron)= 1:3~40:1
pyrazole derivative(Ic): compound(B-15:rimsulfuron)= 1:3~40:1
pyrazole derivative(Ic): compound(B-16:imazethapyr)= 1:6~40:1
pyrazole derivative(Ic): compound(B-17:primisulfuron)= 1:3~40:1
pyrazole derivative(Ic): compound(B-18:dimethenamid)= 2:1~1.50
pyrazole derivative(Ic): compound(B-19:acetochlor)= 2:1~1:50

The process for the production of the herbicide composition of the present invention will be explained hereinafter.

The herbicide composition of the present invention is obtained by mixing the pyrazole derivative of the above general formula (I) and at least one compound selected from a group of the above herbicide compounds with a liquid carrier such as a solvent or a solid carrier such as a mineral powder and forming the mixture into a preparation in the form of a wettable powder, an emulsifiable concentrate, a dust, granules, a flowable preparation or a solution. The preparation can be formed by adding surfactants such as an emulsifier, a dispersing agent, a spreading agent, a systemic agent and a stabilizer and other adjuvants as required.

When the herbicide composition of the present invention is used as a wettable powder, generally, a composition is prepared by 10 to 55% by weight of the pyrazole derivative (I) and at least one selected from a group of the above herbicide compounds as active ingredients, 40 to 88% by weight of a solid carrier and 2 to 5% by weight of a surfactant, and can be used as such. Further, when it is used in the forms of an emulsifiable concentrate and a flowable preparation, generally, it can be prepared by 5 to 50% by weight of the pyrazole derivative (I) and at least one compound selected from a group of the above herbicide compounds as active ingredients, 35 to 90% by weight of a solvent and 5 to 15% by weight of a surfactant and other adjuvant.

On the other hand, when herbicide composition of the present invention is used in the form of a dust, generally, it can be prepared by mixing 1 to 15% by weight of the pyrazole derivative (I) and at least one compound selected from a group of the above herbicide compounds as active ingredients and 85 to 99% by weight of a solid carrier. Further, when it is used in the form of granules, it can be prepared by mixing 0.1 to 15% by weight of the pyrazole derivative (I) and at least one compound selected from a group of the above herbicide compounds as active ingredients, 80 to 97.9% by weight of a solid carrier and 2 to 5% by weight of a surfactant. The above solid carrier can be selected from mineral fine powders, and the mineral fine powders include oxides such as diatomaceous earth and slaked lime, phosphates such as apatite, sulfates such as gypsum, and silicates such as talc, pyroferrite, clay, kaolin, bentonite, acid clay, white carbon, powdered quartz and powdered silica.

The liquid carrier includes paraffin- or naphthene-based hydrocarbons such as kerosene, mineral oil and spindle oil, aromatic hydrocarbons such as benzene, toluene and xylene, chlorinated hydrocarbons such as o-chlorotoluene, trichloromethane and trichloroethylene, alcohols such as cyclohexanol, amyl alcohol and ethylene glycol, alcohol ethers such as ethylene glycol monomethyl ether and ethylene glycol monoethyl ether, ketones such as isophorone, cyclohexanone and cyclohexenyl-cyclohexanone, ethers such as butyl cellosolve, dimethyl ether and methyl ethyl ether, esters such as isopropyl acetate, benzyl acetate and methyl phthalate, amides such as dimethylformamide, nitriles such as acetonitrile and propionitrile, sulfoxides such as dimethylsulfoxde, organic solvents such as mixtures of these, and water.

Further, the surfactant can be selected from anionic ones (alkylbenzenesulfonate, alkylsulfonate and lauric amide sulfonate), nonionic ones (polyoxyethylene octyl ether, polyethylene glycol laurate and sorbitan alkyl ester), cationic ones (dimethyllaurylbenzylammonium chloride, laurylamine and stearyltrimethylammonium chloride) and amphoteric ones (amino acid and betaine).

For improving the properties of the preparation and enhancing the herbicidal efficacy of the preparation, the herbicide composition of the present invention may contain polymer compounds or adjuvants such as sodium alginate, carboxymethyl cellulose, carboxyvinyl polymer, gum arabic and hydroxypropylmethylcellulose.

The herbicide composition of the present invention can simultaneously control gramineous weeds and broad-leaved weeds at a low dosage without damaging useful crops (i.e., without phytotoxicity) by soil treatment or foliar treatment for upland crops such as corn, Indian millet and the like before or after the germination of the weeds.

Further, the herbicide composition of the present invention exhibits excellent herbicidal efficacy against weeds in orchards and non-agricultural land (factory field, railroad site, roadside, river bed and fallow field) by soil treatment or foliar treatment.

The herbicide composition of the present invention is applied in an amount, as active ingredients, of approximately 10 to 1,000 g, preferably 70 to 700 g, per hectare. When it is applied to plant stalks and leaves, it is diluted to approximately 100 to 100,000 ppm, preferably 250 to 50,000 ppm, before use.

The pyrazole derivative of the general formula (I) can be produced by the following production process.

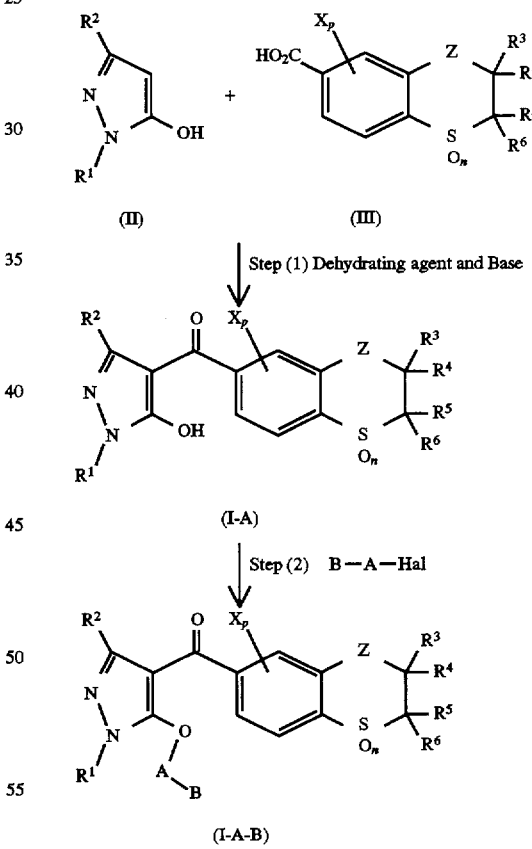

In the above reaction scheme, $R^1$-$R^6$, X, p, n, A, B and Z are as defined in the general formula (I), and Hal is a halogen atom.

Some of thiochromancarboxylic acids of the general formula (III) used as a starting material for the production of the pyrazole derivative of the general formula (I) are already known, and the process for the production thereof is described in International Laid-open Patent Publications WO93/18031, WO94/01431 and WO95/04054. Those which are not known can be produced according to the process described in the above International Laid-open Patent Publications or U.S. Pat. No. 5,035,793.

Further, the thiochromancarboxylic acid of the general formula (III) can be produced by one of the following production schemes depending upon the structure of substituent. In the reaction schemes, $R^1$ to $R^{12}$, X, p, n, A, B and Z are as defined in the general formula (I). Hal is a halogen atom, and q is 1 or 2.

The thiochromancarboxylic acid of the general formula (III) in which Z is

i.e., a thiochromancarboxylic acid of the following general formula (IIIa), can be produced by the method in any one of the production schemes 1–3.

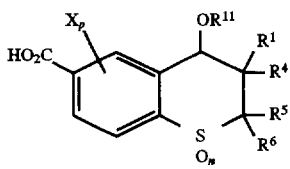

Production scheme 1

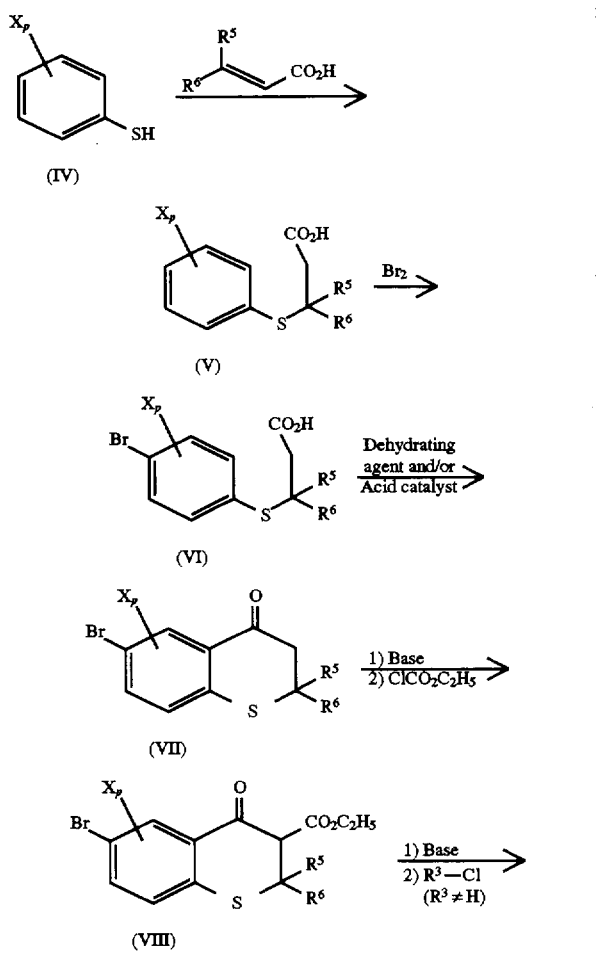

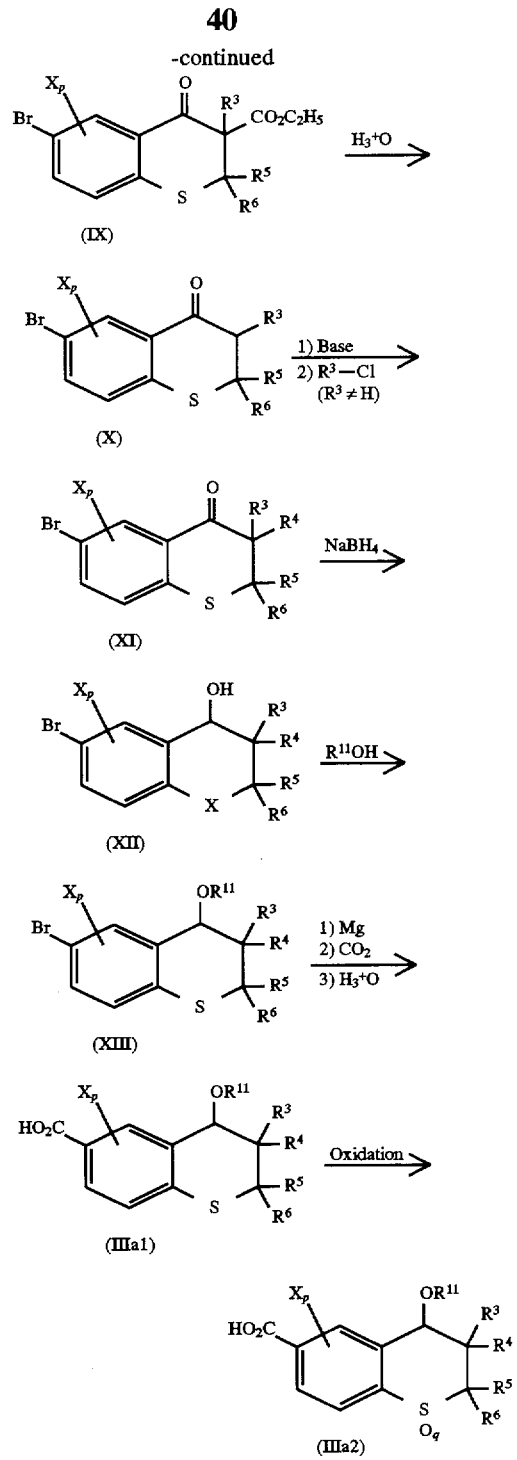

In the production scheme 1, a compound (IIIa1) is a thiochromancarboxylic acid of the general formula (IIIa) in which n=0.

A compound (IIIa2) is a thiochromancarboxylic acid of the general formula (IIIa) in which n=1 or 2.

Production scheme 2

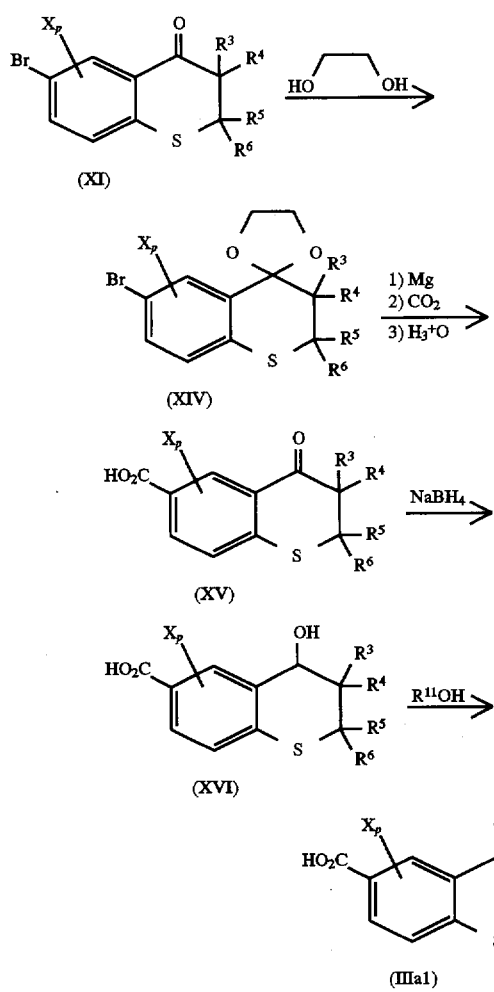

The following is the same as in Scheme 1.

Production scheme 3

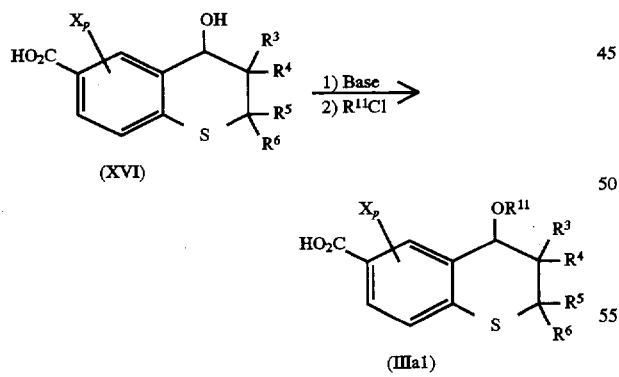

To be followed in the same manner as in Scheme 1.
The compound of the general formula (III) in which Z is

i.e., a thiochromancarboxylic acid of the following general formula (IIIb), can be produced by the method in any one of the production schemes 4–5.

Production scheme 4

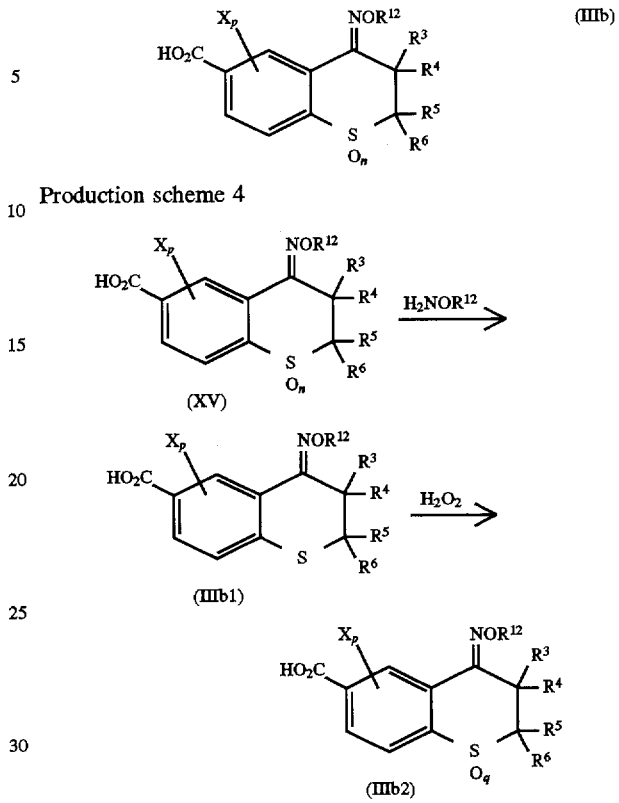

In the production scheme 4, a compound (IIIb1) is a thiochromancarboxylic acid of the general formula (IIIb) in which
n=0.

A compound (IIIb2) is a thiochromancarboxylic acid of the general formula (IIIb) in which
n=1 or 2.

Production scheme 5

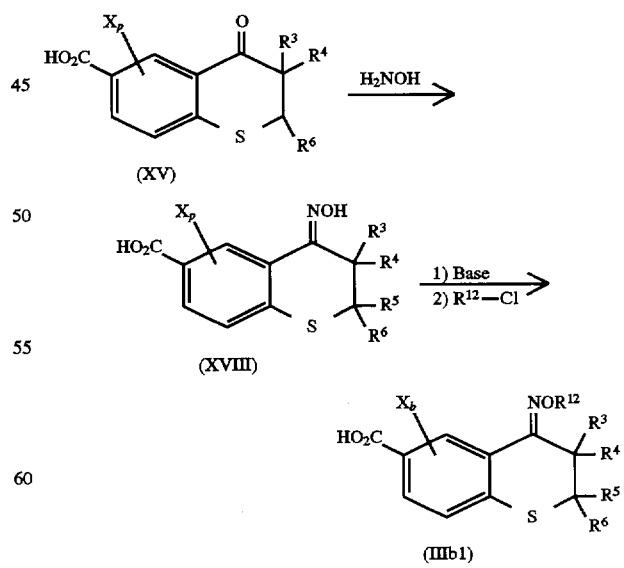

The following is the same as in Scheme 4.

The thiochromancarboxylic acid of the general formula (III) in which Z is

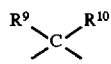

i.e., a thiochromancarboxylic acid of the following general formula (IIIc), can be produced by the method in any one of the production schemes 6–12.

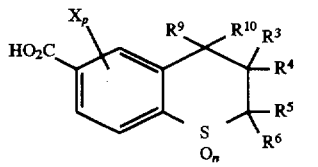

(IIIc)

Production scheme 6

The production scheme 6 is directed to a process for the production of a thiochromancarboxylic acid of the general formula (IIIc) in which $R^3$, $R^4$, $R^5$ and $R^6$ are all hydrogen atoms.

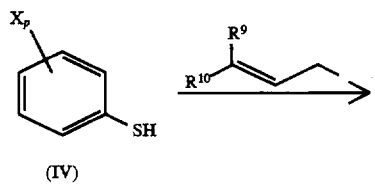

(IV)

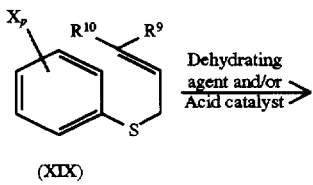

(XIX)

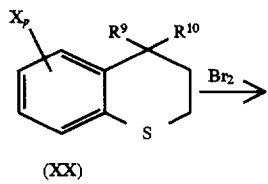

(XX)

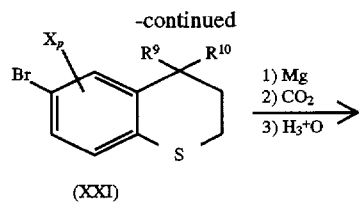

(XXI)

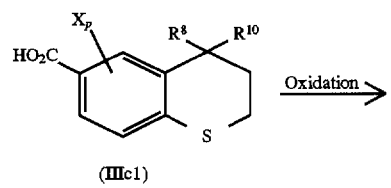

(IIIc1)

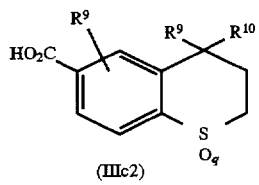

(IIIc2)

In the production scheme 6, a compound (IIIc1) is a thiochromancarboxylic acid of the general formula (IIIc) in which $R^3=R^4=R^5=R^6$=hydrogen atom, and n=0 (sulfide).

A compound (IIIc2) is a thiochromancarboxylic acid of the general formula (IIIc) in which $R^3=R^4=R^5=R^6$=hydrogen atom, and n=1 (sulfoxide) or 2 (sulfone).

Production scheme 7

The thiochromancarboxylic acid of the general formula (IIIc1) or (IIIc2) in the above production scheme 7 can be also produced by the production scheme 7.

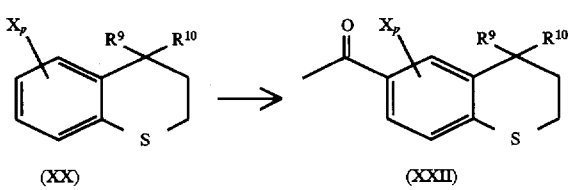

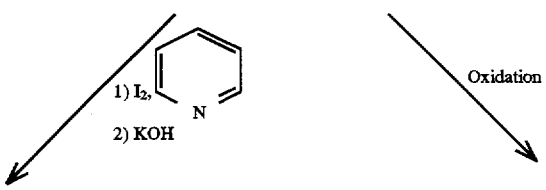

-continued

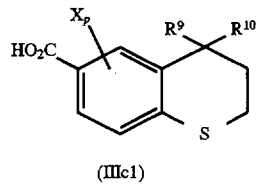
(IIIc1)

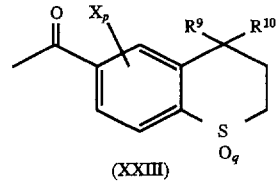
(XXIII)

Oxidation ↘    ↙ Haloform reaction

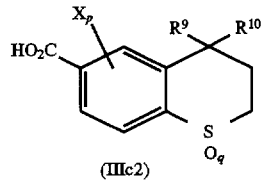
(IIIc2)

Production scheme 8

A thiochromancarboxylic acid of the general formula (IIIc2) in which p=1 and

Position of substituent X=5-position on the thiochroman ring, can be also produced by the production scheme 7.

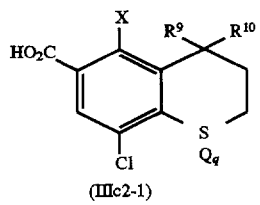
(IIIc2-1)

$\xrightarrow{\text{Zn}}{\text{KOH C}_2\text{H}_5\text{OH}}$

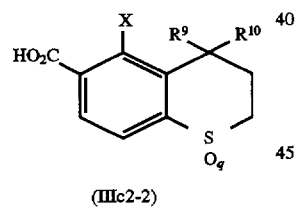
(IIIc2-2)

Production scheme 9

The production scheme 9 is directed to a process for the production of a thiochromancarboxylic acid of the general formula (IIIc) in which $R^{10}=C_1\sim C_4$ alkyl group or $C_2\sim C_5$ alkenyl group and
$R^9=C_1\sim C_4$ alkyl group or $C_1\sim C_4$ haloalkyl group.

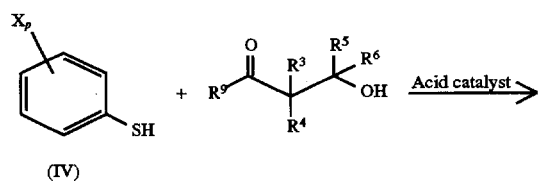
(IV)

-continued

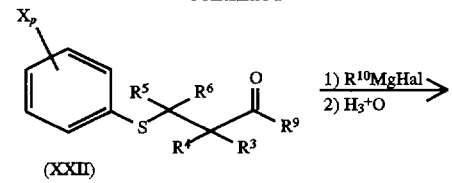
(XXII)

1) $R^{10}$MgHal
2) $H_3^+O$

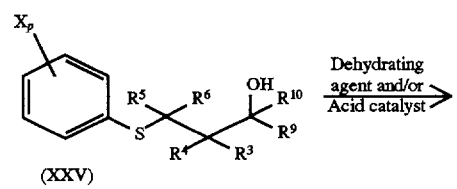
(XXV)

Dehydrating agent and/or Acid catalyst

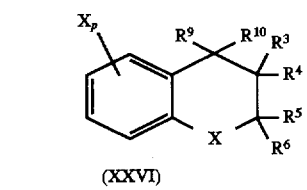
(XXVI)

Br₂

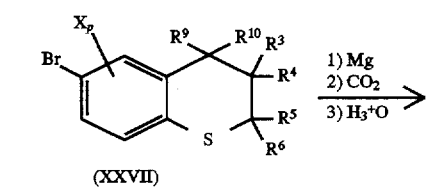
(XXVII)

1) Mg
2) CO₂
3) $H_3^+O$

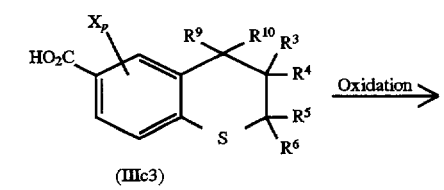
(IIIc3)

Oxidation

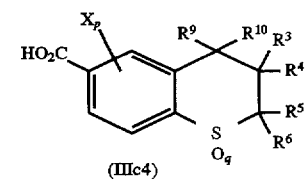
(IIIc4)

In the production scheme 9, a compound (IIIc3) is a thiochromancarboxylic acid of the general formula (IIIc) in which $R^{10}=C_1\sim C_4$ alkyl group or $C_2\sim C_5$ alkenyl group, $R^9=C_1\sim C_4$ alkyl group or $C_1\sim C_4$ haloalyl group, and n=0.

A compound (IIIc4) is a thiochromancarboxylic acid of the general formula (IIIc) in which $R^{10}=C_1\sim C_4$ alkyl group or $C_2\sim C_5$ alkenyl group, $R^9=C_{1\sim C4}$ alkyl group or $C_1\sim C_4$ haloalkyl group, and n=1 or 2.

Production scheme 10

The production scheme 10 is directed to a process for the production of a thiochromancarboxylic acid of the general formula (IIIc) in which $R^9=R^{10}$=hydrogen atom.

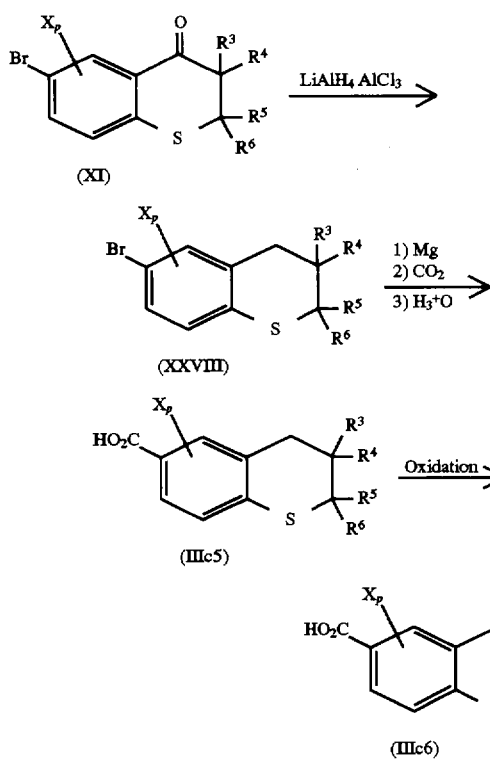

In the production scheme 10, a compound (IIIc5) is a compound of the general formula (IIIc) in which $R^9=R^{10}$=hydrogen atom, and n=0.

A compound (IIIc6) is a compound of the general formula (IIIc) in which $R^9=R^{10}$=hydrogen atom, and n=1 or 2.

Production scheme 11

The production scheme 11 is directed to a process for the production of a thiochromancarboxylic acid of the general formula (IIIc) in which $R^9$=hydrogen atom.

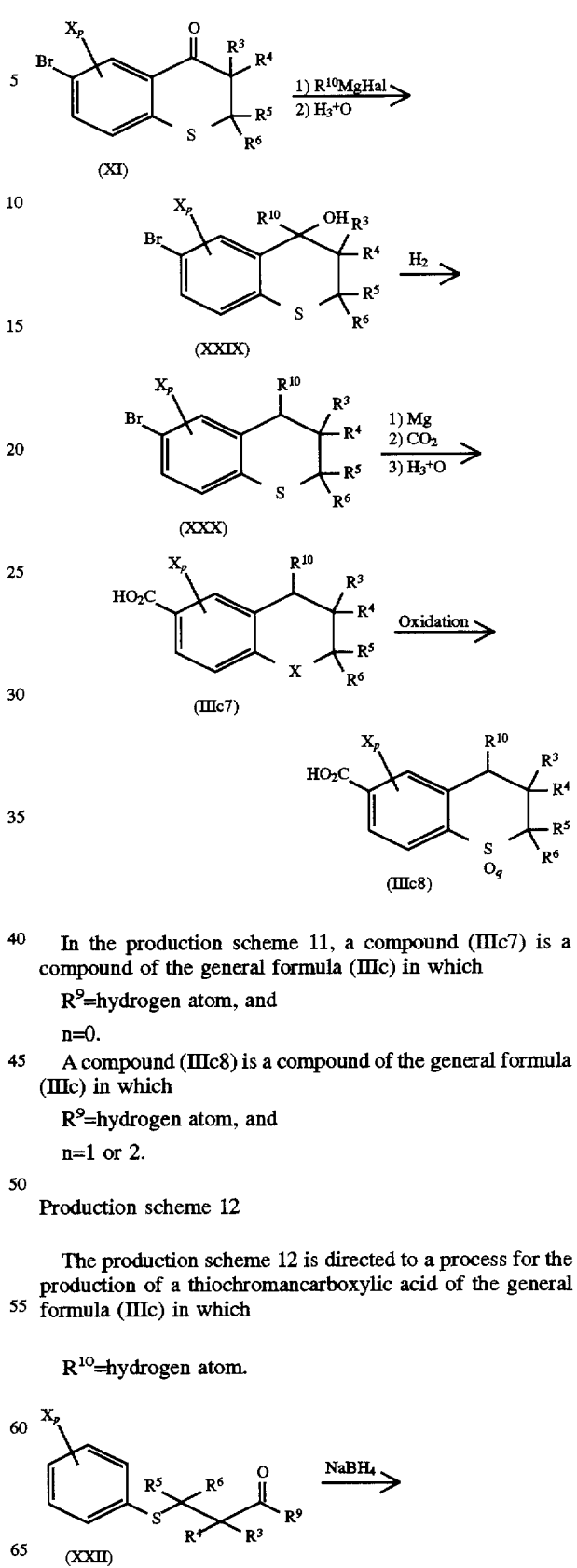

In the production scheme 11, a compound (IIIc7) is a compound of the general formula (IIIc) in which $R^9$=hydrogen atom, and n=0.

A compound (IIIc8) is a compound of the general formula (IIIc) in which $R^9$=hydrogen atom, and n=1 or 2.

Production scheme 12

The production scheme 12 is directed to a process for the production of a thiochromancarboxylic acid of the general formula (IIIc) in which $R^{10}$=hydrogen atom.

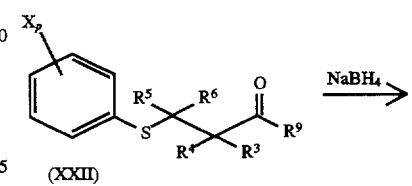

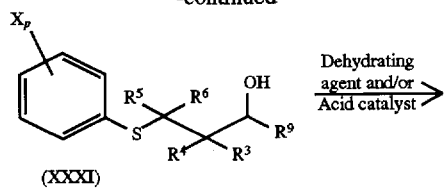

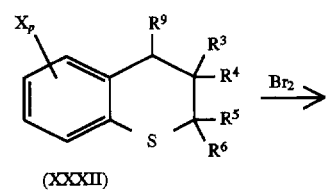

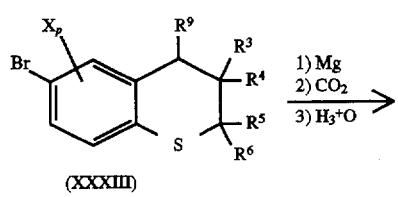

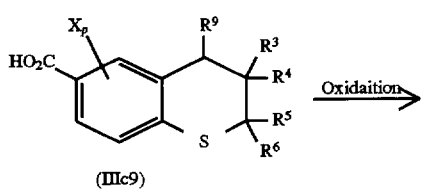

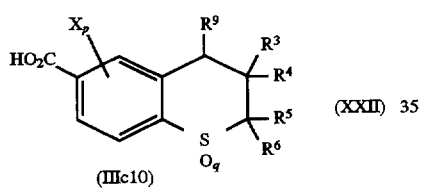

In the production scheme 12, a compound (IIIc9) is a thiochromancarboxylic acid of the general formula (IIIc) in which $R^{10}$=hydrogen atom, and n=0.

A compound (IIIc10) is a compound of the general formula (IIIc) in which $R^{10}$=hydrogen atom, and n=1 or 2.

Triphenols of the general formula (IV) (production scheme 1), as a starting material for the production of the thiochromancarboxylic acid, can be produced by one of the following methods depending upon their substituents. In the following reaction scheme, X and p are as defined in the general formula (I) and Hal is a halogen atom.

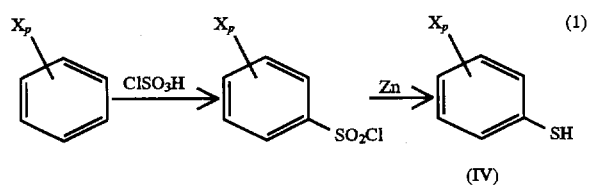

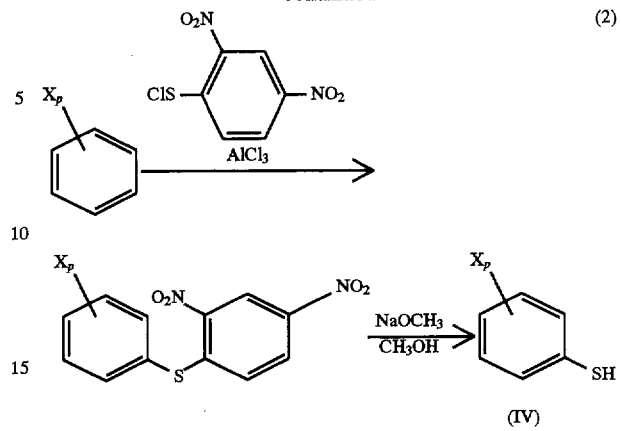

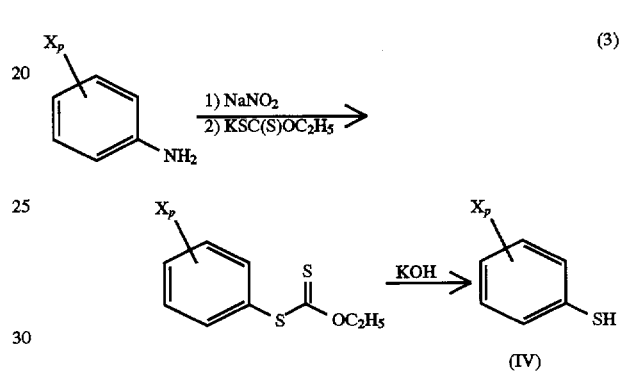

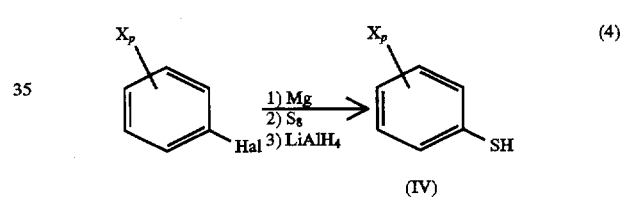

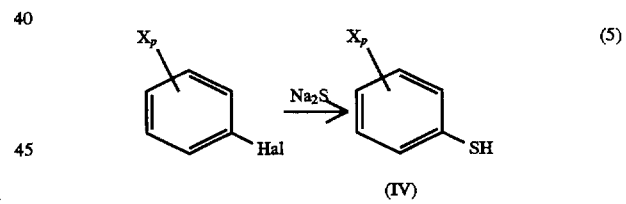

5-Hydroxypyrazoles of the general formula (II), as a starting material for the production of the pyrazole derivative (I) of the present invention, can be produced by one of the following methods depending upon their substituents. In the following reaction schemes, $R^1$ and $R^2$ are as defined in the general formula (I).

(1) Process mentioned in East German Pat. No. 83145

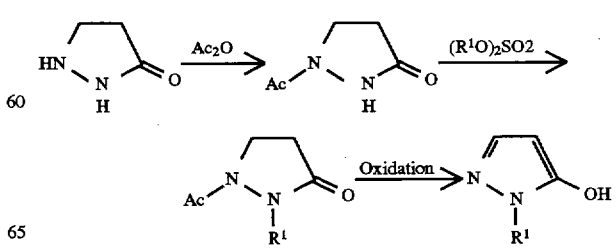

(2) Process mentioned in U.S. Pat. No. 4,744,815

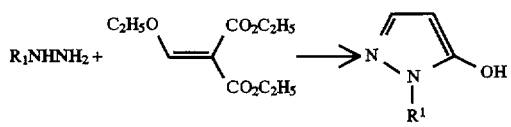

(3) Process mentioned in Japanese Laid-open No. Hei-3-44375

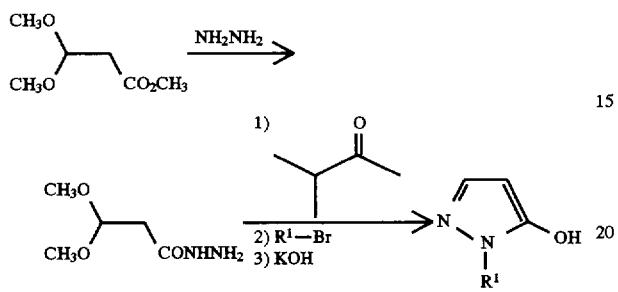

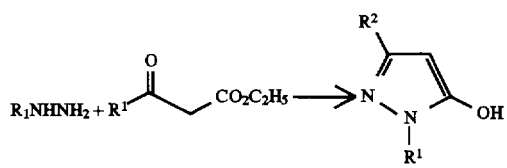

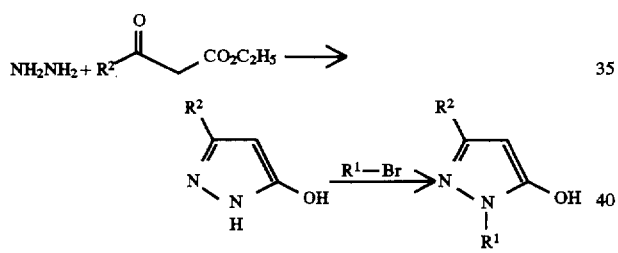

The above (1)~(3) are directed to a process for the production of 5-hydroxypyrazoles of the general formula (II) in which $R^2$=hydrogen atom.

The above (5)~(6) are directed to a process for the production of 5-hydroxypyrazoles of the general formula (II) in which $R^2=C_1$~$C_4$ alkyl group, $C_1$~$C_4$ haloalkyl group or $C_2$~$C_4$ alkoxy group.

EXAMPLES

The present invention will be specifically explained with reference to Production Referential Examples, Preparation Examples and Examples hereinafter.

Production Referential Examples

Production Referential Example 1

Synthesis of 4-methoxy-5-methyl-6-(5-cyclohexylcarbonyloxy-1-ethylpyrazol-4-yl)carbonylthiochroman-1,1-dioxide (Compound Ia-7)

As a starting material, 4-methoxy-5-methyl-6-(1-ethyl-5-hydroxypyrazol-4-yl)carbonylthiochroman-1,1-dioxide corresponding to pyrazole derivative (I-H) was used. 0.4 Gram (1.1 mmol) thereof was dissolved in 4 ml of methylene chloride, and 0.22 g (2.2 mmol) of triethylamine as a base and 0.19 g (1.3 mmol) of cyclohexylcarbonyl chloride corresponding to compound B-A-Hal as a reaction reagent were added. The mixture was allowed to react at room temperature for 8 hours. A saturated sodium carbonate aqueous solution was added to the reaction mixture, and the resultant mixture was extracted with ethyl acetate. An organic layer was dried over anhydrous sodium sulfate. The solvent was distilled off under reduced pressure, and the resultant oil was purified by flush column chromatography (Wako Gel C-300; hexane/ethyl acetate=1:1) to give 0.28 g (yield 54%) of 4-methoxy-5-methyl-6-(5-cyclohexylcarbonyloxy-1-ethylpyrazol-4-yl)carbonylthiochroman-1,1-dioxide.

Referential Production Example 2

Synthesis of 4-methoxyimino-5-methyl-6-(1-ethyl-5-n-propylsulfonyloxypyrazol-4-yl)carbonylthiochroman-1,1-dioxide (Compound Ib-1)

A 100-ml eggplant type flask was charged with 1.1 g (2.9 mmol) of 4-methoxyimino-5-methyl-6-(1-ethyl-5-hydroxypyrazol-4-yl)carbonylthiochroman-1,1-dioxide corresponding to pyrazole derivative (I-H) as a starting material, and 20 ml of methylene chloride was added and allowed to dissolve it. Then, a solution of 0.41 g of potassium carbonate in 20 ml of distilled water was added. Further, a solution of 0.6 g (4.2 mmol) of n-propanesulfonyl chloride corresponding to compound B-A-Hal as a reaction reagent in 5 ml of methylene chloride was added, and further, 0.05 g of benzyltriethylammonium chloride as a catalyst was added. The mixture was allowed to react at room temperature for 24 hours with stirring. After the reaction was completed, a methylene chloride layer was separated and dried over anhydrous sodium sulfate, and then the methylene chloride was distilled off under reduced pressure. The resultant oily substance was purified with a column packed with silica gel. A mixture of ethyl acetate with n-hexane was used as a developer solution.

By the above procedures, 0.88 g of 4-methoxyimino-5-methyl-6-(1-ethyl-5-n-propylsulfonyloxypyrazol-4-yl)carbonylthiochroman-1,1-dioxide (Compound Ib-1) was obtained as a solid. The yield thereof was 62%.

Referential Production Example 3

Sythesis of 4-methoxyimino-5-methyl-6-(1-5-p-toluenesulfonyloxypyrazol-4-yl)carbonythiochroman-1,1-dioxide (Compound Ib-2)

0.4 Gram (1.1 mmol) of 4-methoxyimino-5-methyl-6-(1-ethyl-5-hydroxypyrazol-4-yl)carbonylthiochroman-1,1-dioxide corresponding to pyrazole derivative (I-H), 0.23 g (1.2 mmol) of phenacyl bromide corresponding to compound B-A-Hal and 0.15 g of potassium carbonate were added to 10 ml of acetone, and the mixture was stirred under heat for 8 hours. Insolubles were removed by filtration, and then the acetone was distilled off. The residue was dissolved in ethyl acetate, and the mixture was washed with a saturated sodium chloride aqueous solution and dried over sodium sulfate. The ethyl acetate was distilled off under reduced pressure, and the residue was subjected to column chromatography (hexane/ethyl acetate) to give 4-methoxyimino-5-methyl-6-(1-ethyl-5-phenacyloxypyrazol-4-yl)carbonylthiochroman-1,1-dioxide (Compound Ib-2) at a yield of 52%.

Referential Production Example 4

Synthesis of 4-methoxyimino-5-methyl-6-(1-ethyl-5-p-toluenesulfonyloxypyrazol-4-yl)carbonylthiochroman-1,1-dioxide (Compound Ib-3)

4-Methoxyimino-5-methyl-6-(1-ethyl-5-p-toluenesulfonyloxypyrazol-4-yl)carbonylthiochroman-1,1-dioxide (Compound Ib-3) was obtained in the same manner as in Referential Production Example 2 except that the reaction reagent was replaced with p-toluenesulfonyl chloride corresponding to compound B-A-Hal.

Referential Production Example 5

Synthesis of 4,4,5,8-tetramethyl-6-(1-ethyl-5-hydroxypyrazol-4-yl)carbonylthiochroman-1,1-dioxide (Compound Ic-1)

7.4 Grams (0.026 mol) of 4,4,5,8-tetramethylthiochroman-6-carboxylic acid-1,1-dioxide corresponding to thiochroman carboxylic acid (IIIc), 3.4 g (0.03 mol) of 1-ethyl-5-hydroxypyrazole corresponding to 5-hydroxypyrazole (II) and 6.22 g (0.03 mol) of DCC (N,N'-dicyclohexylcarbodiimide) were all together added to 50 ml of tert-amyl alcohol, and the mixture was stirred at room temperature for 30 minutes. Then, 1.8 g (0.013 mol) of anhydrous potassium carbonate was added. The reaction mixture was allowed to react at 80° C. for 8 hours, and the reaction solvent was distilled off under reduced pressure. The resultant residue was dispersed in a 5% potassium carbonate aqueous solution and ethyl acetate to separate it into two layers. Further, the aqueous layer was adjusted to a pH of 1 with 5% hydrochloric acid, and the formed solid was recovered by filtration to give 6.13 g (yield 62%) of 4,4,5,8-tetramethyl-6-(1-ethyl-5-hydroxypyrazol-4-yl)carbonylthiochroman-1,1-dioxide (Compound Ic-1).

Referential Production Example 6

Synthesis of 4,4,5,8-tetramethyl-6-(1-ethyl-5-ethanesulfonyloxypyrazol-4-yl)carbonylthiochroman-1,1-dioxide (Compound Ic-2)

0.7 Gram (1.9 mmol) of the 4,4,5,8-tetramethyl-6-(1-ethyl-5-hydroxypyrazol-4-yl)carbonylthiochroman-1,1-dioxide (Compound Ic-1) corresponding to pyrazole derivative (I-H), obtained in Referential Production Example 5, was dissolved in 8 ml of methylene chloride. Then, a solution of 0.51 g (3.8 mmol) of potassium carbonate in 5 ml of water was added, and further, 0.49 g (3.8 mmol) of ethanesulfonyl chloride and 0.05 g (0.2 mmol) of benzyltriethylammonium chloride, corresponding to compound B-A-Hal, were added. The mixture was allowed to react at room temperature for 2 hours, and further refluxed under heat for 2 hours. The reaction mixture was allowed to cool, and then a methylene chloride layer was recovered and dried over anhydrous sodium sulfate. The solvent was distilled off under reduced pressure, and the resultant oil was purified by silica gel column chromatography to give 0.73 g (yield 82%) of 4,4,5,8-tetramethyl-6-(1-ethyl-5-ethanesulfonyloxypyrazol-4-yl)carbonylthiochroman-1,1-dioxide (Compound Ic-2).

Table 1 shows physical property data of the compounds obtained in the above Referential Production Examples 1~6.

TABLE 1

| Prepn Ex. No. | Compd No. | N.M.R. (ppm) Internal standard: tetramethylsilane Solvent: deuterochloroform | I.R. $(cm^{-1})$ KBr tablet | mp (°C.) |
|---|---|---|---|---|
| 1 | Ia-7 | 1.42(3H, t, J=7.3Hz)1.3–2.0(10H, m) 2.33(3H, s)2.3–2.8(3H, m) 3.1–3.3(1H, m)3.47(3H, s) 3.6–3.8(1H, m)3.99(2H, q, J=7.3Hz) 4.52(1H, t, J=2.9Hz) 7.44(1H, d, J=8.2Hz)7.61(1H, s) 7.86(1H, d, J=8.2Hz) | 2970, 1800, 1670, 1300, 1140 | 139.0–141.0 |
| 2 | Ib-1 | 1.18(3H, t)1.52(3H, t)2.00 2.20(2H, m) 2.52(3H, s)3.35(4H, t)3.73(2H, t) 4.06(3H, s)4.23(2H, q)7.45(H, s) 7.48(H, d)7.96(H, d) | 3000, 2960, 1665, 1135, 1325, 1190, 1395 | 146.0–150.7 |
| 3 | Ib-2 | 1.51(3H, t)2.41(3H, s)3.20–3.40(4H, m) 4.02(3H, s)4.28(2H, q)6.19(2H, s) 7.19(H, s)7.30–8.10(7H, m) | 2950, 1710, 1650, 1320, 1130 | — |
| 4 | Ib-3 | 1.49(3H, t)2.47(3H, s)2.49(3H, s) 3.3–3.5(4H, m)4.05(3H, s)4.17(2H, q) 7.356(1H, s(7.4–8.0(6H, m) | 2950, 1680, 1320, 1130 | glass-like |
| 5 | Ic-1 | 1.45(3H, t)1.55(6H, S)2.30–2.50(2H, m) 2.50(3H, s)2.80(3H ,s)3.40–3.60(2H, m) 4.10(2H, q)6.20(H, s)7.20(H, s) | 2550–3500, 2950, 3000, 1630, 1290, 1130 | 208.8–209.3 |
| 6 | Ic-2 | 1.50(3H, t)1.60(6H, s)1.70(3H, t) 2.30–2.60(2H, m)2.50(3H, s)2.80(3H, s) 3.30–3.60(2H, m)3.80(2H, q)4.20(2H, q) 7.10(H, s)7.40(H, s) | 2940, 3000, 1660, 1180 1140, 1290, 1380 | 164.1–165.7 |

Preparation Examples

The method of forming preparations will be explained with reference to Preparation Examples hereinafter. "Part" in the following Preparation Examples stands for part by weight.

Preparation Example 1
[Wettable powder]

| Compound (Ia-1), (Ib-1) or (Ic-1) | 5 parts |
|---|---|
| Compound (B-1) | 25 parts |
| Diatomaceous earth | 52 parts |
| White carbon | 15 parts |
| Sodium alkylbenzenesulfonate | 2 parts |
| Sodium lignisulfonate | 1 part |

The above components were mixed and homogeneously mixed and pulverized to give 100 part of a wettable powder.

Preparation Example 2
[Emulsifiable concentrate]

| Compound (Ia-1), (Ib-1) or (Ic-1) | 5 parts |
|---|---|
| Compound (B-2) | 25 parts |
| Xylene | 30 parts |
| Methylnaphthalene | 20 parts |
| Sorpol 2680 | 20 parts |

(Surfactant supplied by Toho Chemical Co., Ltd.)

The above components were homogeneously dissolved and mixed to give 100 parts of an emulsifiable concentrate.

Preparation Example 3
[Dust]

| Compound (Ia-1), (Ib-1) or (Ic-1) | 0.3 part |
|---|---|
| Compound (B-3) | 1.7 part |
| Diatomaceous earth | 20 parts |
| Talc | 78 parts |

The above components were mixed and homogeneously mixed and pulverized to give 100 parts of a dust.

Preparation Example 4
[Flowable preparation]

| Compound (Ia-1), (Ib-1) or (Ic-1) | 4 parts |
|---|---|
| Compound (B-4) | 25 parts |
| Methyl cellulose | 0.3 part |
| Colloidal silica | 1.5 part |
| Sodium ligninsulfonate | 1 part |
| Polyoxyethylene nonylphenyl ether | 2 parts |
| Water | 66.2 parts |

The above components were fully mixed and dispersed, and the resultant mixture in a slurry state was wet-pulverized to give 100 parts of a stable flowable preparation.

Preparation Example 5
[Wettable powder]

97 Parts of clay (trade name: Zeaklite, Supplied by Zeaklite Industry Co., Ltd.) as a carrier, 1.5 parts of alkylarylsulfonate (trade name: Neoplex, supplied by Kao-Atlas K.K.) as a surfactant and 1.5 parts by weight of a nonionic and anionic surfactant (trade name: Sorpol 800A, supplied by Toho Chemical Co., Ltd.) were homogeneously pulverized and mixed to prepare 90 parts of a carrier for a wettable powder. 10 Parts of Compound (Ia-1)~(Ia-5), (Ia-7), (Ib-1)~(Ib-3) or (Ic-1) or 10 parts of one of Compounds (B-1)~(B-2) was homogeneously mixed with, and pulverized together with, the above carrier to give wettable powders. A wettable powder containing one of (Ia-1)~(Ia-5), (Ia-7), (Ib-1)~(Ib-3) and (Ic-1) and a wettable powder containing one of Compound (B-1)~(B-20) were mixed in a predetermined mixing ratio (active ingredient ratio) to give wettable powders.

A biological test of the herbicide composition of the present invention will be shown as Examples hereinafter.

EXAMPLE 1

[Foliar treatment test]

Seeds of weeds such as cocklebur, velvet leaf, Slender amaranth, green foxtail, crabgrass and barnyard grass and seeds of corn were sown in 1/2,000-are Wagner pots filled with upland soil, and covered with upland soil. Then, the seed were grown in a greenhouse, and when these weeds were at a 1.5~2.5 leaves stage, a predetermined amount of the herbicide obtained in the above Preparation Example 5 was suspended in water and uniformly sprayed onto foliar portions in a solution amount of 1,000 liters/hectare. Thereafter, the weeds were grown in a greenhouse, and 20 days after the treatment, the herbicide was determined for phytotoxicity to crops and herbicidal efficacy according to the following standard.

The herbicidal efficacy (weed control ratio %) was determined by measuring an above-ground green forage weight in a chemical-treated plot and an above-ground green forage weight in a non-treated plot and applying the measurement values to the following equation (A).

Weed control ratio (%)=(1—above-ground green forage weight in treated plot/above-ground green forage weight in non-treated plot)×100

The phytotoxicity was evaluated on the basis of the following six ratings.

Degrees of phytotoxicity

0—No phytotoxicity to crops is observed.

1—There is almost no phytotoxicity to crops.

2—Phytotoxicity to crops is observed to some extent.

3—Phytotoxicity to crops is observed.

4—Phytotoxicity to crops is markedly observed.

5—Crops almost died.

In a foliar treatment test, a herbicide is applied by spraying, and it is therefore difficult to bring the amount of the herbicide to test weeds and crop into a completely constant value. Further, in both a foliar treatment test and a soil treatment test, it is also difficult to constantly bring test conditions such as temperature, humidity, hours of sunlight or water content in soil into completely constant values in the tests even if the tests are carried out in a greenhouse.

Therefore, the herbicidal efficacy of the single active ingredient of each of Compounds (B-1)~(B-20) varied in each test. However, the herbicidal efficacy (synergistic effect) of each herbicide composition of the present invention was evaluated on the basis of the results of the tests on single active ingredients carried concurrently, and was reliable.

Table 2 shows the foliar treatment test results of single active ingredients of Compounds (Ia-1), (Ia-2), (Ia-3), (Ia-4), (Ia-5) and (Ia-7) and Compounds (B-1)~(B-4), (B-6), (B-7), (B-9), (B-10) and (B-14)~(B-17).

Tables 3~8 show the foliar treatment test results of herbicide compositions of Compounds (Ia-1), (Ia-2), (Ia-3), (Ia-4), (Ia-5) and (Ia-7) and Compounds (B-1)~(B-4), (B-6), (B-7), (B-9), (B-10) and (B-14)~(B-17).

TABLE 2

Foliar treatment (single active ingredient)

| Compd | Dosage (g/ha) | herbicidal efficacy % | | | | | | phyto-toxicity to corn |
|---|---|---|---|---|---|---|---|---|
| | | (a) | (b) | (c) | (d) | (e) | (f) | |
| (Ia-1) | 40 | 80 | 20 | 50 | 60 | 80 | 60 | 0 |
|  | 20 | 80 | 20 | 30 | 40 | 60 | 30 | 0 |
| (Ia-2) | 40 | 50 | 50 | 30 | 40 | 60 | 50 | 0 |
|  | 20 | 30 | 50 | 10 | 20 | 40 | 30 | 0 |
| (Ia-3) | 40 | 50 | 60 | 30 | 50 | 60 | 40 | 0 |
|  | 20 | 30 | 40 | 10 | 30 | 40 | 30 | 0 |
| (Ia-4) | 40 | 50 | 50 | 30 | 40 | 50 | 40 | 0 |
|  | 20 | 40 | 30 | 10 | 20 | 30 | 20 | 0 |
| (Ia-5) | 40 | 60 | 50 | 30 | 40 | 50 | 30 | 0 |
|  | 20 | 40 | 30 | 10 | 20 | 30 | 20 | 0 |
| (Ia-7) | 40 | 40 | 50 | 40 | 50 | 50 | 40 | 0 |
|  | 20 | 30 | 30 | 10 | 20 | 20 | 20 | 0 |
| (B-1) | 250 | 0 | 0 | 60 | 0 | 0 | 0 | 0 |
| (B-10) | 250 | 90 | 40 | 30 | 0 | 0 | 0 | 0 |
| (B-7) | 250 | 80 | 40 | 40 | 0 | 0 | 0 | 0 |
| (B-6) | 250 | 90 | 0 | 0 | 0 | 0 | 0 | 0 |
| (B-20) | 250 | 0 | 10 | 0 | 0 | 0 | 0 | 0 |
| (B-3) | 62 | 90 | 90 | 60 | 0 | 40 | 0 | 0 |
| (B-2) | 125 | 80 | 0 | 0 | 40 | 60 | 0 | 0 |
| (B-4) | 125 | 20 | 0 | 0 | 20 | 60 | 0 | 0 |
| (B-9) | 250 | 100 | 20 | 20 | 0 | 0 | 0 | 0 |
| (B-14) | 16 | 20 | 20 | 20 | 60 | 50 | 60 | 0 |
| (B-15) | 10 | 20 | 20 | 20 | 50 | 50 | 50 | 0 |
| (B-16) | 36 | 0 | 0 | 20 | 80 | 70 | 80 | 0 |
| (B-17) | 16 | 30 | 20 | 20 | 20 | 20 | 10 | 0 |

(a): Cocklebur
(b): Velvet leaf
(c): Slender amaranth
(d): Green foxtail
(e): Crabgrass
(f): Barnyard grass

TABLE 3

Foliar treatment (combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-1) + (B-1) 40 + 250 | 100 | 80 | 20 | 90 | 20 | 70 | 100 | 80 | 20 | 80 | 60 | 20 | 100 | 80 | 20 | 100 | 60 | 40 | 0 |
| (Ia-1) + (B-10) 20 + 250 | 100 | 98 | 2 | 100 | 52 | 48 | 80 | 51 | 29 | 80 | 40 | 40 | 90 | 60 | 30 | 80 | 30 | 50 | 0 |
| (Ia-1) + (B-7) 40 + 250 | 100 | 96 | 4 | 70 | 52 | 18 | 108 | 70 | 30 | 90 | 60 | 30 | 100 | 80 | 20 | 80 | 60 | 20 | 0 |
| (Ia-1) + (B-6) 40 + 250 | 100 | 98 | 2 | 80 | 20 | 60 | 100 | 50 | 50 | 80 | 60 | 20 | 100 | 80 | 20 | 90 | 60 | 30 | 0 |
| (Ia-1) + (B-20) 40 + 250 | 100 | 80 | 20 | 90 | 20 | 70 | 60 | 50 | 10 | 80 | 60 | 20 | 100 | 80 | 20 | 90 | 60 | 30 | 0 |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 4

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-2) + (B-1) 20 + 250 | 100 | 30 | 70 | 100 | 50 | 50 | 90 | 64 | 26 | 90 | 20 | 70 | 100 | 40 | 60 | 90 | 30 | 60 | 0 |
| (Ia-2) + (B-10) 40 + 250 | 100 | 95 | 5 | 100 | 70 | 30 | 70 | 51 | 19 | 90 | 40 | 50 | 80 | 60 | 20 | 80 | 50 | 30 | 0 |
| (Ia-2) + (B-7) 40 + 250 | 100 | 90 | 10 | 100 | 70 | 30 | 80 | 58 | 22 | 50 | 40 | 10 | 70 | 60 | 10 | 70 | 50 | 20 | 0 |
| (Ia-2) + (B-6) 40 + 250 | 100 | 95 | 5 | 100 | 50 | 50 | 90 | 30 | 60 | 80 | 40 | 40 | 100 | 60 | 40 | 90 | 50 | 40 | 0 |
| (Ia-2) + (B-20) 40 + 250 | 50 | 50 | 0 | 60 | 55 | 5 | 50 | 30 | 20 | 50 | 40 | 10 | 60 | 60 | 0 | 60 | 50 | 10 | 0 |
| (Ia-2) + (B-3) 40 + 62 | 100 | 95 | 5 | 100 | 95 | 5 | 100 | 72 | 28 | 90 | 40 | 50 | 100 | 76 | 24 | 100 | 50 | 50 | 0 |
| (Ia-2) + (B-2) 20 + 125 | 100 | 86 | 14 | 80 | 50 | 30 | 90 | 10 | 80 | 90 | 52 | 38 | 100 | 76 | 24 | 80 | 30 | 50 | 0 |
| (Ia-2) + (B-4) 40 + 125 | 100 | 60 | 40 | 100 | 50 | 50 | 90 | 30 | 60 | 90 | 52 | 38 | 100 | 84 | 16 | 100 | 50 | 50 | 0 |
| (Ia-2) + (B-9) 40 + 250 | 100 | 100 | 0 | 100 | 60 | 40 | 80 | 44 | 36 | 50 | 40 | 10 | 70 | 60 | 10 | 50 | 50 | 0 | 0 |
| (Ia-2) + (B-14) 40 + 16 | 80 | 60 | 20 | 60 | 60 | 0 | 50 | 44 | 6 | 80 | 76 | 4 | 80 | 80 | 0 | 80 | 80 | 0 | 0 |
| (Ia-2) + (B-15) 40 + 10 | 70 | 60 | 10 | 60 | 60 | 0 | 50 | 44 | 6 | 80 | 70 | 10 | 80 | 80 | 0 | 80 | 75 | 5 | 0 |
| (Ia-2) + (B-16) 40 + 36 | 60 | 50 | 10 | 50 | 50 | 0 | 50 | 44 | 6 | 90 | 88 | 2 | 90 | 88 | 2 | 90 | 90 | 0 | 0 |
| (Ia-2) + (B-17) 40 + 16 | 80 | 65 | 15 | 60 | 40 | 20 | 50 | 44 | 6 | 60 | 52 | 8 | 70 | 68 | 2 | 60 | 55 | 5 | 0 |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 5

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-3) + (B-1) 20 + 250 | 100 | 30 | 70 | 100 | 40 | 60 | 90 | 64 | 26 | 90 | 30 | 60 | 100 | 40 | 60 | 90 | 30 | 60 | 0 |
| (Ia-3) + (B-10) 40 + 250 | 100 | 100 | 0 | 100 | 76 | 24 | 70 | 51 | 19 | 60 | 50 | 10 | 80 | 60 | 20 | 60 | 40 | 20 | 0 |
| (Ia-3) + (B-7) 40 + 250 | 100 | 90 | 10 | 100 | 76 | 24 | 100 | 58 | 42 | 60 | 50 | 10 | 70 | 60 | 10 | 60 | 40 | 20 | 0 |
| (Ia-3) + (B-6) 40 + 250 | 100 | 95 | 5 | 100 | 60 | 40 | 100 | 30 | 70 | 80 | 50 | 30 | 80 | 60 | 20 | 90 | 40 | 50 | 0 |
| (Ia-3) + (B-20) 40 + 250 | 50 | 50 | 0 | 70 | 64 | 6 | 50 | 30 | 20 | 60 | 50 | 10 | 60 | 60 | 0 | 60 | 40 | 20 | 0 |
| (Ia-3) + (B-3) 40 + 62 | 100 | 95 | 5 | 100 | 96 | 4 | 90 | 72 | 18 | 90 | 50 | 40 | 100 | 76 | 24 | 100 | 40 | 60 | 0 |
| (Ia-3) + (B-2) 20 + 125 | 100 | 86 | 14 | 90 | 40 | 50 | 100 | 10 | 90 | 90 | 58 | 32 | 100 | 76 | 24 | 100 | 30 | 70 | 0 |
| (Ia-3) + (B-4) 40 + 125 | 100 | 60 | 40 | 100 | 60 | 40 | 90 | 30 | 60 | 90 | 60 | 30 | 100 | 84 | 16 | 90 | 40 | 50 | 0 |
| (Ia-3) + (B-9) 40 + 250 | 100 | 100 | 0 | 100 | 68 | 32 | 80 | 44 | 36 | 50 | 50 | 0 | 70 | 60 | 10 | 50 | 40 | 10 | 0 |
| (Ia-3) + (B-14) | 70 | 60 | 10 | 70 | 68 | 2 | 50 | 44 | 6 | 80 | 80 | 0 | 80 | 80 | 0 | 80 | 76 | 4 | 0 |

TABLE 5-continued

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-3) + (B-15) 40 + 16 | 70 | 60 | 10 | 70 | 68 | 2 | 50 | 44 | 6 | 80 | 75 | 5 | 80 | 80 | 0 | 80 | 70 | 10 | 0 |
| (Ia-3) + (B-16) 40 + 10 | 60 | 50 | 10 | 60 | 60 | 0 | 50 | 44 | 6 | 90 | 90 | 0 | 90 | 88 | 2 | 90 | 88 | 2 | 0 |
| (Ia-3) + (B-17) 40 + 36 | 80 | 65 | 15 | 70 | 68 | 2 | 50 | 44 | 6 | 60 | 60 | 0 | 70 | 68 | 2 | 50 | 46 | 4 | 0 |
| 40 + 16 | | | | | | | | | | | | | | | | | | | |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 6

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-4) + (B-1) 20 + 250 | 100 | 30 | 70 | 100 | 40 | 60 | 90 | 64 | 26 | 90 | 30 | 60 | 100 | 40 | 60 | 90 | 30 | 60 | 0 |
| (Ia-4) + (B-10) 40 + 250 | 100 | 100 | 0 | 100 | 70 | 30 | 80 | 51 | 29 | 60 | 40 | 20 | 80 | 50 | 30 | 60 | 40 | 20 | 0 |
| (Ia-4) + (B-7) 40 + 250 | 100 | 90 | 10 | 100 | 70 | 30 | 100 | 58 | 42 | 60 | 40 | 20 | 70 | 50 | 20 | 70 | 40 | 30 | 0 |
| (Ia-4) + (B-6) 40 + 250 | 100 | 95 | 5 | 100 | 50 | 50 | 100 | 30 | 70 | 80 | 40 | 40 | 80 | 50 | 30 | 80 | 40 | 40 | 0 |
| (Ia-4) + (B-20) 40 + 250 | 70 | 50 | 20 | 60 | 55 | 5 | 50 | 30 | 20 | 60 | 40 | 20 | 60 | 50 | 10 | 50 | 40 | 10 | 0 |
| (Ia-4) + (B-3) 40 + 62 | 100 | 95 | 5 | 100 | 95 | 5 | 90 | 72 | 18 | 90 | 40 | 50 | 100 | 70 | 30 | 90 | 40 | 50 | 0 |
| (Ia-4) + (B-2) 20 + 125 | 100 | 88 | 12 | 90 | 30 | 60 | 100 | 10 | 90 | 90 | 52 | 38 | 100 | 72 | 28 | 100 | 20 | 80 | 0 |
| (Ia-4) + (B-4) 40 + 125 | 100 | 60 | 40 | 100 | 50 | 50 | 100 | 30 | 70 | 90 | 52 | 38 | 100 | 80 | 20 | 100 | 40 | 60 | 0 |
| (Ia-4) + (B-9) 40 + 250 | 100 | 100 | 0 | 100 | 60 | 40 | 90 | 44 | 48 | 50 | 40 | 10 | 60 | 50 | 10 | 50 | 40 | 10 | 0 |
| (Ia-4) + (B-14) 40 + 16 | 70 | 60 | 10 | 70 | 60 | 10 | 50 | 44 | 6 | 80 | 76 | 4 | 80 | 75 | 5 | 80 | 76 | 4 | 0 |
| (Ia-4) + (B-15) 40 + 10 | 70 | 60 | 10 | 60 | 60 | 0 | 50 | 44 | 6 | 70 | 70 | 0 | 80 | 75 | 5 | 80 | 70 | 10 | 0 |
| (Ia-4) + (B-16) 40 + 36 | 60 | 50 | 10 | 60 | 50 | 10 | 50 | 44 | 6 | 90 | 88 | 2 | 90 | 85 | 5 | 90 | 88 | 2 | 0 |
| (Ia-4) + (B-17) 40 + 16 | 80 | 65 | 15 | 70 | 60 | 10 | 60 | 44 | 16 | 60 | 52 | 8 | 70 | 60 | 10 | 50 | 46 | 4 | 0 |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 7

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-5) + (B-1) 20 + 250 | 100 | 40 | 60 | 100 | 30 | 70 | 90 | 64 | 26 | 90 | 20 | 70 | 100 | 30 | 70 | 90 | 20 | 70 | 0 |
| (Ia-5) + (B-10) 40 + 250 | 100 | 100 | 0 | 100 | 70 | 30 | 90 | 51 | 39 | 60 | 40 | 20 | 70 | 50 | 20 | 60 | 30 | 30 | 0 |
| (Ia-5) + (B-7) 40 + 250 | 100 | 92 | 8 | 100 | 70 | 30 | 100 | 58 | 42 | 60 | 40 | 20 | 60 | 50 | 10 | 70 | 30 | 40 | 0 |
| (Ia-5) + (B-6) 40 + 250 | 100 | 96 | 4 | 100 | 50 | 50 | 100 | 30 | 70 | 70 | 40 | 30 | 80 | 50 | 30 | 80 | 30 | 50 | 0 |
| (Ia-5) + (B-20) 40 + 250 | 60 | 60 | 0 | 60 | 55 | 5 | 50 | 30 | 20 | 50 | 40 | 10 | 60 | 50 | 10 | 50 | 30 | 20 | 0 |
| (Ia-5) + (B-3) 40 + 62 | 100 | 96 | 4 | 100 | 95 | 5 | 90 | 72 | 18 | 100 | 40 | 60 | 100 | 70 | 30 | 100 | 30 | 70 | 0 |
| (Ia-5) + (B-2) 20 + 125 | 100 | 68 | 32 | 100 | 50 | 50 | 90 | 30 | 60 | 90 | 52 | 38 | 100 | 80 | 20 | 100 | 30 | 70 | 0 |
| (Ia-5) + (B-4) 40 + 125 | 100 | 68 | 32 | 100 | 50 | 50 | 90 | 30 | 60 | 90 | 52 | 38 | 100 | 80 | 20 | 100 | 30 | 70 | 0 |
| (Ia-5) + (B-9) 40 + 250 | 100 | 100 | 0 | 100 | 60 | 40 | 90 | 44 | 46 | 60 | 40 | 20 | 60 | 50 | 10 | 50 | 30 | 20 | 0 |
| (Ia-5) + (B-14) 40 + 16 | 70 | 68 | 2 | 70 | 60 | 10 | 50 | 44 | 6 | 80 | 76 | 4 | 80 | 75 | 5 | 80 | 72 | 8 | 0 |
| (Ia-5) + (B-15) 40 + 10 | 70 | 68 | 2 | 70 | 60 | 10 | 50 | 44 | 6 | 70 | 70 | 0 | 80 | 75 | 5 | 70 | 65 | 5 | 0 |
| (Ia-5) + (B-16) 40 + 36 | 70 | 60 | 10 | 70 | 50 | 20 | 50 | 44 | 6 | 90 | 88 | 2 | 90 | 85 | 5 | 90 | 86 | 4 | 0 |
| (Ia-5) + (B-17) 40 + 16 | 80 | 72 | 8 | 70 | 60 | 10 | 70 | 44 | 26 | 60 | 52 | 8 | 70 | 60 | 10 | 50 | 37 | 13 | 0 |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 8

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-7) + (B-1) 20 + 250 | 100 | 30 | 70 | 100 | 30 | 70 | 100 | 64 | 36 | 90 | 20 | 70 | 100 | 20 | 80 | 90 | 20 | 70 | 0 |
| (Ia-7) + (B-10) 40 + 250 | 100 | 100 | 0 | 100 | 70 | 30 | 90 | 58 | 32 | 60 | 50 | 10 | 70 | 50 | 20 | 60 | 40 | 20 | 0 |
| (Ia-7) + (B-7) 40 + 250 | 100 | 88 | 12 | 100 | 70 | 30 | 100 | 64 | 36 | 60 | 50 | 10 | 70 | 50 | 20 | 70 | 40 | 30 | 0 |
| (Ia-7) + (B-6) 40 + 250 | 100 | 94 | 6 | 100 | 50 | 50 | 100 | 40 | 60 | 80 | 50 | 30 | 80 | 50 | 30 | 70 | 40 | 30 | 0 |
| (Ia-7) + (B-20) 40 + 250 | 60 | 40 | 20 | 60 | 55 | 5 | 50 | 40 | 10 | 60 | 50 | 10 | 60 | 50 | 10 | 50 | 40 | 10 | 0 |
| (Ia-7) + (B-3) 40 + 62 | 100 | 94 | 6 | 100 | 95 | 5 | 90 | 76 | 14 | 100 | 50 | 50 | 100 | 70 | 30 | 100 | 40 | 60 | 0 |
| (Ia-7) + (B-2) 20 + 125 | 100 | 86 | 14 | 100 | 30 | 70 | 100 | 30 | 70 | 100 | 52 | 48 | 100 | 68 | 32 | 90 | 20 | 70 | 0 |
| (Ia-7) + (B-4) 40 + 125 | 100 | 52 | 48 | 100 | 50 | 50 | 90 | 40 | 50 | 90 | 60 | 30 | 100 | 80 | 20 | 90 | 40 | 50 | 0 |
| (Ia-7) + (B-9) 40 + 250 | 100 | 100 | 0 | 100 | 60 | 40 | 90 | 52 | 38 | 60 | 50 | 10 | 60 | 50 | 10 | 50 | 40 | 10 | 0 |
| (Ia-7) + (B-14) | 60 | 52 | 8 | 70 | 60 | 10 | 60 | 52 | 8 | 80 | 80 | 0 | 80 | 75 | 5 | 80 | 76 | 4 | 0 |

TABLE 8-continued

Foliar treatment
(combined use of active ingredients)

| Dosage of each active ingredient (g/ha) | herbicidal efficacy (%) | | | | | | | | | | | | | | | | | | phyto- toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| 40 + 16 (Ia-7) + (B-15) | 70 | 52 | 18 | 70 | 60 | 10 | 60 | 52 | 8 | 80 | 50 | 30 | 80 | 50 | 30 | 70 | 70 | 0 | 0 |
| 40 + 10 (Ia-7) + (B-16) | 50 | 40 | 10 | 70 | 50 | 20 | 60 | 52 | 8 | 90 | 90 | 0 | 90 | 85 | 5 | 90 | 88 | 2 | 0 |
| 40 + 36 (Ia-7) + (B-17) | 80 | 58 | 22 | 80 | 60 | 20 | 70 | 52 | 18 | 60 | 60 | 0 | 70 | 60 | 10 | 50 | 46 | 4 | 0 |
| 40 + 16 | | | | | | | | | | | | | | | | | | | |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

Tables 3–8 show that all the compositions containing Compound (Ia-1) and one of Compounds (B-1), (B-6), (B-7), (B-10) and (B-20) in combination and all the compositions containing one of Compounds (Ia-2)–(Ia-5) and (Ia-7) and one of Compounds (B-1)–(B-4), (B-6), (B-7), (B-9), (B-10) and (B-14)–(B-17) in combination showed synergistic herbicidal effects on all the weeds used for the test.

That is, in the compositions containing Compound (Ia-1) and one of Compounds (B-1), (B-10), (B-6) and (B-20), the composition containing Compound (Ia-1) and Compound (B-1) showed a high synergistic effect on velvet leaf in particular, the composition containing Compound (Ia-1) and Compound (B-10) showed a high synergistic effect on velvet leaf and barnyard grass in particular, the composition containing Compound (Ia-1) and Compound (B-7) showed a high synergistic effect on slender amaranth and green foxtail in particular, the composition containing Compound (Ia-1) and Compound (B-6) showed a high synergistic effect on velvet leaf and slender amaranth in particular, and the composition containing Compound (Ia-1) and Compound (B-20) showed a high synergistic effect on velvet leaf in particular.

Further, the compositions containing Compound (Ia-1) and Compound (B-1), (B-10) or (B-6) showed a herbicidal effect at an earlier stage than any individual herbicide used as a single active ingredient.

In the compositions containing Compound (Ia-2) and one of Compounds (B-1)–(B-4), (B-6), (B-7), (B-9), (B-10) and (B-14)–(B-17), the composition containing Compound (Ia-2) and Compound (B-1) showed a high synergistic effect on cocklebur, velvet leaf, green foxtail, crabgrass and barnyard grass in particular, the composition containing Compound (Ia-2) and Compound (B-10) showed a high synergistic effect on green foxtail in particular, the composition containing Compound (Ia-2) and Compound (B-7) showed a high synergistic effect on velvet leaf in particular, the composition containing Compound (Ia-2) and Compound (B-6) showed a high synergistic effect on velvet leaf and slender amaranth in particular, the composition containing Compound (Ia-2) and Compound (B-20) showed a high synergistic effect on slender amaranth in particular, the composition containing Compound (Ia-2) and Compound (B-3) showed a high synergistic effect on green foxtail and barnyard grass in particular, the composition containing Compound (Ia-2) and Compound (B-2) showed a high synergistic effect on slender amaranth and barnyard grass in particular, the composition containing Compound (Ia-2) and Compound (B-4) showed a high synergistic effect on velvet leaf, slender amaranth and barnyard grass in particular, the composition containing Compound (Ia-2) and Compound (B-9) showed a high synergistic effect on velvet leaf in particular, the composition containing Compound (Ia-2) and Compound (B-14) showed a high synergistic effect on cocklebur in particular, the composition containing Compound (Ia-2) and Compound (B-15) showed a high synergistic effect on cocklebur and green foxtail in particular, the composition containing Compound (Ia-2) and Compound (B-16) showed a high synergistic effect on cocklebur in particular, and the composition containing Compound (Ia-2) and Compound (B-17) showed a high synergistic effect on cocklebur and velvet leaf in particular.

In the compositions containing Compound (Ia-3) and one of Compounds (B-1)–(B-4), (B-6), (B-7), (B-9), (B-10) and (B-14)–(B-17), the composition containing Compound (Ia-3) and Compound (B-1) showed a high synergistic effect on cocklebur, velvet leaf, green foxtail, crabgrass and barnyard grass in particular, the composition containing Compound (Ia-3) and Compound (B-10) showed a high synergistic effect on velvet leaf in particular, the composition containing Compound (Ia-3) and Compound (B-7) showed a high synergistic effect on slender amaranth in particular, the composition containing Compound (Ia-3) and Compound (B-6) showed a high synergistic effect on slender amaranth and barnyard grass in particular, the composition containing Compound (Ia-3) and Compound (B-20) showed a high synergistic effect on slender amaranth and barnyard grass in particular, the composition containing Compound (Ia-3) and Compound (B-3) showed a high synergistic effect on green foxtail and barnyard grass in particular, the composition containing Compound (Ia-3) and Compound (B-2) showed a high synergistic effect on velvet leaf, slender amaranth and barnyard grass in particular, the composition containing Compound (Ia-3) and Compound (B-4) showed a high synergistic effect on slender amaranth and barnyard grass in particular, the composition containing Compound (Ia-3) and Compound (B-9) showed a high synergistic effect on velvet leaf and slender amaranth in particular, the composition containing Compound (Ia-3) and Compound (B-14) showed a high synergistic effect on cocklebur in particular, the composition containing Compound (Ia-3) and Compound (B-15) showed a high synergistic effect on cocklebur and barnyard grass in particular, the composition containing Compound (Ia-3) and Compound (B-16) showed a high synergistic effect on cocklebur in particular, and the composition containing Compound (Ia-3) and Compound (B-17) showed a high synergistic effect on cocklebur in particular.

In the compositions containing Compound (Ia-4) and one of Compounds (B-1)~(B-4), (B-6), (B-7), (B-9), (B-10) and (B-14)~(B-17), the composition containing Compound (Ia-4) and Compound (B-1) showed a high synergistic effect on cocklebur, velvet leaf, green foxtail, crabgrass and barnyard grass in particular, the composition containing Compound (Ia-4) and Compound (B-10) showed a high synergistic effect on velvet leaf, slender amaranth and crabgrass in particular, the composition containing Compound (Ia-4) and Compound (B-7) showed a high synergistic effect on slender amaranth in particular, the composition containing Compound (Ia-4) and Compound (B-6) showed a high synergistic effect on velvet leaf and slender amaranth in particular, the composition containing Compound (Ia-4) and Compound (B-20) showed a high synergistic effect on cocklebur, slender amaranth and green foxtail in particular, the composition containing Compound (Ia-4) and Compound (B-3) showed a high synergistic effect on green foxtail and barnyard grass in particular, the composition containing Compound (Ia-4) and Compound (B-2) showed a high synergistic effect on velvet leaf, slender amaranth and barnyard grass in particular, the composition containing Compound (Ia-4) and Compound (B-4) showed a high synergistic effect on velvet leaf, slender amaranth and barnyard grass in particular, the composition containing Compound (Ia-4) and Compound (B-9) showed a high synergistic effect on velvet leaf in particular, the composition containing Compound (Ia-4) and Compound (B-14) showed a high synergistic effect on cocklebur in particular, the composition containing Compound (Ia-4) and Compound (B-15) showed a high synergistic effect on cocklebur and barnyard grass in particular, the composition containing Compound (Ia-4) and Compound (B-16) showed a high synergistic effect on cocklebur and velvet leaf in particular, and the composition containing Compound (Ia-4) and Compound (B-17) showed a high synergistic effect on cocklebur and slender amaranth in particular.

In the compositions containing Compound (Ia-5) and one of Compounds (B-1)~(B-4), (B-6), (B-7), (B-9), (B-10) and (B-14)~(B-17), the composition containing Compound (Ia-5) and Compound (B-1) showed a high synergistic effect on cocklebur, velvet leaf, green foxtail, crabgrass and barnyard grass in particular, the composition containing Compound (Ia-5) and Compound (B-10) showed a high synergistic effect on velvet leaf, slender amaranth and barnyard grass in particular, the composition containing Compound (Ia-5) and Compound (B-7) showed a high synergistic effect on velvet leaf, slender amaranth and barnyard grass in particular, the composition containing Compound (Ia-5) and Compound (B-6) showed a high synergistic effect on velvet leaf, slender amaranth and barnyard grass in particular, the composition containing Compound (Ia-5) and Compound (B-20) showed a high synergistic effect on slender amaranth and barnyard grass in particular, the composition containing Compound (Ia-5) and Compound (B-3) showed a high synergistic effect on green foxtail and barnyard grass in particular, the composition containing Compound (Ia-5) and Compound (B-2) showed a high synergistic effect on velvet leaf, slender amaranth and barnyard grass in particular, the composition containing Compound (Ia-5) and Compound (B-4) showed a high synergistic effect on velvet leaf, slender amaranth and barnyard grass in particular, the composition containing Compound (Ia-5) and Compound (B-9) showed a high synergistic effect on velvet leaf and slender amaranth in particular, the composition containing Compound (Ia-5) and Compound (B-14)showed a high synergistic effect on velvet leaf in particular, the composition containing Compound (Ia-5) and Compound (B-15) showed a high synergistic effect on velvet leaf in particular, the composition containing Compound (Ia-5) and Compound (B-16) showed a high synergistic effect on velvet leaf in particular, and the composition containing Compound (Ia-5) and Compound (B-17) showed a high synergistic effect on slender amaranth in particular.

In the compositions containing Compound (Ia-7) and one of Compounds (B-1)~(B-4), (B-6), (B-7), (B-9), (B-10) and (B-14)~(B-17), the composition containing Compound (Ia-7) and Compound (B-1) showed a high synergistic effect on cocklebur, velvet leaf, green foxtail, crabgrass and barnyard grass in particular, the composition containing Compound (Ia-7) and Compound (B-10) showed a high synergistic effect on velvet leaf and slender amaranth in particular, the composition containing Compound (Ia-7) and Compound (B-7) showed a high synergistic effect on velvet leaf, slender amaranth and barnyard grass in particular, the composition containing Compound (Ia-7) and Compound (B-6) showed a high synergistic effect on velvet leaf, slender amaranth in particular, the composition containing Compound (Ia-7) and Compound (B-20) showed a high synergistic effect on cocklebur in particular, the composition containing Compound (Ia-7) and Compound (B-3) showed a high synergistic effect on green foxtail and barnyard grass in particular, the composition containing Compound (Ia-7) and Compound (B-2) showed a high synergistic effect on velvet leaf, slender amaranth and barnyard grass in particular, the composition containing Compound (Ia-7) and Compound (B-4) showed a high synergistic effect on cocklebur, velvet leaf, slender amaranth and barnyard grass in particular, the composition containing Compound (Ia-7) and Compound (B-9) showed a high synergistic effect on velvet leaf and slender amaranth in particular, the composition containing Compound (Ia-7) and Compound (B-14) showed a high synergistic effect on cocklebur, velvet leaf and slender amaranth in particular, the composition containing Compound (Ia-7) and Compound (B-15) showed a high synergistic effect on crabgrass in particular, the composition containing Compound (Ia-7) and Compound (B-16) showed a high synergistic effect on velvet leaf in particular, and the composition containing Compound (Ia-7) and Compound (B-17) showed a high synergistic effect on cocklebur, velvet leaf and slender amaranth in particular.

Table 9 shows the results of foliar treatment tests of single active ingredients of Compounds (Ib-1), (Ib-2), (Ib-3) and Compounds (B-1)~(B-10) and (B-14)~(B-17).

Tables 10 to 12 show the results of foliar treatment tests of compositions containing one of Compounds (Ib-1), (Ib-2) and (Ib-3) and one of Compounds (B-1)~(B-10) and (B-14)~(B-17).

TABLE 9

Foliar treatment
(single active ingredient)

| Compd | Dosage (g/ha) | (a) | (b) | (c) | (d) | (e) | (f) | phytotoxicity to corn |
|---|---|---|---|---|---|---|---|---|
| (Ib-1) | 40 | 60 | 20 | 20 | 40 | 60 | 40 | 0 |
|  | 20 | 40 | 10 | 20 | 20 | 40 | 20 | 0 |
| (Ib-2) | 40 | 50 | 30 | 30 | 40 | 60 | 40 | 0 |
|  | 20 | 30 | 20 | 20 | 20 | 40 | 20 | 0 |
| (Ib-3) | 40 | 50 | 30 | 20 | 50 | 60 | 40 | 0 |
|  | 20 | 40 | 20 | 20 | 20 | 40 | 30 | 0 |
| (B-1) | 250 | 20 | 0 | 0 | 0 | 0 | 0 | 0 |
| (B-2) | 125 | 80 | 0 | 0 | 40 | 60 | 0 | 0 |
| (B-3) | 62 | 90 | 90 | 60 | 0 | 40 | 0 | 0 |
| (B-4) | 125 | 20 | 0 | 0 | 20 | 60 | 0 | 0 |
| (B-5) | 62 | 20 | 20 | 0 | 0 | 0 | 0 | 0 |
| (B-6) | 250 | 20 | 0 | 20 | 0 | 0 | 0 | 0 |
| (B-7) | 125 | 90 | 90 | 40 | 0 | 0 | 0 | 0 |
| (B-8) | 250 | 90 | 0 | 0 | 0 | 0 | 0 | 0 |
| (B-9) | 250 | 90 | 20 | 40 | 0 | 0 | 0 | 0 |
| (B-10) | 250 | 90 | 80 | 0 | 0 | 20 | 0 | 0 |
| (B-14) | 16 | 20 | 20 | 20 | 60 | 50 | 60 | 0 |
| (B-15) | 10 | 20 | 20 | 20 | 50 | 50 | 50 | 0 |
| (B-16) | 36 | 0 | 0 | 20 | 80 | 70 | 80 | 0 |
| (B-17) | 16 | 30 | 20 | 20 | 20 | 20 | 10 | 0 |

(a): Cocklebur
(b): Velvet leaf
(c): Slender amaranth
(d): Green foxtail
(e): Crabgrass
(f): Barnyard grass

TABLE 10

Foliar treatment
(combined use of active ingredients)

| Dosage of each active ingredient (g/ha) | herbicidal efficacy (%) | | | | | | | | | | | | | | | | | | phytotoxicity corn |
|---|---|---|---|---|---|---|---|---|---|---|---|---|---|---|---|---|---|---|---|
|  | (a) | | | (b) | | | (c) | | | (d) | | | (e) | | | (f) | | |  |
|  | (F) | (E) | (Δ) | (F) | (E) | (Δ) | (F) | (E) | (Δ) | (F) | (E) | (Δ) | (F) | (E) | (Δ) | (F) | (E) | (Δ) |  |
| (Ib-1) + (B-1) 20 + 250 | 80 | 52 | 28 | 100 | 10 | 90 | 60 | 20 | 40 | 100 | 20 | 80 | 100 | 40 | 60 | 80 | 20 | 60 | 0 |
| (Ib-1) + (B-2) 20 + 125 | 100 | 88 | 12 | 100 | 10 | 90 | 80 | 20 | 60 | 100 | 52 | 48 | 100 | 76 | 24 | 80 | 20 | 60 | 0 |
| (Ib-1) + (B-3) 40 + 62 | 100 | 96 | 4 | 100 | 92 | 8 | 100 | 68 | 32 | 100 | 40 | 60 | 100 | 76 | 24 | 100 | 40 | 60 | 0 |
| (Ib-1) + (B-4) 40 + 125 | 100 | 68 | 32 | 100 | 20 | 80 | 80 | 20 | 60 | 90 | 52 | 38 | 100 | 84 | 16 | 100 | 40 | 60 | 0 |
| (Ib-1) + (B-5) 20 + 62 | 100 | 52 | 48 | 100 | 28 | 72 | 40 | 20 | 20 | 80 | 20 | 60 | 80 | 40 | 40 | 80 | 20 | 60 | 0 |
| (Ib-1) + (B-6) 40 + 250 | 100 | 68 | 32 | 100 | 20 | 80 | 100 | 36 | 64 | 90 | 40 | 50 | 100 | 60 | 40 | 90 | 40 | 50 | 0 |
| (Ib-1) + (B-7) | 100 | 96 | 4 | 100 | 92 | 8 | 100 | 52 | 48 | 40 | 40 | 0 | 60 | 60 | 0 | 40 | 40 | 0 | 0 |

TABLE 10-continued

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| 40 + 125 (Ib-1) + (B-8) | 100 | 90 | 10 | 100 | 20 | 80 | 60 | 20 | 40 | 100 | 40 | 60 | 100 | 60 | 40 | 80 | 40 | 40 | 0 |
| 20 + 250 (Ib-1) + (B-9) | 100 | 96 | 4 | 80 | 36 | 44 | 100 | 36 | 64 | 60 | 40 | 20 | 80 | 60 | 20 | 40 | 40 | 0 | 0 |
| 40 + 250 (Ib-1) + (B-10) | 100 | 96 | 4 | 100 | 84 | 16 | 40 | 20 | 20 | 90 | 40 | 50 | 90 | 68 | 22 | 80 | 40 | 40 | 0 |
| 40 + 250 (Ib-1) + (B-14) | 80 | 68 | 12 | 60 | 36 | 24 | 40 | 36 | 4 | 80 | 76 | 4 | 80 | 80 | 0 | 80 | 76 | 4 | 0 |
| 40 + 16 (Ib-1) + (B-15) | 70 | 68 | 2 | 40 | 36 | 4 | 40 | 36 | 4 | 80 | 70 | 10 | 80 | 80 | 0 | 80 | 70 | 10 | 0 |
| 40 + 10 (Ib-1) + (B-16) | 70 | 60 | 10 | 40 | 20 | 20 | 40 | 36 | 4 | 90 | 80 | 2 | 90 | 88 | 2 | 90 | 88 | 2 | 0 |
| 40 + 36 (Ib-1) + (B-17) | 80 | 72 | 8 | 40 | 36 | 4 | 40 | 36 | 4 | 60 | 52 | 8 | 70 | 68 | 2 | 50 | 48 | 2 | 0 |
| 40 + 16 | | | | | | | | | | | | | | | | | | | |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 11

Foliar treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ib-2) + (B-1) 20 + 250 | 90 | 44 | 46 | 100 | 20 | 80 | 60 | 20 | 40 | 90 | 20 | 70 | 100 | 40 | 60 | 90 | 20 | 70 | 0 |
| (Ib-2) + (B-2) 20 + 125 | 100 | 86 | 14 | 90 | 20 | 70 | 90 | 20 | 70 | 90 | 52 | 38 | 100 | 76 | 24 | 80 | 20 | 60 | 0 |
| (Ib-2) + (B-3) 40 + 62 | 100 | 95 | 5 | 100 | 93 | 7 | 100 | 72 | 28 | 100 | 40 | 60 | 100 | 76 | 24 | 100 | 40 | 60 | 0 |
| (Ib-2) + (B-4) 40 + 125 | 100 | 60 | 40 | 100 | 30 | 70 | 80 | 30 | 50 | 100 | 52 | 48 | 90 | 84 | 6 | 100 | 40 | 60 | 0 |
| (Ib-2) + (B-5) 20 + 62 | 100 | 44 | 56 | 90 | 36 | 54 | 40 | 20 | 20 | 80 | 20 | 60 | 90 | 40 | 50 | 80 | 20 | 60 | 0 |
| (Ib-2) + (B-6) 40 + 250 | 100 | 60 | 40 | 90 | 30 | 60 | 100 | 44 | 56 | 90 | 40 | 50 | 100 | 60 | 40 | 90 | 40 | 50 | 0 |
| (Ib-2) + (B-7) 40 + 125 | 100 | 95 | 5 | 100 | 93 | 7 | 90 | 58 | 32 | 60 | 40 | 20 | 80 | 60 | 20 | 60 | 40 | 20 | 0 |
| (Ib-2) + (B-8) 20 + 250 | 100 | 95 | 5 | 100 | 30 | 70 | 60 | 20 | 40 | 90 | 40 | 50 | 90 | 60 | 30 | 90 | 40 | 50 | 0 |
| (Ib-2) + (B-9) 40 + 250 | 100 | 95 | 5 | 90 | 44 | 46 | 100 | 44 | 56 | 60 | 40 | 20 | 80 | 60 | 20 | 40 | 40 | 0 | 0 |
| (Ib-2) + (B-10) 40 + 250 | 100 | 95 | 5 | 100 | 86 | 14 | 50 | 30 | 20 | 90 | 40 | 50 | 90 | 68 | 22 | 80 | 40 | 50 | 0 |
| (Ib-2) + (B-14) 40 + 16 | 60 | 60 | 0 | 50 | 44 | 6 | 50 | 44 | 6 | 80 | 76 | 4 | 80 | 80 | 0 | 80 | 76 | 4 | 0 |
| (Ib-2) + (B-15) 40 + 10 | 70 | 60 | 10 | 50 | 44 | 6 | 70 | 44 | 26 | 80 | 70 | 10 | 80 | 80 | 0 | 80 | 70 | 10 | 0 |
| (Ib-2) + (B-16) 40 + 36 | 60 | 50 | 10 | 40 | 30 | 10 | 50 | 44 | 6 | 90 | 88 | 2 | 90 | 88 | 2 | 90 | 88 | 2 | 0 |
| (Ib-2) + (B-17) 40 + 16 | 80 | 65 | 15 | 50 | 44 | 6 | 50 | 44 | 6 | 60 | 52 | 8 | 70 | 68 | 2 | 50 | 48 | 2 | 0 |

(a): Cocklebur
(b): Velvet leaf
(c): Slender amaranth

TABLE 11-continued

Foliar treatment
(combined use of active ingredients)

| Dosage of each active ingredient (g/ha) | herbicidal efficacy (%) | | | | | | | | | | | | | | | | | | phyto- toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |

(d): Green foxtail
(e): Crabgrass
(f): Barnyard grass
Difference (Δ) = Found value(F) - Expected value(E)
A larger difference (Δ) means a larger synergistic effect due to the combined use of active ingredients.

TABLE 12

Foliar treatment
(combined use of active ingredients)

| Dosage of each active ingredient (g/ha) | herbicidal efficacy (%) | | | | | | | | | | | | | | | | | | phyto- toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ib-3) + (B-1) 20 + 250 | 90 | 52 | 32 | 100 | 20 | 80 | 70 | 20 | 50 | 90 | 20 | 70 | 100 | 40 | 60 | 100 | 30 | 70 | 0 |
| (Ib-3) + (B-2) 20 + 125 | 100 | 88 | 12 | 100 | 20 | 80 | 100 | 20 | 80 | 100 | 52 | 48 | 100 | 76 | 24 | 80 | 30 | 50 | 0 |
| (Ib-3) + (B-3) 40 + 62 | 100 | 95 | 5 | 100 | 93 | 7 | 100 | 68 | 32 | 100 | 50 | 50 | 100 | 76 | 24 | 90 | 40 | 50 | 0 |
| (Ib-3) + (B-4) 40 + 125 | 100 | 60 | 40 | 90 | 30 | 60 | 90 | 20 | 70 | 90 | 60 | 30 | 100 | 84 | 16 | 100 | 40 | 60 | 0 |
| (Ib-3) + (B-5) 20 + 62 | 90 | 52 | 38 | 90 | 36 | 54 | 40 | 20 | 20 | 90 | 20 | 70 | 90 | 40 | 50 | 90 | 30 | 60 | 0 |
| (Ib-3) + (B-6) 40 + 250 | 100 | 60 | 40 | 90 | 30 | 60 | 100 | 36 | 64 | 100 | 50 | 50 | 100 | 60 | 40 | 90 | 40 | 50 | 0 |
| (Ib-3) + (B-7) 40 + 125 | 100 | 95 | 5 | 100 | 93 | 7 | 70 | 52 | 18 | 70 | 50 | 20 | 80 | 60 | 20 | 70 | 40 | 30 | 0 |
| (Ib-3) + (B-8) 20 + 250 | 100 | 95 | 5 | 100 | 30 | 70 | 60 | 20 | 40 | 100 | 50 | 50 | 100 | 60 | 40 | 80 | 40 | 40 | 0 |
| (Ib-3) + (B-9) 40 + 250 | 100 | 95 | 5 | 90 | 44 | 46 | 100 | 36 | 64 | 60 | 50 | 10 | 80 | 60 | 20 | 70 | 40 | 30 | 0 |
| (Ib-3) + (B-10) 40 + 250 | 100 | 95 | 5 | 100 | 86 | 14 | 80 | 20 | 60 | 90 | 50 | 40 | 90 | 60 | 30 | 80 | 40 | 40 | 0 |
| (Ib-3) + (B-14) 40 + 16 | 60 | 60 | 0 | 50 | 44 | 6 | 40 | 36 | 4 | 80 | 80 | 0 | 80 | 80 | 0 | 80 | 76 | 4 | 0 |
| (Ib-3) + (B-15) 40 + 10 | 70 | 60 | 10 | 50 | 44 | 6 | 40 | 36 | 4 | 80 | 75 | 5 | 90 | 80 | 10 | 80 | 70 | 10 | 0 |
| (Ib-3) + (B-16) 40 + 36 | 70 | 50 | 20 | 50 | 30 | 20 | 50 | 36 | 14 | 90 | 90 | 0 | 90 | 88 | 2 | 90 | 88 | 2 | 0 |
| (Ib-3) + (B-17) 40 + 16 | 80 | 65 | 15 | 50 | 44 | 6 | 40 | 36 | 4 | 70 | 60 | 10 | 70 | 68 | 2 | 50 | 46 | 2 | 0 |

(a): Cocklebur
(b): Velvet leaf
(c): Slender amaranth
(d): Green foxtail
(e): Crabgrass
(f): Barnyard grass
Difference (Δ) = Found value(F) - Expected value(E)
A larger difference (Δ) means a larger synergistic effect due to the combined use of active ingredients.

Tables 10, 11 and 12 show that all the compositions containing Compound one of Compounds (Ib-1), (Ib-2) and (Ib-3) and one of Compounds (B-1)~(B-10) and (B-14)~(B-17) in combination showed high synergistic herbicidal effects on all the weeds used for the test.

That is, in the compositions containing Compound (Ib-1) and one of Compounds (B-1)~(B-10) and (B-14)~(B-17), the composition containing Compound (Ib-1) and Compound (B-1) showed a high synergistic effect on velvet leaf, green foxtail, crabgrass and barnyard grass in particular, the composition containing Compound (Ib-1) and Compound (B-2) or (B-4) showed a high synergistic effect on velvet leaf, slender amaranth and barnyard grass in particular, the composition containing Compound (Ib-1) and Compound (B-3) showed a high synergistic effect on green foxtail and barnyard grass in particular, the composition containing Compound (Ib-1) and Compound (B-5) showed a high synergistic effect on velvet leaf, green foxtail and barnyard grass in particular, the composition containing Compound (Ib-1) and Compound (B-6) showed a high synergistic effect on velvet leaf, slender amaranth, green foxtail and barnyard grass in particular, the composition containing Compound (Ib-1) and Compound (B-7) showed a high synergistic effect on slender amaranth in particular, the composition containing Compound (Ib-1) and Compound (B-8) showed a high synergistic effect on velvet leaf and green foxtail in particular, the composition containing Compound (Ib-1) and Compound (B-9) showed a high synergistic effect on slender amaranth in particular, the composition containing Compound (Ib-1) and Compound (B-10) showed a high synergistic effect on green foxtail in particular, and the composition containing Compound (Ib-1) and Compound (B-14) or (B-16) showed a high synergistic effect on velvet leaf in particular.

In the compositions containing Compound (Ib-2) and one of Compounds (B-1)~(B-10) and (B-14)~(B-17), the composition containing Composition (Ib-2) and Compound (B-1) showed a high synergistic effect on velvet leaf, green foxtail, crabgrass and barnyard grass in particular, the composition containing Compound (Ib-2) and Compound (B-2) or (B-4) showed a high synergistic effect on velvet leaf, slender amaranth and barnyard grass in particular, the composition containing Compound (Ib-2) and Compound (B-3) showed a high synergistic effect on green foxtail and barnyard grass in particular, the composition containing Compound (Ib-2) and Compound (B-5) showed a high synergistic effect on cocklebur, velvet leaf, green foxtail, crabgrass and barnyard grass in particular, the composition containing Compound (Ib-2) and Compound (B-6) showed a high synergistic effect on velvet leaf, slender amaranth, green foxtail and barnyard grass in particular, the composition containing Compound (Ib-2) and Compound (B-7) showed a high synergistic effect on slender amaranth in particular, the composition containing Compound (Ib-2) and Compound (B-8) showed a high synergistic effect on velvet leaf, green foxtail and barnyard grass in particular, the composition containing Compound (Ib-2) and Compound (B-9) showed a high synergistic effect on slender amaranth in particular, the composition containing Compound (Ib-2) and Compound (B-10) showed a high synergistic effect on green foxtail and barnyard grass in particular, and the composition containing Compound (Ib-2) and Compound (B-15) showed a high synergistic effect on slender amaranth in particular.

In the compositions containing Compound (Ib-3) and one of Compounds (B-1)~(B-10) and (B-14)~(B-17), the composition containing Compound (Ib-3) and Compound (B-1) showed a high synergistic effect on velvet leaf, slender amaranth, green foxtail, crabgrass and barnyard grass in particular, the composition containing Compound (Ib-3) and Compound (B-2) or (B-4) showed a high synergistic effect on velvet leaf, slender amaranth and barnyard grass in particular, the composition containing Compound (Ib-3) and Compound (B-3) showed a high synergistic effect on green foxtail and barnyard grass in particular, the composition containing Compound (Ib-3) and Compound (B-5) showed e high synergistic effect on velvet leaf, green foxtail, crabgrass and barnyard grass in particular, the composition containing Compound (Ib-3) and Compound (B-6) showed a high synergistic effect on velvet leaf, slender amaranth, green foxtail and barnyard grass in particular, the composition containing Compound (Ib-3) and Compound (B-7) showed a high synergistic effect on barnyard grass in particular, the composition containing Compound (Ib-3) and Compound (B-8) showed a high synergistic effect on velvet leaf and green foxtail in particular, the composition containing Compound (Ib-3) and Compound (B-9) or (B-10) showed a high synergistic effect on slender amaranth in particular, the composition containing Compound (Ib-3) and Compound (B-16) showed a high synergistic effect on cocklebur and velvet leaf in particular, and the composition containing Compound (Ib-3) and Compound (B-17) showed a high synergistic effect on cocklebur in particular.

Further, the compositions containing Compound (Ib-1), (Ib-2) or (Ib-3) and one of Compounds (B-1)~(B-6) showed a herbicidal effect at an earlier stage than any individual herbicide used as a single active ingredient.

Table 13 shows the results of foliar treatment tests on single active ingredients of Compound (Ic-1) and Compounds (B-1)~(B-4), (B-6)~(B-10) and (b-14)~(B-17).

Table 14 shows the results of foliar treatment tests on compositions of Compound (Ic-1) and one of Compounds (B-1)~(B-4), (B-6)~(B-10) and (b-14)~(B-17).

TABLE 13

Foliar treatment (single active ingredient)

| Compd | Dosage (g/ha) | herbicidal efficacy % | | | | | | phytotoxicity to corn |
|---|---|---|---|---|---|---|---|---|
| | | (a) | (b) | (c) | (d) | (e) | (f) | |
| (Ic-1) | 40 | 20 | 20 | 0 | 20 | 20 | 20 | 0 |
| | 20 | 0 | 0 | 0 | 0 | 0 | 0 | 0 |
| (B-1) | 250 | 0 | 20 | 40 | 0 | 20 | 0 | 0 |
| (B-2) | 250 | 0 | 0 | 0 | 20 | 80 | 0 | 0 |
| (B-3) | 125 | 80 | 80 | 80 | 80 | 20 | 80 | 0 |
| (B-4) | 500 | 80 | 90 | 60 | 40 | 60 | 0 | 0 |
| (B-6) | 250 | 0 | 0 | 0 | 0 | 0 | 0 | 0 |
| (B-7) | 125 | 80 | 90 | 40 | 0 | 0 | 0 | 0 |
| (b-8) | 125 | 90 | 0 | 0 | 0 | 0 | 0 | 0 |
| (B-9) | 125 | 90 | 0 | 40 | 0 | 0 | 0 | 0 |
| (B-10) | 125 | 20 | 10 | 0 | 0 | 20 | 0 | 0 |
| (B-14) | 16 | 20 | 20 | 20 | 60 | 50 | 60 | 0 |
| (B-15) | 10 | 10 | 10 | 20 | 50 | 60 | 50 | 0 |
| (B-16) | 36 | 0 | 0 | 20 | 80 | 70 | 80 | 0 |
| (B-17) | 16 | 30 | 20 | 20 | 20 | 20 | 10 | 0 |

(a): Cocklebur
(b): Velvet leaf
(c): Slender amaranth
(d): Green foxtail
(e): Crabgrass
(f): Barnyard grass

TABLE 14

Foliar treatment
(combined use of active ingredients)

| Dosage of each active ingredient (g/ha) | herbicidal efficacy (%) | | | | | | | | | | | | | | | | | | phytotoxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ic-1) + (B-1) 40 + 250 | 100 | 20 | 80 | 100 | 20 | 80 | 60 | 40 | 20 | 40 | 20 | 20 | 100 | 36 | 64 | 30 | 20 | 10 | 0 |
| (Ic-1) + (B-2) 40 + 250 | 100 | 20 | 80 | 100 | 20 | 80 | 20 | 0 | 20 | 80 | 36 | 44 | 100 | 80 | 20 | 80 | 20 | 60 | 0 |
| (Ic-1) + (B-3) 40 + 125 | 100 | 84 | 16 | 100 | 84 | 16 | 100 | 80 | 20 | 80 | 20 | 60 | 40 | 20 | 20 | 80 | 20 | 60 | 0 |
| (Ic-1) + (B-4) 40 + 500 | 100 | 84 | 16 | 100 | 92 | 8 | 100 | 60 | 40 | 90 | 52 | 38 | 100 | 68 | 32 | 60 | 20 | 40 | 0 |
| (Ic-1) + (B-6) 40 + 250 | 100 | 20 | 80 | 100 | 20 | 80 | 20 | 0 | 20 | 20 | 20 | 0 | 100 | 20 | 80 | 20 | 20 | 0 | 0 |
| (Ic-1) + (B-7) 40 + 125 | 100 | 84 | 16 | 100 | 92 | 8 | 100 | 40 | 60 | 50 | 20 | 30 | 20 | 20 | 0 | 20 | 20 | 0 | 0 |
| (Ic-1) + (B-8) 40 + 125 | 100 | 92 | 8 | 20 | 20 | 0 | 100 | 0 | 100 | 60 | 20 | 40 | 60 | 20 | 40 | 40 | 20 | 20 | 0 |
| (Ic-1) + (B-9) 20 + 125 | 100 | 90 | 10 | 40 | 0 | 40 | 100 | 40 | 60 | 0 | 0 | 0 | 20 | 0 | 20 | 0 | 0 | 0 | 0 |
| (Ic-1) + (B-10) 40 + 125 | 100 | 36 | 64 | 100 | 28 | 72 | 20 | 0 | 20 | 60 | 20 | 40 | 80 | 36 | 44 | 60 | 20 | 40 | 0 |
| (Ic-1) + (B-14) 40 + 16 | 40 | 36 | 4 | 40 | 36 | 4 | 40 | 20 | 20 | 70 | 68 | 2 | 80 | 60 | 20 | 70 | 68 | 2 | 0 |
| (Ic-1) + (B-15) 40 + 10 | 60 | 27 | 33 | 100 | 27 | 23 | 40 | 20 | 20 | 70 | 60 | 10 | 80 | 62 | 18 | 80 | 60 | 20 | 0 |
| (Ic-1) + (B-16) 40 + 36 | 60 | 20 | 40 | 40 | 20 | 20 | 50 | 20 | 30 | 90 | 84 | 6 | 90 | 76 | 14 | 90 | 84 | 6 | 0 |
| (Ic-1) + (B-17) 40 + 16 | 80 | 44 | 36 | 40 | 36 | 4 | 40 | 20 | 20 | 60 | 36 | 24 | 70 | 36 | 34 | 50 | 28 | 22 | 0 |

(a): Cocklebur
(b): Velvet leaf
(c): Slender amaranth
(d): Green foxtail
(e): Crabgrass
(f): Barnyard grass
Difference (Δ) = Found value (F) − Expected value (E)
A larger difference (Δ) means a larger synergistic effect due to the combined use of active ingredients.

All the compositions containing Compound (Ic-1) and one of Compounds (B-1)~(B-4), (B-6)~(B-10) and (B-14) ~(B-17) in combination showed synergistic herbicidal effects on all the weeds used for the test.

That is, in the compositions containing Compound (Ic-1). and one of Compounds B-1)~(B-4), (B-6)~(B-10) and (B-14)~(B-17), the composition containing Compound (Ic-1) and Compound (B-1) or (B-6) showed a high synergistic effect on cocklebur, velvet leaf and crabgrass in particular, the composition containing Compound (Ic-1) and Compound (B-) showed a high synergistic effect on in particular, the composition containing Compound (Ic-1) and Compound (B-2) showed a high synergistic effect on cocklebur, velvet leaf and barnyard grass in particular, the composition containing Compound (Ic-1) and Compound (B-3) showed a high synergistic effect on green foxtail and barnyard grass in particular, the composition containing Compound (Ic-1) and Compound (B-4) showed a high synergistic effect on slender amaranth, green foxtail and barnyard grass in particular, the composition containing Compound (Ic-1) and one of Compounds (B-7)~(B-9) showed a high synergistic effect on slender amaranth in particular, the composition containing Compound (Ic-1) and Compound (B-10) showed a high synergistic effect on cocklebur and velvet leaf in particular, the composition containing Compound (Ic-1) and Compound (B-14) showed a high synergistic effect on slender amaranth and crabgrass in particular, the composition containing Compound (Ic-1) and Compound (B-15) showed a high synergistic effect on cocklebur, velvet leaf, slender amaranth and barnyard grass in particular, the composition containing Compound (Ic-1) and Compound (B-16) showed a high synergistic effect on cocklebur, velvet leaf and slender amaranth in particular, and the composition containing Compound (Ic-1) and Compound (B-17) showed a high synergistic effect on cocklebur, slender amaranth, green foxtail, crabgrass and barnyard grass in particular.

Further, the compositions containing Compound (Ic-1) and one of Compounds (B-1)~(B-4), (B-6) and (B-10) showed a herbicidal effect at an earlier stage than any individual herbicide used as a single active ingredient.

Example 2
[Soil treatment test]

Seeds of weeds such as cocklebur, velvet leaf, Slender amaranth, green foxtail, crabgrass and barnyard grass and seeds of corn were sown in 1/2,000-are Wagner pots filled with upland soil, and covered with upland soil. One day after the seeds were sown, a predetermined amount of the herbicide obtained in the same manner as in Preparation Example 5 except that one of Compounds (Ia-2)~(Ia-5), (Ia-7), (Ib-1)~(Ib-3), (Ic-1) and (Ic-2) was suspended in water and uniformly sprayed in a solution amount of 1,000 liters/hectare.

Twenty days after the treatment, the herbicide was determined for phytotoxicity to crops and herbicidal efficacy in the same manner as in the foliar treatment test. The herbicidal efficacy (weed control ratio %) was determined on the basis of the above equation (A).

Table 15 shows the results of soil treatment tests on single active ingredients of Compounds (Ia-2)~(Ia-5) and Compounds (B-2)~(B-4), (B-7), (B-11)~(B-13), (B-18) and (B-19).

Table 16 to 20 show the results of soil treatment tests on compositions of one of Compounds (Ia-2)~(Ia-5) and one of Compounds (B-2)~(B-4), (B-7), (B-11)~(B-13), (B-18) and (B-19).

TABLE 15

Soil treatment (single active ingredient)

| Compd | Dosage (g/ha) | herbicidal efficacy % | | | | | | phytotoxicity to corn |
|---|---|---|---|---|---|---|---|---|
| | | (a) | (b) | (c) | (d) | (e) | (f) | |
| (Ia-2) | 80 | 20 | 80 | 20 | 20 | 20 | 40 | 0 |
| | 40 | 0 | 60 | 0 | 10 | 20 | 40 | 0 |
| (Ia-3) | 80 | 40 | 20 | 0 | 40 | 20 | 40 | 0 |
| | 40 | 20 | 20 | 0 | 10 | 20 | 30 | 0 |
| (Ia-4) | 80 | 40 | 60 | 0 | 40 | 50 | 30 | 0 |
| | 40 | 20 | 30 | 0 | 20 | 20 | 20 | 0 |

TABLE 15-continued

Soil treatment (single active ingredient)

| Compd | Dosage (g/ha) | herbicidal efficacy % | | | | | | phytotoxicity to corn |
|---|---|---|---|---|---|---|---|---|
| | | (a) | (b) | (c) | (d) | (e) | (f) | |
| (Ia-5) | 80 | 40 | 60 | 0 | 30 | 50 | 40 | 0 |
| | 40 | 20 | 20 | 0 | 20 | 30 | 20 | 0 |
| (Ia-7) | 80 | 40 | 50 | 40 | 40 | 50 | 40 | 0 |
| | 40 | 20 | 30 | 10 | 20 | 30 | 30 | 0 |
| (B-7) | 125 | 90 | 40 | 0 | 0 | 0 | 0 | 0 |
| (B-3) | 125 | 90 | 90 | 90 | 20 | 0 | 20 | 0 |
| (B-2) | 125 | 20 | 0 | 0 | 0 | 0 | 0 | 0 |
| (B-4) | 500 | 0 | 20 | 20 | 0 | 0 | 0 | 0 |
| (B-12) | 500 | 20 | 0 | 0 | 60 | 60 | 80 | 0 |
| (B-13) | 250 | 0 | 20 | 20 | 80 | 80 | 80 | 0 |
| (B-11) | 250 | 0 | 0 | 0 | 60 | 80 | 40 | 0 |
| (B-18) | 250 | 20 | 10 | 40 | 70 | 70 | 70 | 0 |
| (B-19) | 250 | 0 | 0 | 10 | 50 | 70 | 60 | 0 |

(a): Cocklebur
(b): Velvet leaf
(c): Slender amaranth
(d): Green foxtail
(e): Crabgrass
(f): Barnyard grass

TABLE 16

Soil treatment (combined use of active ingredients)

| Dosage of each active ingredient (g/ha) | herbicidal efficacy (%) | | | | | | | | | | | | | | | | | | phytotoxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-2) + (B-7) 40 + 125 | 100 | 90 | 10 | 100 | 76 | 24 | 100 | 0 | 100 | 20 | 10 | 10 | 100 | 20 | 80 | 80 | 20 | 60 | 0 |
| (Ia-2) + (B-3) 40 + 125 | 100 | 90 | 10 | 100 | 95 | 5 | 100 | 90 | 10 | 100 | 36 | 64 | 100 | 20 | 80 | 100 | 52 | 48 | 0 |
| (Ia-2) + (B-2) 80 + 126 | 100 | 36 | 64 | 100 | 80 | 20 | 100 | 20 | 80 | 40 | 20 | 20 | 100 | 20 | 80 | 100 | 40 | 60 | 0 |
| (Ia-2) + (B-4) 40 + 500 | 90 | 20 | 70 | 100 | 84 | 16 | 100 | 20 | 80 | 40 | 20 | 20 | 60 | 20 | 40 | 100 | 40 | 60 | 0 |
| (Ia-2) + (B-12) 80 + 500 | 80 | 36 | 44 | 100 | 20 | 80 | 100 | 20 | 80 | 90 | 68 | 22 | 90 | 68 | 22 | 100 | 98 | 2 | 0 |
| (Ia-2) + (B-13) 80 + 250 | 20 | 20 | 0 | 100 | 84 | 16 | 100 | 36 | 64 | 20 | 10 | 10 | 100 | 20 | 80 | 80 | 40 | 40 | 0 |

(a): Cocklebur
(b): Velvet leaf
(c): Slender amaranth
(d): Green foxtail
(e): Crabgrass
(f): Barnyard grass
Difference (Δ) = Found value (F) − Expected value (E)
A larger difference (Δ) means a larger synergistic effect due to the combined use of active ingredients.

TABLE 17

Soil treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-3) + (B-7) 40 + 125 | 100 | 92 | 8 | 100 | 52 | 48 | 40 | 0 | 40 | 20 | 10 | 10 | 60 | 20 | 40 | 60 | 30 | 30 | 0 |
| (Ia-3) + (B-3) 40 + 125 | 100 | 92 | 8 | 100 | 92 | 8 | 100 | 90 | 10 | 90 | 28 | 62 | 100 | 20 | 80 | 100 | 44 | 56 | 0 |
| (Ia-3) + (B-2) 80 + 125 | 100 | 52 | 48 | 100 | 20 | 80 | 80 | 0 | 80 | 80 | 40 | 40 | 90 | 20 | 70 | 90 | 40 | 50 | 0 |
| (Ia-3) + (B-4) 40 + 500 | 80 | 20 | 60 | 90 | 36 | 54 | 100 | 20 | 80 | 80 | 10 | 70 | 90 | 20 | 70 | 100 | 30 | 70 | 0 |
| (Ia-3) + (B-12) 80 + 500 | 80 | 52 | 28 | 80 | 20 | 60 | 60 | 0 | 60 | 90 | 76 | 14 | 100 | 68 | 32 | 100 | 94 | 6 | 0 |
| (Ia-3) + (B-13) 80 + 250 | 50 | 40 | 10 | 80 | 36 | 44 | 80 | 20 | 60 | 100 | 88 | 12 | 100 | 84 | 16 | 100 | 94 | 6 | 0 |
| (Ia-3) + (B-11) 80 + 250 | 60 | 40 | 20 | 90 | 20 | 70 | 80 | 0 | 80 | 100 | 76 | 24 | 100 | 84 | 16 | 100 | 64 | 36 | 0 |
| (Ia-3) + (B-18) 80 + 250 | 80 | 52 | 28 | 80 | 28 | 52 | 80 | 40 | 40 | 100 | 82 | 18 | 100 | 76 | 24 | 100 | 82 | 18 | 0 |
| (Ia-3) + (B-19) 80 + 250 | 80 | 40 | 40 | 80 | 20 | 60 | 90 | 10 | 80 | 100 | 70 | 30 | 100 | 76 | 24 | 100 | 76 | 24 | 0 |

(a): Cocklebur
(b): Velvet leaf
(c): Slender amaranth
(d): Green foxtail
(e): Crabgrass
(f): Barnyard grass
Difference (Δ) = Found value (F) − Expected value (E)
A larger difference (Δ) means a larger synergistic effect due to the combined use of active ingredients.

TABLE 18

Soil treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-4) + (B-7) 40 + 125 | 100 | 92 | 8 | 100 | 58 | 42 | 40 | 0 | 40 | 40 | 20 | 20 | 50 | 20 | 30 | 50 | 20 | 30 | 0 |
| (Ia-4) + (B-3) 40 + 125 | 100 | 92 | 8 | 100 | 93 | 7 | 100 | 90 | 10 | 80 | 36 | 44 | 100 | 20 | 80 | 100 | 36 | 64 | 0 |
| (Ia-4) + (B-2) 80 + 125 | 100 | 52 | 48 | 100 | 60 | 40 | 70 | 0 | 70 | 80 | 40 | 40 | 100 | 50 | 50 | 90 | 30 | 60 | 0 |
| (Ia-4) + (B-4) 40 + 500 | 90 | 20 | 70 | 90 | 44 | 46 | 100 | 20 | 80 | 90 | 20 | 70 | 90 | 20 | 70 | 100 | 20 | 80 | 0 |
| (Ia-4) + (B-12) 80 + 500 | 90 | 52 | 38 | 90 | 60 | 30 | 60 | 0 | 60 | 90 | 76 | 14 | 100 | 80 | 20 | 100 | 93 | 7 | 0 |
| (Ia-4) + (B-13) 80 + 250 | 50 | 40 | 10 | 80 | 68 | 12 | 60 | 20 | 40 | 100 | 88 | 12 | 100 | 90 | 10 | 100 | 93 | 7 | 0 |
| (Ia-4) + (B-11) 80 + 250 | 70 | 30 | 40 | 100 | 60 | 40 | 60 | 0 | 60 | 100 | 76 | 24 | 100 | 90 | 10 | 100 | 58 | 42 | 0 |
| (Ia-4) + (B-18) 80 + 250 | 90 | 52 | 38 | 100 | 64 | 36 | 80 | 40 | 40 | 100 | 82 | 18 | 100 | 85 | 15 | 100 | 79 | 21 | 0 |
| (Ia-4) + (B-19) 80 + 250 | 90 | 40 | 50 | 80 | 60 | 20 | 100 | 10 | 90 | 100 | 70 | 30 | 100 | 85 | 15 | 100 | 72 | 28 | 0 |

(a): Cocklebur
(b): Velvet leaf
(c): Slender amaranth
(d): Green foxtail
(e): Crabgrass
(f): Barnyard grass
Difference (Δ) = Found value (F) − Expected value (E)
A larger difference (Δ) means a larger synergistic effect due to the combined use of active ingredients.

TABLE 19

Soil treatment
(combined use of active ingredients)

| Dosage of each active ingredient (g/ha) | herbicidal efficacy (%) | | | | | | | | | | | | | | | | | phyto- toxicity corn |
|---|---|---|---|---|---|---|---|---|---|---|---|---|---|---|---|---|---|---|
| | (a) | | | (b) | | | (c) | | | (d) | | | (e) | | | (f) | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-5) + (B-7) 40 + 125 | 100 | 92 | 8 | 100 | 52 | 48 | 70 | 0 | 70 | 40 | 20 | 20 | 50 | 30 | 20 | 40 | 20 | 20 | 0 |
| (Ia-5) + (B-3) 40 + 125 | 100 | 92 | 8 | 100 | 92 | 8 | 90 | 90 | 10 | 80 | 36 | 44 | 100 | 30 | 70 | 100 | 36 | 64 | 0 |
| (Ia-5) + (B-2) 80 + 125 | 100 | 52 | 48 | 100 | 60 | 40 | 80 | 60 | 20 | 90 | 30 | 60 | 100 | 50 | 50 | 90 | 40 | 50 | 0 |
| (Ia-5) + (B-4) 40 + 500 | 100 | 20 | 80 | 100 | 36 | 64 | 100 | 20 | 80 | 90 | 20 | 70 | 90 | 30 | 60 | 100 | 20 | 80 | 0 |
| (Ia-5) + (B-12) 80 + 500 | 100 | 52 | 48 | 100 | 60 | 40 | 60 | 0 | 60 | 90 | 72 | 18 | 100 | 80 | 20 | 100 | 94 | 6 | 0 |
| (Ia-5) + (B-13) 80 + 250 | 50 | 40 | 10 | 70 | 68 | 2 | 40 | 20 | 20 | 100 | 86 | 14 | 100 | 90 | 10 | 100 | 94 | 6 | 0 |
| (Ia-5) + (B-11) 80 + 250 | 90 | 40 | 50 | 100 | 60 | 40 | 40 | 0 | 40 | 100 | 72 | 28 | 100 | 90 | 10 | 100 | 64 | 36 | 0 |
| (Ia-5) + (B-18) 80 + 250 | 90 | 52 | 38 | 90 | 64 | 26 | 80 | 40 | 40 | 100 | 79 | 21 | 100 | 85 | 15 | 100 | 82 | 18 | 0 |
| (Ia-5) + (B-19) 80 + 250 | 80 | 40 | 40 | 90 | 60 | 30 | 100 | 10 | 90 | 100 | 65 | 35 | 100 | 85 | 15 | 100 | 76 | 24 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

TABLE 20

Soil treatment
(combined use of active ingredients)

| Dosage of each active ingredient (g/ha) | herbicidal efficacy (%) | | | | | | | | | | | | | | | | | phyto- toxicity corn |
|---|---|---|---|---|---|---|---|---|---|---|---|---|---|---|---|---|---|---|
| | (a) | | | (b) | | | (c) | | | (d) | | | (e) | | | (f) | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ia-7) + (B-7) 40 + 125 | 100 | 92 | 8 | 100 | 58 | 42 | 80 | 10 | 70 | 50 | 20 | 30 | 50 | 30 | 20 | 90 | 20 | 70 | 0 |
| (Ia-7) + (B-3) 40 + 125 | 100 | 92 | 8 | 100 | 93 | 7 | 100 | 91 | 9 | 80 | 36 | 44 | 100 | 30 | 70 | 100 | 44 | 56 | 0 |
| (Ia-7) + (B-2) 80 + 125 | 100 | 52 | 48 | 100 | 50 | 50 | 80 | 20 | 60 | 90 | 40 | 50 | 100 | 50 | 50 | 100 | 40 | 60 | 0 |
| (Ia-7) + (B-4) 40 + 500 | 90 | 20 | 70 | 100 | 44 | 56 | 100 | 36 | 64 | 90 | 20 | 70 | 100 | 30 | 70 | 100 | 30 | 70 | 0 |
| (Ia-7) + (B-12) 80 + 500 | 100 | 52 | 48 | 100 | 50 | 50 | 80 | 20 | 60 | 100 | 76 | 24 | 100 | 80 | 20 | 100 | 94 | 6 | 0 |
| (Ia-7) + (B-13) 80 + 250 | 60 | 40 | 20 | 80 | 60 | 20 | 80 | 36 | 44 | 100 | 88 | 12 | 100 | 90 | 10 | 100 | 94 | 6 | 0 |
| (Ia-7) + (B-11) 80 + 250 | 70 | 40 | 30 | 90 | 50 | 40 | 60 | 20 | 40 | 100 | 76 | 24 | 100 | 90 | 10 | 100 | 64 | 36 | 0 |
| (Ia-7) + (B-18) 80 + 250 | 80 | 52 | 28 | 90 | 55 | 35 | 80 | 52 | 28 | 100 | 82 | 18 | 100 | 85 | 15 | 100 | 82 | 18 | 0 |
| (Ia-7) + (B-19) 80 + 250 | 100 | 40 | 60 | 90 | 50 | 40 | 100 | 28 | 72 | 100 | 70 | 30 | 100 | 85 | 15 | 100 | 76 | 24 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

Tables 16-20 show that all the compositions containing Compound (Ia-2) and one of Compounds (B-2)~(B-4), (B-7), (B-12) and (B-13) in combination and all the compositions containing one of Compounds (Ia-2)~(Ia-5) and (Ia-7) and one of Compounds (B-2)~(B-4), (B-7), (B-11)~(B-13), (B-18) and (B-19) in combination showed synergistic herbicidal effects on all the weeds used for the test.

That is, in the compositions containing (Ia-2) and one of Compounds (B-2)~(B-4), (B-7), (B-12) and (B-13), the composition containing Compound (Ia-2) and Compound (B-7) showed a high synergistic effect on crabgrass, barnyard grass and slender amaranth in particular, the composition containing Compound (Ia-2) and Compound (B-) showed a high synergistic effect on in particular, the composition containing Compound (Ia-2) and Compound (B-3) showed a high synergistic effect on green foxtail, crabgrass and barnyard grass in particular, the composition containing Compound (Ia-2) and Compound (B-2) showed a high synergistic effect on cocklebur, slender amaranth, crabgrass and barnyard grass in particular, the composition containing Compound (Ia-2) and Compound (B-4) showed a high synergistic effect on cocklebur, slender amaranth and barnyard grass in particular, the composition containing Compound (Ia-2) and Compound (B-12) showed a high synergistic effect on velvet leaf and slender amaranth in particular, and the composition containing Compound (Ia-2) and Compound (B-13) showed a high synergistic effect on slender amaranth and crabgrass in particular.

Further, the compositions containing Compound (Ia-2) and one of Compounds (B-2)~(B-4) and (B-7) showed a herbicidal effect at an earlier stage than any individual herbicide used as a single active ingredient.

In the compositions containing Compound (Ia-3) and one of Compounds (B-2)~(B-4), (B-7), (B-11)~(B-13), (B-18) and (B-19), the composition containing Compound (Ia-3) and Compound (B-7) showed a high synergistic effect on velvet leaf, slender amaranth and crabgrass in particular, the composition containing Compound (Ia-3) and Compound (B-3) showed a high synergistic effect on green foxtail, crabgrass and barnyard grass in particular, the composition containing Compound (Ia-3) and Compound (B-2) showed a high synergistic effect on cocklebur, velvet leaf, slender amaranth, crabgrass and barnyard grass in particular, the composition containing Compound (Ia-3) and Compound (B-4) showed a high synergistic effect on cocklebur, velvet leaf, slender amaranth, green foxtail, crabgrass and barnyard grass in particular, the composition containing Compound (Ia-3) and Compound (B-12) showed a high synergistic effect on velvet leaf and slender amaranth in particular, the composition containing Compound (Ia-3) and Compound (B-13) showed a high synergistic effect on velvet leaf and slender amaranth in particular, the composition containing Compound (Ia-3) and Compound (B-11) showed a high synergistic effect on velvet leaf and slender amaranth in particular, the composition containing Compound (Ia-3) and Compound (B-18) showed a high synergistic effect on velvet leaf and slender amaranth in particular, and the composition containing Compound (Ia-3) and Compound (B-19) showed a high synergistic effect on velvet leaf and slender amaranth in particular.

In the compositions containing Compound (Ia-4) and one of Compounds (B-2)~(B-4), (B-7), (B-11)~(B-13), (B-18) and (B-19), the composition containing Compound (Ia-4) and Compound (B-7) showed a high synergistic effect on velvet leaf and slender amaranth in particular, the composition containing Compound (Ia-4) and Compound (B-3) showed a high synergistic effect on green foxtail, crabgrass and barnyard grass in particular, the composition containing Compound (Ia-4) and Compound (B-2) showed a high synergistic effect on cocklebur, slender amaranth, crabgrass and barnyard grass in particular, the composition containing Compound (Ia-4) and Compound (B-4) showed a high synergistic effect on cocklebur, slender amaranth, green foxtail, crabgrass and barnyard grass in particular, the composition containing Compound (Ia-4) and Compound (B-12) showed a high synergistic effect on slender amaranth in particular, the composition containing Compound (Ia-4) and Compound (B-13) showed a high synergistic effect on slender amaranth in particular, the composition containing Compound (Ia-4) and Compound (B-11) showed a high synergistic effect on cocklebur, slender amaranth and barnyard grass in particular, the composition containing Compound (Ia-4) and Compound (B-18) showed a high synergistic effect on cocklebur, velvet leaf and slender amaranth in particular, and the composition containing Compound (Ia-4) and Compound (B-19) showed a high synergistic effect on cocklebur and slender amaranth in particular.

In the compositions containing Compound (Ia-5) and one of Compounds (B-2)~(B-4), (B-7), (B-11)~(B-13), (B-18) and (B-19), the composition containing Compound (Ia-5) and Compound (B-7) showed a high synergistic effect on velvet leaf and slender amaranth in particular, the composition containing Compound (Ia-5) and Compound (B-3) showed a high synergistic effect on crabgrass and barnyard grass in particular, the composition containing Compound (Ia-5) and Compound (B-2) showed a high synergistic effect on cocklebur, green foxtail, crabgrass and barnyard grass in particular, the composition containing Compound (Ia-5) and Compound (B-4) showed a high synergistic effect on cocklebur, velvet leaf, slender amaranth, green foxtail, crabgrass and barnyard grass in particular, the composition containing Compound (Ia-5) and Compound (B-12) showed a high synergistic effect on cocklebur, velvet leaf and slender amaranth in particular, the composition containing Compound (Ia-5) and Compound (B-13) showed a high synergistic effect on slender amaranth in particular, the composition containing Compound (Ia-5) and Compound (B-11) showed a high synergistic effect on cocklebur, velvet leaf, slender amaranth and barnyard grass in particular, the composition containing Compound (Ia-5) and Compound (B-18) showed a high synergistic effect on cocklebur and slender amaranth in particular, and the composition containing Compound (Ia-5) and Compound (B-19) showed a high synergistic effect on slender amaranth in particular.

In the compositions containing Compound (Ia-7) and one of Compounds (B-2)~(B-4), (B-7), (B-11)~(B-13), (B-18) and (B-19), the composition containing Compound (Ia-7) and Compound (B-7) showed a high synergistic effect on slender amaranth and barnyard grass in particular, the composition containing Compound (Ia-7) and Compound (B-3) showed a high synergistic effect on crabgrass and barnyard grass in particular, the composition containing Compound (Ia-7) and Compound (B-2) showed a high synergistic effect on cocklebur, velvet leaf, slender amaranth, green foxtail, crabgrass and barnyard grass in particular, the composition containing Compound (Ia-7) and Compound (B-4) showed a high synergistic effect on cocklebur, velvet leaf, slender amaranth, green foxtail, crabgrass and barnyard grass in particular, the composition containing Compound (Ia-7) and Compound (B-12) showed a high synergistic effect on cocklebur, velvet leaf and slender amaranth in particular, the composition containing Compound (Ia-7) and Compound (B-13) showed a high synergistic effect on slender amaranth in particular, the composition containing Compound (Ia-7) and Compound (B-11) showed a high synergistic effect on velvet leaf, slender amaranth and barnyard grass in particular, the composition containing Compound (Ia-7) and Compound (B-18) showed a high synergistic effect on cocklebur, velvet leaf and slender amaranth in particular, and the composition containing Compound (Ia-7) and Compound (B-19) showed a high synergistic effect on cocklebur and slender amaranth in particular.

Table 21 shows the results of soil treatment tests on single active ingredients of Compounds (Ib-1)~(Ib-3) and Compounds (B-2)~(B-4), (B-7), (B-11)~(B-13), (B-18) and (B-19).

Table 22 to 24 show the results of soil treatment tests on compositions of one of Compounds (Ib-1)~(Ib-3) and one of Compounds (B-2)~(B-4), (B-7), (B-11)~(B-13), (B-18) and (B-19).

TABLE 21

Soil treatment (single active ingredient)

| Compd | Dosage (g/ha) | herbicidal efficacy % | | | | | | phytotoxicity to corn |
|---|---|---|---|---|---|---|---|---|
| | | (a) | (b) | (c) | (d) | (e) | (f) | |
| (Ib-1) | 80 | 20 | 60 | 20 | 40 | 80 | 40 | 0 |
| | 40 | 0 | 20 | 0 | 20 | 50 | 20 | 0 |
| (Ib-2) | 80 | 10 | 60 | 20 | 30 | 70 | 40 | 0 |
| | 40 | 0 | 20 | 0 | 0 | 20 | 0 | 0 |
| (Ib-3) | 80 | 20 | 50 | 20 | 30 | 60 | 40 | 0 |
| (B-2) | 125 | 0 | 0 | 0 | 0 | 0 | 0 | 0 |
| (B-3) | 62 | 90 | 90 | 60 | 0 | 40 | 0 | 0 |
| (B-4) | 250 | 0 | 20 | 20 | 0 | 0 | 0 | 0 |
| (B-7) | 62 | 40 | 20 | 0 | 0 | 0 | 0 | 0 |
| (B-11) | 250 | 0 | 0 | 0 | 60 | 80 | 40 | 0 |
| (B-12) | 125 | 0 | 0 | 0 | 20 | 60 | 60 | 0 |
| (B-13) | 125 | 0 | 0 | 0 | 80 | 80 | 20 | 0 |
| (B-18) | 250 | 20 | 10 | 40 | 70 | 70 | 70 | 0 |
| (B-19) | 250 | 0 | 0 | 10 | 50 | 70 | 60 | 0 |

(a): Cocklebur
(b): Velvet leaf
(c): Slender amaranth
(d): Green foxtail
(e): Crabgrass
(f): Barnyard grass

TABLE 22

Soil treatment (combined use of active ingredients)

| Dosage of each active ingredient (g/ha) | herbicidal efficacy (%) | | | | | | | | | | | | | | | | | phytotoxicity corn |
|---|---|---|---|---|---|---|---|---|---|---|---|---|---|---|---|---|---|---|
| | (a) | | | (b) | | | (c) | | | (d) | | | (e) | | | (f) | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ib-1) + (B-2) 80 + 125 | 80 | 20 | 60 | 100 | 60 | 40 | 100 | 20 | 80 | 100 | 40 | 60 | 100 | 80 | 20 | 100 | 40 | 60 | 0 |
| (Ib-1) + (B-3) 40 + 62 | 100 | 90 | 10 | 100 | 92 | 8 | 100 | 60 | 40 | 40 | 20 | 20 | 100 | 70 | 30 | 90 | 20 | 70 | 0 |
| (Ib-1) + (B-4) 80 + 250 | 80 | 20 | 60 | 100 | 68 | 32 | 80 | 36 | 44 | 80 | 40 | 40 | 80 | 40 | 40 | 90 | 80 | 10 | 0 |
| (Ib-1) + (B-7) 80 + 62 | 100 | 52 | 48 | 100 | 68 | 32 | 20 | 20 | 0 | 80 | 40 | 40 | 90 | 80 | 10 | 80 | 40 | 40 | 0 |
| (Ib-1) + (B-11) 80 + 250 | 60 | 20 | 40 | 100 | 60 | 40 | 20 | 20 | 0 | 100 | 76 | 24 | 100 | 96 | 4 | 100 | 64 | 36 | 0 |
| (Ib-1) + (B-12) 80 + 250 | 60 | 20 | 40 | 100 | 60 | 40 | 100 | 20 | 80 | 100 | 52 | 48 | 100 | 92 | 8 | 100 | 76 | 24 | 0 |
| (Ib-1) + (B-13) | 40 | 20 | 20 | 100 | 60 | 40 | 100 | 20 | 80 | 100 | 88 | 12 | 100 | 96 | 4 | 100 | 52 | 48 | 0 |

TABLE 22-continued

Soil treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| 80 + 125 (Ib-1) + (B-18) | 80 | 36 | 44 | 80 | 64 | 16 | 90 | 52 | 38 | 90 | 82 | 8 | 100 | 94 | 6 | 100 | 82 | 18 | 0 |
| 80 + 250 (Ib-1) + (B-19) 80 + 250 | 90 | 20 | 70 | 90 | 60 | 30 | 100 | 28 | 72 | 100 | 70 | 30 | 100 | 94 | 6 | 100 | 76 | 24 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

TABLE 23

Soil treatment
(combined use of active ingredients)

| Dosage of each active ingredient (g/ha) | herbicidal efficacy (%) | | | | | | | | | | | | | | | | | | phyto-toxicity corn |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ib-2) + (B-2) 80 + 125 | 80 | 10 | 70 | 100 | 60 | 40 | 90 | 20 | 70 | 100 | 30 | 70 | 100 | 70 | 30 | 100 | 40 | 60 | 0 |
| (Ib-2) + (B-3) 40 + 62 | 100 | 90 | 10 | 100 | 92 | 8 | 100 | 60 | 40 | 50 | 0 | 50 | 90 | 52 | 38 | 90 | 0 | 90 | 0 |
| (Ib-2) + (B-4) 80 + 250 | 80 | 10 | 70 | 100 | 68 | 32 | 90 | 36 | 54 | 90 | 30 | 60 | 90 | 70 | 20 | 90 | 40 | 50 | 0 |
| (Ib-2) + (B-7) 80 + 62 | 90 | 46 | 44 | 100 | 68 | 32 | 40 | 20 | 20 | 60 | 30 | 30 | 70 | 70 | 0 | 60 | 40 | 20 | 0 |
| (Ib-2) + (B-11) 80 + 250 | 50 | 10 | 40 | 100 | 60 | 40 | 40 | 20 | 20 | 100 | 72 | 28 | 100 | 94 | 6 | 100 | 64 | 36 | 0 |
| (Ib-2) + (B-12) 80 + 250 | 40 | 10 | 30 | 100 | 60 | 40 | 90 | 20 | 70 | 100 | 44 | 56 | 100 | 88 | 12 | 100 | 76 | 24 | 0 |
| (Ib-2) + (B-13) 80 + 125 | 50 | 10 | 40 | 100 | 60 | 40 | 100 | 20 | 80 | 100 | 86 | 14 | 100 | 94 | 6 | 100 | 52 | 48 | 0 |
| (Ib-2) + (B-18) 80 + 250 | 80 | 28 | 52 | 90 | 64 | 26 | 100 | 52 | 48 | 100 | 79 | 21 | 100 | 91 | 9 | 100 | 82 | 18 | 0 |
| (Ib-2) + (B-19) 80 + 250 | 90 | 10 | 80 | 90 | 60 | 30 | 100 | 28 | 72 | 100 | 65 | 35 | 100 | 91 | 9 | 100 | 76 | 24 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

TABLE 24

Soil treatment
(combined use of active ingredients)

| Dosage of each active ingredient (g/ha) | herbicidal efficacy (%) | | | | | | | | | | | | | | | | | | phyto-toxicity |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | corn |
| (Ib-3) + (B-2) 80 + 125 | 90 | 20 | 70 | 100 | 50 | 50 | 90 | 20 | 70 | 100 | 30 | 70 | 100 | 60 | 40 | 100 | 40 | 60 | 0 |
| (Ib-3) + (B-3) 40 + 62 | 100 | 92 | 8 | 100 | 95 | 5 | 90 | 68 | 22 | 80 | 30 | 50 | 100 | 76 | 24 | 90 | 40 | 50 | 0 |
| (Ib-3) + (B-4) 80 + 250 | 80 | 20 | 60 | 100 | 60 | 40 | 90 | 36 | 54 | 80 | 30 | 50 | 80 | 60 | 20 | 90 | 40 | 50 | 0 |
| (Ib-3 ) + (B-7) 80 + 62 | 90 | 52 | 38 | 100 | 60 | 40 | 50 | 20 | 30 | 70 | 30 | 40 | 90 | 60 | 30 | 80 | 40 | 40 | 0 |
| (Ib-3) + (B-11) 80 + 250 | 60 | 20 | 40 | 100 | 50 | 50 | 50 | 20 | 40 | 100 | 72 | 28 | 100 | 92 | 8 | 100 | 64 | 36 | 0 |
| (Ib-3) + (B-12) 80 + 150 | 80 | 20 | 60 | 100 | 50 | 50 | 100 | 20 | 80 | 100 | 44 | 56 | 100 | 84 | 16 | 90 | 76 | 14 | 0 |
| (Ib-3) + (B-13) 80 + 125 | 70 | 20 | 50 | 100 | 50 | 50 | 100 | 20 | 80 | 100 | 86 | 14 | 100 | 92 | 8 | 100 | 52 | 48 | 0 |
| (Ib-3) + (B-18) 80 + 250 | 80 | 36 | 44 | 100 | 55 | 45 | 100 | 52 | 48 | 90 | 79 | 11 | 100 | 88 | 12 | 100 | 82 | 18 | 0 |
| (Ib-3) + (B-19) 80 + 250 | 80 | 20 | 60 | 90 | 50 | 40 | 100 | 28 | 72 | 100 | 65 | 35 | 100 | 88 | 12 | 100 | 76 | 24 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

Tables 22, 23 and 24 show that all the compositions containing one of Compounds (Ib-1), (Ib-2) and (Ib-3) and one of Compounds (B-2)~(B-4), (B-7), (B-11)~(B-13), (B-18) and (B-19) in combination showed synergistic herbicidal effects on all the weeds used for the test.

That is, in the compositions containing (Ib-1) and one of Compounds (B-2)~(B-4), (B-7), (B-11)~(B-13), (B-18) and (B-19), the composition containing Compound (Ib-1) and Compound (B-2) showed a high synergistic effect on cocklebur, slender amaranth, green foxtail and barnyard grass in particular, the composition containing Compound (Ib-1) and Compound (B-3) showed a high synergistic effect on barnyard grass in particular, the composition containing Compound (Ib-1) and Compound (B-4) showed a high synergistic effect on cocklebur in particular, the composition containing Compound (Ib-1) and Compound (B-7) showed a high synergistic effect on cocklebur in particular, the composition containing Compound (Ib-1) and Compound (B-11) showed a high synergistic effect on cocklebur, velvetleaf and barnyard grass in particular, the composition containing Compound (Ib-1) and Compound (B-12) or (B-13) showed a high synergistic effect on slender amaranth in particular, and the composition containing Compound (Ib-1) and Compound (B-18) or (B-19) showed a high synergistic effect on cocklebur and slender amaranth in particular.

In the compositions containing (Ib-2) and one of Compounds (B-2)~(B-4), (B-7), (B-11)~(B-13), (B-18) and (B-19), the composition containing Compound (Ib-2) and Compound (B-2) or (B-4) showed a high synergistic effect on cocklebur, slender amaranth, green foxtail and barnyard grass in particular, the composition containing Compound (Ib-2) and Compound (B-3) showed a high synergistic effect on green foxtail and barnyard grass in particular, the composition containing Compound (Ib-2) and Compound (B-7) showed a high synergistic effect on cocklebur in particular, the composition containing Compound (Ib-2) and Compound (B-11) showed a high synergistic effect on cocklebur and velvet leaf in particular, the composition containing Compound (Ib-2) and Compound (B-12) showed a high synergistic effect on slender amaranth and green foxtail in particular, the composition containing Compound (Ib-2) and Compound (B-13) showed a high synergistic effect on slender amaranth in particular, and the composition containing Compound (Ib-2) and Compound (B-18) or (B-19) showed a high synergistic effect on cocklebur and slender amaranth in particular.

In the compositions containing (Ib-3) and one of Compounds (B-2)~(B-4), (B-7), (B-11)~(B-13), (B-18) and (B-19), the composition containing Compound (Ib-3) and Compound (B-2) showed a high synergistic effect on cocklebur, velvet leaf, slender amaranth, green foxtail and barnyard grass in particular, the composition containing Compound (Ib-3) and Compound (B-3) showed a high synergistic effect on green foxtail and barnyard grass in particular, the composition containing Compound (Ib-3) and Compound (B-4) showed a high synergistic effect on cocklebur, slender amaranth, green foxtail and barnyard grass in particular, the composition containing Compound (Ib-3) and Compound (B-7) showed a high synergistic effect on velvet leaf, green foxtail and barnyard grass in particular, the composition containing Compound (Ib-3) and Compound (B-11) showed a high synergistic effect on velvet leaf in particular, the composition containing Compound (Ib-3) and Compound (B-12) showed a high synergistic effect on cocklebur, velvet. leaf, slender amaranth and green foxtail in particular, the composition containing Compound (Ib-3) and Compound (B-13) or (B-18) showed a high synergistic effect on cocklebur, velvet leaf and slender amaranth in particular, and the composition containing Compound (Ib-3) and Compound (B-19) showed a high synergistic effect on cocklebur and slender amaranth in particular.

Table 25 shows the results of soil treatment tests on single active ingredients of Compounds (Ic-1) and (Ic-2) and Compounds (B-2)~(B-4), (B-7), (B-11)~(B-13), (B-18) and (B-19).

Table 26-27 show the results of soil treatment tests on compositions of one of Compounds (Ic-1) and (Ic-2) and one of Compounds (B-2)~(B-4), (B-7), (B-11)~(B-13), (B-18) and (B-19).

TABLE 25

Soil treatment (single active ingredient)

| Compd | Dosage (g/ha) | herbicidal efficacy % | | | | | | phytotoxicity to corn |
|---|---|---|---|---|---|---|---|---|
| | | (a) | (b) | (c) | (d) | (e) | (f) | |
| (Ic-1) | 80 | 50 | 60 | 0 | 30 | 40 | 30 | 0 |
| (Ic-2) | 80 | 40 | 60 | 0 | 40 | 40 | 30 | 0 |
| | 40 | 0 | 40 | 0 | 0 | 20 | 0 | 0 |
| (B-2) | 250 | 60 | 0 | 0 | 0 | 20 | 0 | 0 |
| (B-3) | 125 | 90 | 90 | 90 | 0 | 40 | 40 | 0 |
| (B-4) | 500 | 0 | 0 | 0 | 0 | 0 | 0 | 0 |
| (B-7) | 125 | 80 | 20 | 20 | 0 | 0 | 0 | 0 |
| (B-11) | 250 | 0 | 0 | 0 | 60 | 80 | 80 | 0 |
| (B-12) | 250 | 0 | 0 | 0 | 60 | 60 | 90 | 0 |
| (B-13) | 250 | 0 | 0 | 0 | 90 | 90 | 90 | 0 |
| (B-18) | 250 | 20 | 10 | 40 | 70 | 70 | 70 | 0 |
| (B-19) | 250 | 0 | 0 | 10 | 50 | 70 | 60 | 0 |

(a): Cocklebur
(b): Velvet leaf
(c): Slender amaranth
(d): Green foxtail
(e): Crabgrass
(f): Barnyard grass

TABLE 26

Soil treatment (combined use of active ingredients)

| Dosage of each active ingredient (g/ha) | (a) | | | (b) | | | (c) | | | (d) | | | (e) | | | (f) | | | phytotoxicity corn |
|---|---|---|---|---|---|---|---|---|---|---|---|---|---|---|---|---|---|---|---|
| | (F) | (E) | (Δ) | (F) | (E) | (Δ) | (F) | (E) | (Δ) | (F) | (E) | (Δ) | (F) | (E) | (Δ) | (F) | (E) | (Δ) | |
| (Ic-1) + (B-2) 80 + 250 | 100 | 80 | 20 | 100 | 60 | 40 | 90 | 0 | 90 | 80 | 30 | 50 | 100 | 52 | 48 | 100 | 30 | 70 | 0 |
| (Ic-1) + (B-3) 80 + 125 | 100 | 95 | 5 | 100 | 96 | 4 | 100 | 90 | 10 | 40 | 30 | 10 | 100 | 64 | 36 | 90 | 58 | 32 | 0 |
| (Ic-1) + (B-4) 80 + 500 | 90 | 50 | 40 | 100 | 60 | 40 | 100 | 0 | 100 | 60 | 30 | 30 | 60 | 40 | 20 | 100 | 30 | 70 | 0 |
| (Ic-1) + (B-7) 80 + 125 | 100 | 90 | 10 | 100 | 68 | 32 | 40 | 20 | 20 | 40 | 30 | 10 | 90 | 40 | 50 | 100 | 30 | 70 | 0 |
| (Ic-1) + (B-11) 80 + 250 | 80 | 50 | 30 | 100 | 60 | 40 | 30 | 0 | 30 | 100 | 72 | 28 | 100 | 88 | 12 | 100 | 86 | 14 | 0 |
| (Ic-1) + (B-12) 80 + 250 | 60 | 50 | 10 | 100 | 60 | 40 | 100 | 0 | 100 | 80 | 72 | 8 | 100 | 76 | 24 | 100 | 93 | 7 | 0 |
| (Ic-1) + (B-13) 80 + 250 | 80 | 50 | 30 | 100 | 60 | 40 | 100 | 0 | 100 | 100 | 93 | 7 | 100 | 90 | 10 | 100 | 90 | 10 | 0 |
| (Ic-1) + (B-18) 80 + 250 | 100 | 60 | 40 | 100 | 64 | 36 | 90 | 40 | 50 | 100 | 79 | 21 | 100 | 82 | 18 | 100 | 79 | 21 | 0 |
| (Ic-1) + (B-19) 80 + 250 | 90 | 50 | 40 | 100 | 60 | 40 | 80 | 10 | 70 | 100 | 65 | 35 | 100 | 82 | 18 | 100 | 72 | 28 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

TABLE 27

Soil treatment
(combined use of active ingredients)

| Dosage of each active ingredient (g/ha) | herbicidal efficacy (%) | | | | | | | | | | | | | | | | | | phytotoxicity |
|---|---|---|---|---|---|---|---|---|---|---|---|---|---|---|---|---|---|---|---|
| | (a) | | | (b) | | | (c) | | | (d) | | | (e) | | | (f) | | | |
| | (F) | (E) | (Δ) | (F) | (E) | (Δ) | (F) | (E) | (Δ) | (F) | (E) | (Δ) | (F) | (E) | (Δ) | (F) | (E) | (Δ) | corn |
| (Ic-2) + (B-2) 80 + 250 | 100 | 76 | 24 | 100 | 60 | 40 | 100 | 0 | 100 | 80 | 40 | 40 | 100 | 52 | 48 | 100 | 30 | 70 | 0 |
| (Ic-2) + (B-3) 80 + 125 | 100 | 90 | 10 | 100 | 94 | 6 | 100 | 90 | 10 | 40 | 0 | 40 | 100 | 64 | 36 | 90 | 40 | 50 | 0 |
| (Ic-2) + (B-4) 80 + 500 | 90 | 40 | 50 | 100 | 60 | 40 | 100 | 0 | 100 | 60 | 40 | 20 | 60 | 40 | 20 | 100 | 30 | 70 | 0 |
| (Ic-2) + (B-7) 80 + 125 | 100 | 88 | 12 | 100 | 68 | 32 | 40 | 20 | 20 | 40 | 40 | 0 | 90 | 40 | 50 | 100 | 30 | 70 | 0 |
| (Ic-2) + (B-11) 80 + 250 | 80 | 40 | 40 | 100 | 60 | 40 | 0 | 0 | 0 | 100 | 76 | 24 | 100 | 88 | 12 | 100 | 86 | 14 | 0 |
| (Ic-2) + (B-12) 80 + 250 | 60 | 40 | 20 | 100 | 60 | 40 | 100 | 0 | 100 | 80 | 76 | 4 | 100 | 76 | 24 | 100 | 93 | 7 | 0 |
| (Ic-2) + (B-13) 80 + 250 | 40 | 40 | 0 | 100 | 60 | 40 | 100 | 0 | 100 | 100 | 94 | 6 | 100 | 94 | 6 | 100 | 93 | 7 | 0 |
| (Ic-2) + (B-18) 80 + 250 | 90 | 52 | 38 | 90 | 64 | 26 | 80 | 40 | 40 | 100 | 82 | 18 | 100 | 82 | 18 | 100 | 79 | 21 | 0 |
| (Ic-2) + (B-19) 80 + 250 | 90 | 40 | 50 | 90 | 60 | 30 | 80 | 10 | 70 | 100 | 70 | 30 | 100 | 82 | 18 | 100 | 72 | 28 | 0 |

(a): Cocklebur
(b): Velvet leaf
(c): Slender amaranth
(d): Green foxtail
(e): Crabgrass
(f): Barnyard grass
Difference (Δ) = Found value (F) - Expected value (E)
A larger difference (Δ) means a larger synergistic effect due to the combined use of active ingredients.

Tables 26 and 27 show that all the compositions containing one of Compounds (Ic-1) and (Ic-2) and one of Compounds (B-2)~(B-4), (B-7), (B-11)~(B-13), (B-18) and (B-19) in combination showed synergistic herbicidal effects on all the weeds used for the test.

That is, in the compositions containing (Ic-1) and one of Compounds (B-2)~(B-4), (B-7), (B-11)~(B-13), (B-18) and (B-19), the composition containing Compound (Ic-1) and Compound (B-2) showed a high synergistic effect on slender amaranth, velvet leaf, green foxtail, crabgrass and barnyard grass in particular, the composition containing Compound (Ic-1) and Compound (B-) showed a high synergistic effect on in particular, the composition containing Compound (Ic-1) and Compound (B-3) showed a high synergistic effect on barnyard grass in particular, the composition containing Compound (Ic-1) and Compound (B-4) showed a high synergistic effect on cocklebur, slender amaranth, velvet leaf and barnyard grass in particular, the composition containing Compound (Ic-1) and Compound (B-7) showed a high synergistic effect on velvet leaf, crabgrass and barnyard grass in particular, the composition containing Compound (Ic-1) and Compound (B-11) showed a high synergistic effect on cocklebur, velvet leaf and slender amaranth in particular, the composition containing Compound (Ic-1) and Compound (B-12) showed a high synergistic effect on slender amaranth, velvet leaf and crabgrass in particular, and the composition containing Compound (Ic-1) and Compound (B-13), (B-18) or (B-19) showed a high synergistic effect on cocklebur, slender amaranth and velvet leaf in particular.

In the compositions containing (Ic-2) and one of Compounds (B-2)~(B-4), (B-7), (B-11)~(B-13), (B-18) and (B-19), the composition containing Compound (Ic-2) and Compound (B-2) showed a high synergistic effect on slender amaranth and barnyard grass in particular, the composition containing Compound (Ic-2) and Compound (B-3) showed a high synergistic effect on barnyard grass in particular, the composition containing Compound (Ic-2) and Compound (B-4) showed a high synergistic effect on cocklebur, slender amaranth and barnyard grass in particular, the composition containing Compound (Ic-2) and Compound (B-7) showed a high synergistic effect on crabgrass and barnyard grass in particular, the composition containing Compound (Ic-2) and Compound (B-11) showed a high synergistic effect on cocklebur and velvet leaf in particular, the composition containing Compound (Ic-2) and Compound (B-12) showed a high synergistic effect on slender amaranth and crabgrass in particular, the composition containing Compound (Ic-2) and Compound (B-13) showed a high synergistic effect on slender amaranth in particular, and the composition containing Compound (Ic-2) and Compound (B-19) showed a high synergistic effect on cocklebur and slender amaranth in particular.

The herbicide composition of the present invention not only exhibits high herbicidal efficacy but also has a broad herbicidal spectrum on the basis of the synergistic effect of the pyrazole derivative of the general formula (I) and at least one of Compounds (B-1)-(B-20) which are active ingredients thereof. Further, the herbicide composition of the present invention exhibits high activity against weeds which are hard to control. Moreover, the herbicide composition of the present invention has high safety for crops such as corn, etc., and is free from damaging (causing phytotoxicity to) crops.

We claim:

1. A herbicide composition containing, as active ingredients, a pyrazole derivative of the general formula (I),

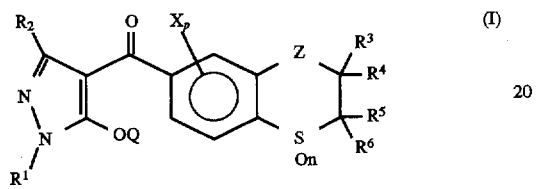

{wherein:

$R^1$ is a $C_1$~$C_4$ alkyl group, a $C_2$~$C_4$ alkenyl group or a $C_2$~$C_4$ haloalkeny group, $R^2$ is a hydrogen atom, a $C_1$~$C_4$ alkyl group, a $C_1$~$C_4$ haloalkyl group or a $C_2$~$C_4$ alkoxyalkyl group, X is a $C_1$~$C_4$ alkyl group, a $C_1$~$C_4$ haloalkyl group, a $C_2$~$C_4$ alkoxyalkyl group, a halogen atom, a $C_1$~$C_4$ alkoxy group or a $C_1$~$C_4$ haloalkoxy group, p is an integer of 0, 1 or 2, each of $R^3$, $R^4$, $R^5$ and $R^6$ is independently a hydrogen atom, a $C_1$~$C_4$ alkyl group, a $C_1$~$C_4$ haloalkyl group or a $C_2$~$C_4$ alkoxyalkyl group, n is an integer of 0, 1 or 2, Q is a hydrogen atom or a group of A—B, (in which A is a group of

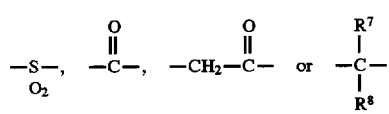

(in which each of $R^7$ and $R^8$ is independently a hydrogen atom or a $C_1$~$C_4$ alkyl group), and B is a $C_1$~$C_{12}$ alkyl group, a $C_3$~$C_{10}$ cycloalkyl group or a group of

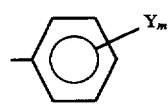

(in which Y is a $C_1$~$C_4$ alkyl group, a $C_1$~$C_4$ alkoxy group, a $C_1$~$C_4$ haloalkyl group, a nitro group or a halogen atom, and m is an integer of 0 or 1~3)), and Z is

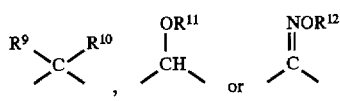

(in which $R^9$ is a hydrogen atom, a $C_1$~$C_4$ alkyl group or a $C_1$~$C_4$ haloalkyl group, $R^{10}$ is a hydrogen atom, a $C_1$~$C_4$ alkyl group, a $C_2$~$C_4$ alkenyl group or a $C_2$~$C_4$ alkynyl group, $R^{11}$ is a $C_1$~$C_4$ alkyl group, a $C_1$~$C_4$ haloalkyl group, a $C_3$~$C_6$ cycloalkyl group, a $C_3$~$C_6$ alkenylalkyl group, a $C_3$~$C_6$ alkynylalkyl group or a $C_3$~$C_6$ haloalkenylalkyl group, $R^{12}$ is a $C_1$~$C_4$ alkyl group, a $C_1$~$C_4$ haloalkyl group, a $C_3$~$C_6$ cycloalkyl group, a $C_3$~$C_6$ alkenylalkyl group, a $C_3$~$C_6$ alkynylalkyl group or a $C_3$~$C_6$ haloalkenylalkyl group)}, or a salt thereof; and at least one herbicide compound selected from the group consisting of a choroacetamide-based herbicide, an imidazoline-based herbicide, and Compound(B-1)

Common name: atrazine

Chemical Name:

6-chloro-$N^2$-ethyl-$N^4$-isopropil-1,3,5-triazine-2,4-diamine

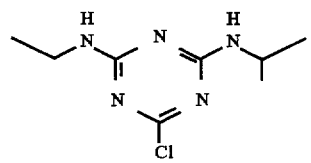

Compound(B-2)

Common name: cyanazine

Chemical Name:

2-(4-chloro-6-ethylamino-1,3,5-triazin-2-ylamino)-2-methylpropionitrile

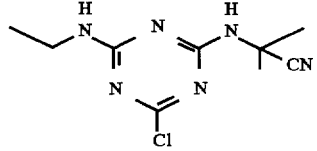

Compound(B-3)

Common name: metribuzin
Chemical Name:

4-amino-6-tert-buthyl-4,5-dihydro-3-methylthio-1,2,4-triazin-5-one

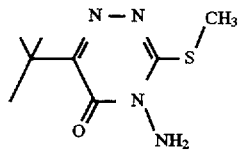

Compound(B-4)

Common name: linuron
Chemical Name:

3-(3,4-dichlorophenyl)-1-methoxy-1-methylurea

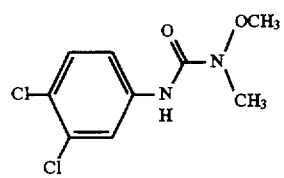

Compound(B-5)

Common name: metobenzurone
Chemical Name:

(±)-1-methoxy-3-[4-(2-methoxy-2,4,4-trimethylchroman-7-yloxy)phenyl]-1-methylurea

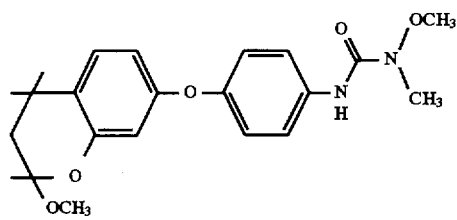

Compound(B-6)

Common name: bentazone
Chemical Name:

3-isopropyl-1H-2,1,3-benzothiadin-4(3H)-one-2,2-dioxide

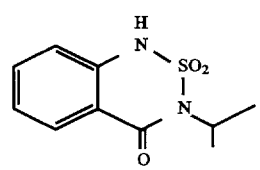

Compound(B-7)

Common name: dicamba
Chemical Name:

3,6-dichloro-2-methoxybenzoic acid

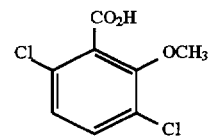

Compound(B-8)

Common name: chlopyralid
Chemical Name:

3,6-dichloropyridine-2-carboxylic acid

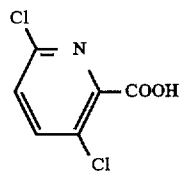

Compound(B-9)

Common name: 2,4-D
Chemical Name:

2-(2,4-dichlorophenoxy)acetic acid

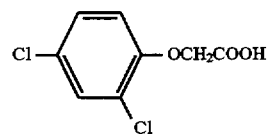

Compound(B-10)

Common name: bromoxynil
Chemical Name:

3,5-dibromo-4-hydroxybenzonitrile

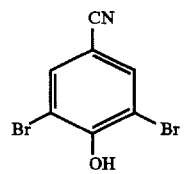

Compound (B-13)

Common name: pendimethalin

Chemical Name:

N-(1-ethylpropyl)-2,6-dinitro-3,4-xylidine

Compound(B-14)

Common name: nicosulfuron

Chemical Name:

2-(4,6-dimethoxypyrimidin-2-ylcarbamoylsulfamoyl)-N,N-dimethylnicotineamide

Compound(B-15)

Common name: rimsulfuron

Chemical Name:

1-(4,6-dimethoxypyrimidin-3-(3-ethylsulfonyl-2-pyridylsulfonyl)urea

Compound(B-17)

Common name: primisulfuron

Chemical Name:

Methyl 2-[4,6-bis(difluoromethoxy)pyrimidin-2-yl-carbamoylsulfamoyl]benzoic acid

Compound(B-20)

Common name: pyridate

Chemical Name:

6-chloro-3-phenylpyridazin-4-yl-S-octylthiocarbonate

2. The herbicide composition of claim 1, wherein the chloroacetamide-based herbicide is at least one herbicide compound selected from the group consisting of

Compound(B-11)

Common name: alachlor

Chemical Name:

2-chloro-2',6'-diethyl-N-methoxymethylacetanilide

Compound(B-12)

Common name: metolachlor

Chemical Name:

2-chloro-N-(2-ethyl-6-methylphenyl)-N-(2-methoxy-1-methylethyl)acetamide

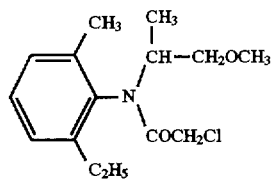

Compound(B-18)

Common name: dimethenamid

Chemical Name:

(1RS,aRS)-2-chloro-N-(2,4-dimethyl-3-thienyl)-N-(2-methoxy-1-methylethyl)acetamide

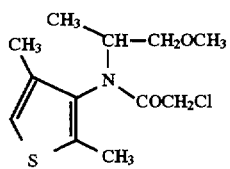

Compound(B-19)

Common name: acetochlor

Chemical Name:

2-chloro-2'-ethyl-6'-methyl-N-ethoxymethylacetanilide

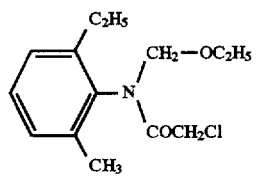

3. The herbicide composition of claim 1, wherein the imidazoline-based herbicide is at least one herbicide compound selected from the group consisting of Compound (B-16)

Common name: imazethapyr

Chemical Name:

5-ethyl-2-(4-isopropil-4-methyl-5-oxo-2-imidazolin-2-yl)-nicotinic acid

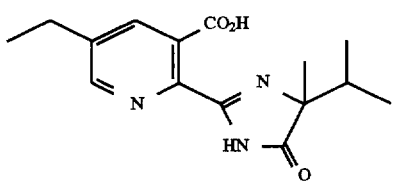

Compound(B-21)

Common name: imazamethabenz-methyl

Chemical Name:

Compound of a Methyl 6-(4-isopropyl-4-methyl-5-oxo-2-imidazolin-2-yl)-m-toluic acid and Methyl 6-(4-isopropyl-4-methyl-5-oxo-2-imidazolin-2-yl)-p-toluic acid

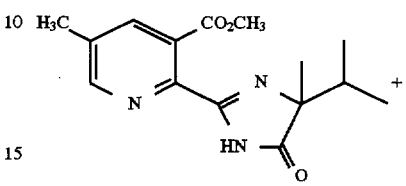

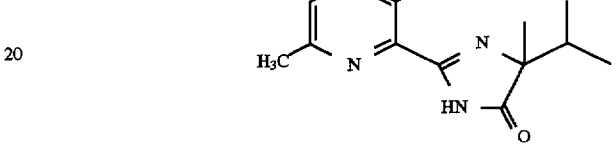

4. The herbicide composition of claim 1, wherein in the general formula (I) $R^1$ is a $C_3$~$C_4$ alkyl group.

5. The herbicide composition of claim 1, wherein in the general formula (I) $R^2$ is a hydrogen atom or a $C_1$~$C_4$ alkyl group.

6. The herbicide composition of claim 1, wherein in the general formula (I) X is a $C_1$~$C_4$ alkyl group or a halogen atom.

7. The herbicide composition of claim 1, wherein substituent(s) X is/are substituted on the 5-position and/or 8-position of a thiochroman ring.

8. The herbicide composition of claim 1, wherein in the general formula (I) each of $R^3$, $R^4$, $R^5$ and $R^6$ is independently a hydrogen atom or a $C_1$~$C_4$ alkyl group.

9. The herbicide composition of claim 1, wherein in the general formula (I) n is 2.

10. The herbicide composition of claim 1, wherein in the general formula (I) Q is a group of —A—B in which B is a group of

in which Y is a $C_1$~$C_4$ alkyl group, a $C_1$~$C_4$ alkoxy group, a nitro group or a halogen atom.

11. The herbicide composition of any one of claims 1 to 3, wherein the herbicide composition contains the pyrazole derivative of the general formula (I) and one of Compounds (B-1)~(B-20) in the following mixing ratio (weight ratio), pyrazole derivative(I): compound(B-1:atrazine)=2:1~1:50
pyrazole derivative(I): compound(B-2:cyanazine)=2:1~1:50
pyrazole derivative(I): compound(B-3:metribuzin)= 3:1~1:25
pyrazole derivative(I): compound(B-4:linuron)=2:1~1:50
pyrazole derivative(I): compound(B-5:metobenzuron)= 1:2~1:100
pyrazole derivative(I): compound(B-6:bentazone)= 6:1~1:100 pyrazole derivative(I): compound(B-7:dicamba)=1:1~1:50
pyrazole derivative(I): compound(B-8:chlopyralid)= 4:3~1:12
pyrazole derivative(I): compound(B-9:2,4-D)=2:1~1:5
pyrazole derivative(I): compound(B-10:bromoxynil)= 1:1~1:50
pyrazole derivative(I): compound(B-11:alachlor)=2:1~1:25
pyrazole derivative(I): compound(B-12:metolachlor)= 2:1~1:25
pyrazole derivative(I): compound(B-13:pendimethalin)= 2:1~1:25
pyrazole derivative(I): compound(B-14:nicosulfuron)= 1:3~40:1
pyrazole derivative(I): compound(B-15:rimsulfuron)= 1:3~40:1
pyrazole derivative(I): compound(B-16:imazethapyr)= 1:6~40:1
pyrazole derivative(I): compound(B-17:primisulfuron)= 1:3~40:1
pyrazole derivative(I): compound(B-18:dimethenamid)= 2:1~1:50
pyrazole derivative(I): compound(B-19:acetochlor)= 2:1~1:50
pyrazole derivative(I): compound(B-20:pyridate)=3:2~1:50
pyrazole derivative(I): compound(B-21:imazamethabenzmethyl)=1:6~40:1.

12. The herbicide composition of claim 1, wherein the pyrazole derivative of the general formula (I) is a pyrazole derivative of the general formula (Ia),

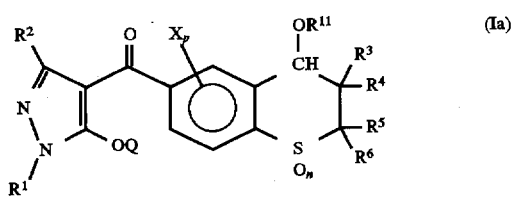

(wherein $R^1$, $R^2$, $R^3$, $R^4$, $R^5$, $R^6$, X, p, n, Q and $R^{11}$ are as defined in claim 1) or a salt thereof.

13. The herbicide composition of claim 12, wherein the general formula (Ia),

is selected from the group consisting of

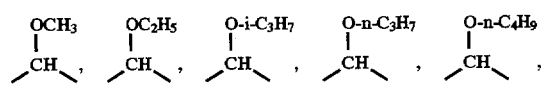

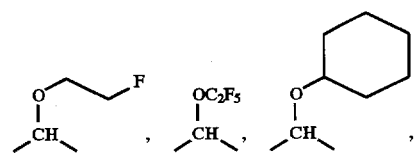

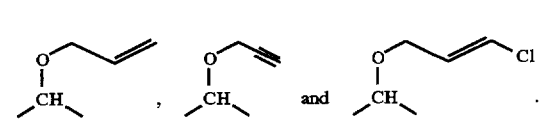

14. The herbicide composition of claim 12, wherein the herbicide composition contains the pyrazole derivative of the general formula (Ia) and one of Compounds (B-1)~(B-20) in the following mixing ratio (weight ratio), pyrazole derivative(Ia): compound(B-1:atrazine)=1:1~1:50
pyrazole derivative(Ia): compound(B-2:cyanazine)= 2:1~1:25
pyrazole derivative(Ia): compound(B-3:metribuzin)= 3:1~1:12
pyrazole derivative(Ia): compound(B-4:linuron)=2:1~1:25
pyrazole derivative(Ia): compound(B-6:bentazone)= 1:2~1:100
pyrazole derivative(Ia): compound(B-7:dicamba)=1:1~1:50
pyrazole derivative(Ia): compound(B-9:2,4-D)=2:1~1:50
pyrazole derivative(Ia): compound(B-10:bromoxynil)= 1:1~1:50
pyrazole derivative(Ia): compound(B-11:alachlor)= 2:1~1:25
pyrazole derivative(Ia): compound(B-12:metolachlor)= 2:1~1:25
pyrazole derivative(Ia): compound(B-13:pendimethalin)= 2:1~1:25
pyrazole derivative(Ia): compound(B-14:nicosulfuron)= 1:3~40:1
pyrazole derivative(Ia): compound(B-15:rimsulfuron)= 1:3~40:1
pyrazole derivative(Ia): compound(B-16:imazethapyr)= 1:6~40:1
pyrazole derivative(Ia): compound(B-17:primisulfuron)= 1:3~40:1
pyrazole derivative(Ia): compound(B-18:dimethenamid)= 2:1~1:50
pyrazole derivative(Ia): compound(B-19:acetochlor)= 2:1~1:50
pyrazole derivative(Ia): compound(B-20:pyridate)= 3:2~1:50.

15. The herbicide composition of claim 1, wherein the pyrazole derivative of the general formula (I) is a pyrazole derivative of the general formula (Ib),

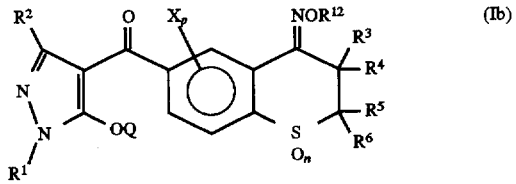

(wherein $R^1$, $R^2$, $R^3$, $R^4$, $R^5$, $R^6$, X, p, n, Q and $R^{12}$ are as defined in claim 1) or a salt thereof.

16. The herbicide composition of claim 15, wherein in the general formula (Ib),

is selected from the group consisting of

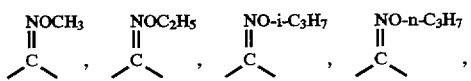

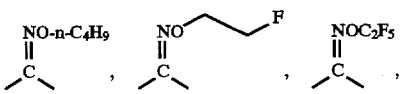

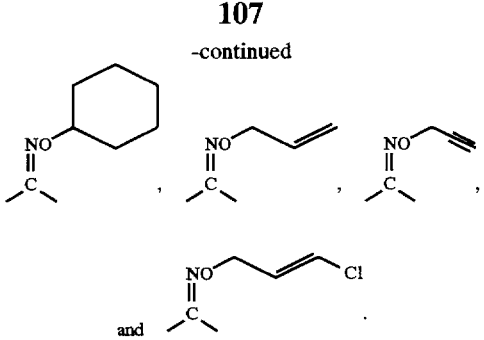

and

17. The herbicide composition of claim 15, wherein the herbicide composition contains the pyrazole derivative of the general formula (Ib) and one of Compounds (B-1)~(B-19) in the following mixing ratio (weight ratio), pyrazole derivative(Ib): compound(B-1:atrazine)=2:1~1:50
pyrazole derivative(Ib): compound(B-2:cyanazine)= 2:1~1:50
pyrazole derivative(Ib): compound(B-3:metribuzin)= 3:1~1:25
pyrazole derivative(Ib): compound(B-4:linuron)=2:1~1:50
pyrazole derivative(Ib): compound(B-5:metobenzuron)= 1:2~1:100
pyrazole derivative(Ib): compound(B-6:bentazone)=6:1~1:3
pyrazole derivative(Ib): compound(B-7:dicamba)=1:1~1:50
pyrazole derivative(Ib): compound(B-8:chlopyralid)= 4:3~1:12
pyrazole derivative(Ib): compound(B-9:2,4-D)=2:1~1:50
pyrazole derivative(Ib): compound(B-10:bromoxynil)= 1:1~1:50
pyrazole derivative(Ib): compound(B-11:alachlor)= 2:1~1:25
pyrazole derivative(Ib): compound(B-12:metolachlor)= 2:1~1:25
pyrazole derivative(Ib): compound(B-13:pendimethalin)= 2:1~1:25
pyrazole derivative(Ib): compound(B-14:nicosulfuron)= 1:3~40:1
pyrazole derivative(Ib): compound(B-15:rimsulfuron)= 1:3~40:1
pyrazole derivative(Ib): compound(B-16:imazethapyr)= 1:6~40:1
pyrazole derivative(Ib): compound(B-17:primisulfuron)= 1:3~40:1
pyrazole derivative(Ib): compound(B-18:dimethenamid)= 2:1~1:50
pyrazole derivative(Ib): compound(B-19:acetochlor)= 2:1~1:50.

18. The herbicide composition of claim 1, wherein the pyrazole derivative of the general formula (I) is a pyrazole derivative of the general formula (Ic),

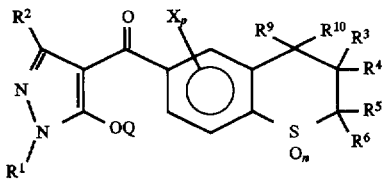

(wherein $R^1$, $R^2$, $R^3$, $R^4$, $R^5$, $R^6$, X, p, n, Q, $R^9$ and $R^{10}$ are as defined in claim 1) or a salt thereof.

19. The herbicide composition of claim 18, wherein in the general formula (Ic),

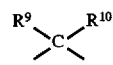

is selected from the group consisting of

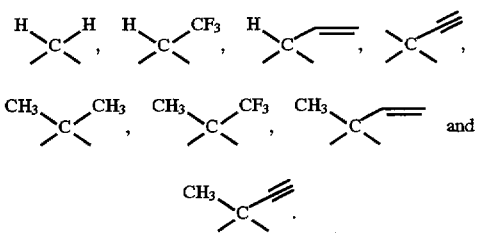

20. The herbicide composition of claim 18, wherein the herbicide composition contains the pyrazole derivative of the general formula (Ic) and one of Compounds (B-1)~(B-4) and (B-6)~(B-19) in the following mixing ratio (weight ratio), pyrazole derivative(Ic): compound(B-1:atrazine)=2:1~1:50
pyrazole derivative(Ic): compound(B-2:cyanazine)= 2:1~1:50
pyrazole derivative(Ic): compound(B-3:metribuzin)= 3:1~1:25
pyrazole derivative(Ic): compound(B-4:linuron)=2:1~1:50
pyrazole derivative(Ic): compound(B-6:bentazone)= 1:2~1:100
pyrazole derivative(Ic): compound(B-7:dicamba)=1,1~1:50
pyrazole derivative(Ic): compound(B-8:chlopyralid)= 4:3~1:12
pyrazole derivative(Ic): compound(B-9:2,4-D)=2:1~1:50
pyrazole derivative(Ic): compound(B-10:bromoxynil)= 1.1~1:50
pyrazole derivative(Ic): compound(B-11:alachlor)= 2:1~1:25
pyrazole derivative(Ic): compound(B-12:metolachlor)= 2:1~1:25
pyrazole derivative(Ic): compound(B-13:pendimethalin)= 2:1~1:25
pyrazole derivative(Ic): compound(B-14:nicosulfuron)= 1:3~40:1
pyrazole derivative(Ic): compound(B-15:rimsulfuron)= 1:3~40:1
pyrazole derivative(Ic): compound(B-16:imazethapyr)= 1:6~40:1
pyrazole derivative(Ic): compound(B-17:primisulfuron)= 1:3~40:1
pyrazole derivative(Ic): compound(B-18:dimethenamid)= 2:1~1:50
pyrazole derivative(Ic): compound(B-19:acetochlor)= 2:1~1:50.

* * * * *